US007368537B2

(12) United States Patent
Anderson et al.

(10) Patent No.: US 7,368,537 B2
(45) Date of Patent: May 6, 2008

(54) SUBUNIT VACCINE AGAINST RESPIRATORY SYNCYTIAL VIRUS INFECTION

(75) Inventors: Robert Anderson, Halifax (CA); Yan Huang, Cochrane (CA); David S. Burt, Dollard des Ormeaux (CA)

(73) Assignee: ID Biomedical Corporation of Quebec, Ville St-Laurent, Quebec (CA)

( * ) Notice: Subject to any disclaimer, the term of this patent is extended or adjusted under 35 U.S.C. 154(b) by 431 days.

(21) Appl. No.: 10/888,805

(22) Filed: Jul. 9, 2004

(65) Prior Publication Data

US 2005/0042230 A1 Feb. 24, 2005

Related U.S. Application Data

(60) Provisional application No. 60/567,586, filed on May 3, 2004, provisional application No. 60/487,804, filed on Jul. 15, 2003.

(51) Int. Cl.
*C07K 14/135* (2006.01)

(52) U.S. Cl. ................. 530/350; 424/185.1; 424/204.1

(58) Field of Classification Search ................ 530/350; 424/204.1, 185.1, 204
See application file for complete search history.

(56) References Cited

U.S. PATENT DOCUMENTS

| | | | | |
|---|---|---|---|---|
| 4,707,543 | A | 11/1987 | Zollinger et al. | 530/402 |
| 5,716,637 | A | 2/1998 | Anselem et al. | 424/450 |
| 5,726,292 | A | 3/1998 | Lowell | 530/403 |
| 5,848,152 | A | 12/1998 | Slipy et al. | |
| 5,961,970 | A | 10/1999 | Lowell et al. | 424/93.1 |
| 5,985,284 | A | 11/1999 | Lowell | 424/234.1 |
| 6,476,201 | B1 | 11/2002 | Lowell et al. | 530/414 |
| 6,699,478 | B1 | 3/2004 | Hancock et al. | 424/211.1 |
| 2001/0053368 | A1 | 12/2001 | Burt et al. | 424/206.1 |
| 2003/0044425 | A1 | 3/2003 | Burt et al. | 424/203.1 |
| 2004/0197348 | A1 | 10/2004 | Hancock et al. | 424/186.1 |

FOREIGN PATENT DOCUMENTS

| | | | |
|---|---|---|---|
| WO | WO 99/14334 | A1 | 3/1999 |
| WO | WO 01/60402 | A2 | 8/2001 |
| WO | WO 02/058725 | A2 | 8/2002 |

OTHER PUBLICATIONS

Murphy et al. Virus Research 1994 vol. 32, pp. 13-36.*
Mader et al. Vaccine 2000 vol. 18, pp. 1110-1117.*
Huang et al. Vaccine vol. 21, pp. 2500-2505, 2003.*
Beasley, R. et al., "Viral respiratory tract infection and exacerbations of asthma in adult patients," *Thorax*, 43(9):679-683, Sep. 1988.
Connors, M. et al., "Enhanced Pulmonary Histopathology Induced by Respiratory Syncytial Virus (RSV) Challenge of Formalin-Inactivated RSV-Immunized BALB/c Mice Is Abrogated by Depletion of Interleukin-4 (IL-4) and IL-10," *Journal of Virology*, 68(8):5321-5325, Aug. 1994.
Doherty, P.C., "Vaccines and cytokine-mediated pathology in RSV infection," *Trends Microbiol.*, 2:148, 1994.
Glezen, W.P. et al., "Risk of Primary Infection and Reinfection With Respiratory Syncytial Virus," *American Journal of Diseases of Children*, 140(6):543-546, Jun. 1986.
Glezen, W.P. et al., "Risk of respiratory syncytial virus infection for infants from low-income families in relationship to age, sex, ethnic group, and maternal antibody level," *The Journal of Pediatrics*, 98(5):708-715, May 1981.
Graham, B.S. et al., "Priming Immunization Determines T Helper Cytokine mRNA Expression Patterns in Lungs of Mice Challenged with Respiratory Syncytial Virus," *The Journal of Immunology*, 151(4):2032-2040, Aug. 15, 1993.
Grünig, G. et al., "Requirement for IL-13 Independently of IL-4 in Experimental Asthma," *Science*, 282(5397):2261-2263, Dec. 18, 1998.
Hemming, V.G. et al., "Hyperimmune Globulins in Prevention and Treatment of Respiratory Syncytial Virus Infections," *Clinical Microbiology Reviews*, 8(1):22-33, Jan. 1995.
Holberg, C.J. et al., "Risk Factors for Respiratory Syncytial Virus-associated Lower Respiratory Illnesses in the First Year of Life," *American Journal of Epidemiology*, 133(11):1135-1151, Jun. 1, 1991.
Huang, Y. and Anderson, R., "A single amino acid substitution in a recombinant G protein vaccine drastically curtails protective immunity against respiratory syncytial virus (RSV)," *Vaccine*, 21:2500-2505, 2003.
Huang, Y. and Anderson, R., "Enhanced immune protection by a liposome-encapsulated recombinant respiratory syncytial virus (RSV) vaccine using immunogenic lipids from *Deinococcus radiodurans*," *Vaccine*, 20:1586-1592, 2002.
Hussell, T. and Openshaw, P.J.M., "Intracellular IFN-γ expression in natural killer cells precedes lung $CD8^+$ T cell recruitment during respiratory syncytial virus infection," *Journal of General Virology*, 79:2593-2601, 1998.
Johnson, T.R. and Graham, B.S., "Secreted Respiratory Syncytial Virus G Glycoprotein Induces Interleukin-5 (IL-5), IL-13, and Eosinophilia by an IL-4-Independent Mechanism," *Journal of Virology*, 73(10):8485-8495, Oct. 1999.
Kakuk, T.J. et al., "A Human Respiratory Syncytial Virus (RSV) Primate Model of Enhanced Pulmonary Pathology Induced with a Formalin-Inactivated RSV Vaccine but Not a Recombinant FB Subunit Vaccine," *The Journal of Infectious Diseases*, 167(3):553-561, Mar. 1993.
Kirby, C. and Gregoriadis, G., "Dehydration-Rehydration Vesicles: A Simple Method for High Yield Drug Entrapment in Liposomes," *Bio/Technology*, 2:979-984, Nov. 1984.

(Continued)

*Primary Examiner*—Bruce H. Campell
*Assistant Examiner*—Myron G. Hill
(74) *Attorney, Agent, or Firm*—Gwynedd Warren; Elizabeth J. Hecht; Edward R. Gimmi

(57) ABSTRACT

The present invention relates generally to methods of treating or preventing RSV infections, and more specifically, to compositions, and the use thereof, comprising one or more RSV G protein immunogen or fragment thereof capable of eliciting protective immunity without eliciting an immunopathological response or eliciting a reduced immunopathological response.

14 Claims, 8 Drawing Sheets

OTHER PUBLICATIONS

Lamprecht, C.L. et al., "Role of Maternal Antibody in Pneumonia and Bronchiolitis Due to Respiratory Syncytial Virus," *The Journal of Infectious Diseases*, 134(3):211-217, Sep. 1976.

Levine, S. et al., "Demonstration that Glycoprotein G Is the Attachment Protein of Respiratory Syncytial Virus," *The Journal of General Virology*, 68:2521-2524, 1987.

Lowell, G.H. et al., "Peptides Bound to Proteosomes via Hydrophobic Feet Become Highly Immunogenic Without Adjuvants," *The Journal of Experimental Medicine*, 167(2):658-663, Feb. 1, 1988.

Lowell, G.H. et al., "Proteosome-Lipopeptide Vaccines: Enhancement of Immunogenicity for Malaria CS Peptides," *Science*, 240:800-802, 1988.

Lowell, G., "Proteosomes for Improved Nasal, Oral, or Injectable Vaccines," *New Generation Vaccines, 2nd Edition*, Marcel Dekker, Inc. USA, 193-206, 1997.

Lynch, E.C. et al., "Spontaneously Transferred from Whole Cells and Reconstituted from Purified Proteins of *Neisseria gonorrhoeae* and *Neisseria meningitidis*," *Biophysical Journal*, 45(1):104-107, Jan. 1984.

Murphy, B.R. et al., "Dissociation between Serum Neutralizing and Glycoprotein Antibody Responses of Infants and Children Who Received Inactivated Respiratory Syncytial Virus Vaccine," *Journal of Clinical Microbiology*, 24(2):197-202, Aug. 1986.

Murphy, B.R. et al., "An update on approaches to the development of respiratory syncytial virus (RSV) and parainfluenza virus type 3 (PIV3) vaccines," *Virus Research*, 32(1):13-36, 1994.

Navas, L. et al., "Improved outcome of respiratory syncytial virus infection in a high-risk hospitalized population of Canadian children," *The Journal of Pediatrics*, 121(3):348-354, Sep. 1992.

Openshaw, P.J.M. and O'Donnell, D.R., "Asthma and the common cold: can viruses imitate worms?" *Thorax*, 49:101-103, 1994.

Openshaw, P.J.M. et al., "Pulmonary eosinophilic response to respiratory syncytial virus infection in mice sensitized to the major surface of glycoprotein G," *International Immunology*, 4(4):493-500, 1992.

Ryan, E.J. et al., "Immunomodulators and delivery systems for vaccination by mucosal routes," *TRENDS in Biotechnology*, 19(8):293-304, Aug. 2001.

Sparer, T.E. et al., "Eliminating a Region of Respiratory Syncytial Virus Attachment Protein Allows Induction of Protective Immunity without Vaccine-enhanced Lung Eosinophilia," *Journal of Experimental Medicine*, 187(11):1921-1926, Jun. 1, 1998.

Spender, L.C. et al., "Abundant IFN-$\gamma$ production by local T cells in respiratory syncytial virus-induced eosinophilic lung disease," *Journal of General Virology*, 79:1751-1758, 1998.

Srikiatkhachorn, A. et al., "Induction of Th-1 and Th-2 Responses by Respiratory Syncytial Virus Attachment Glycoprotein Is Epitope and Major Histocompatibility Complex Independent," *Journal of Virology*, 73(8):6590-6597, Aug. 1999.

Srikiatkhachorn, A. and Braciale, T.J., "Virus-Specific Memory and Effector T Lymphocytes Exhibit Different Cytokine Responses to Antigens during Experimental Murine Respiratory Syncytial Virus Infection," *Journal of Virology*, 71(1):678-685, Jan. 1997.

Tebbey, P.W. et al., "Atypical Pulmonary Eosinophilia Is Mediated by a Specific Amino Acid Sequence of the Attachment (G) Protein of Respiratory Syncytial Virus," *Journal of Experimental Medicine*, 188(10):1967-1972, Nov. 16, 1998.

Trinchieri, G., "Biology of Natural Killer Cells," *Advances in Immunology*, 47:187-376, 1989.

Varga, S.M. et al., "The Attachment (G) Glycoprotein of Respiratory Syncytial Virus Contains a Single Immunodominant Epitope That Elicits Both Th1 and Th2 $CD4^+$ T Cell Responses," *The Journal of Immunology*, 165:6487-6495, 2000.

Walsh, E.E. and Hruska, J., "Monoclonal Antibodies to Respiratory Syncytial Virus Proteins: Identification of the Fusion Protein," *Journal of Virology*, 47(1):171-177, Jul. 1983.

Waris, M.E. et al., "Respiratory Syncytial Virus Infection in BALB/c Mice Previously Immunized with Formalin-Inactivated Virus Induces Enhanced Pulmonary Inflammatory Response with a Predominant Th2-Like Cytokine Pattern," *Journal of Virology*, 70(5):2852-2860, May 1996.

Moore, et al., "Respiratory syncytial virus disease mechanisms implicated by human, animal model, and in vitro data facilitate vaccine strategies and new therapeutics," *Pharmacology & Therapeutics* 112:405-424 (2006).

* cited by examiner

```
ggggcaaang caaac atg tcc aaa aac aag gac caa cgc acc gct aag aca   51
              Met Ser Lys Asn Lys Asp Gln Arg Thr Ala Lys Thr
                1           5              10 cta gaa aag acc tgg gac act ctc aat cat tta tta ttc ata tca tcg   99
Leu Glu Lys Thr Trp Asp Thr Leu Asn His Leu Leu Phe Ile Ser Ser
         15              20              25 ggc tta tat aag tta aat ctt aaa tct ata gca caa atc aca tta tcc  147
Gly Leu Tyr Lys Leu Asn Leu Lys Ser Ile Ala Gln Ile Thr Leu Ser
         30              35              40 att ctg gca atg ata atc tca act tca ctt ata att aca gcc atc ata  195
Ile Leu Ala Met Ile Ile Ser Thr Ser Leu Ile Ile Thr Ala Ile Ile
 45              50              55              60 ttc ata gcc tcg gca aac cac aaa gtc aca cta aca act gca atc ata  243
Phe Ile Ala Ser Ala Asn His Lys Val Thr Leu Thr Thr Ala Ile Ile
                 65              70              75 caa gat gca aca agc cag atc aag aac aca acc cca aca tac ctc act  291
Gln Asp Ala Thr Ser Gln Ile Lys Asn Thr Thr Pro Thr Tyr Leu Thr
             80              85              90 cag gat cct cag ctt gga atc agc ttc tcc aat ctg tct gaa att aca  339
Gln Asp Pro Gln Leu Gly Ile Ser Phe Ser Asn Leu Ser Glu Ile Thr
         95              100             105 tca caa acc acc acc ata cta gct tca aca aca cca gga gtc aag tca  387
Ser Gln Thr Thr Thr Ile Leu Ala Ser Thr Thr Pro Gly Val Lys Ser
 110             115             120 aac ctg caa ccc aca aca gtc aag act aaa aac aca aca aca acc caa  435
Asn Leu Gln Pro Thr Thr Val Lys Thr Lys Asn Thr Thr Thr Thr Gln
125             130             135             140 aca caa ccc agc aag ccc act aca aaa caa cgc caa aac aaa cca cca  483
Thr Gln Pro Ser Lys Pro Thr Thr Lys Gln Arg Gln Asn Lys Pro Pro
             145             150             155 aac aaa ccc aat aat gat ttt cac ttc gaa gtg ttt aac ttt gta ccc  531
Asn Lys Pro Asn Asn Asp Phe His Phe Glu Val Phe Asn Phe Val Pro
         160             165             170
```

FIG. 3A

```
tgc agc ata tgc agc aac aat cca acc tgc tgg gct atc tgc aaa aga    579
Cys Ser Ile Cys Ser Asn Asn Pro Thr Cys Trp Ala Ile Cys Lys Arg
        175                 180                 185 ata cca gcc aaa aaa cca gga aag aaa acc acc acc aag cct aca aaa    627
Ile Pro Ala Lys Lys Pro Gly Lys Lys Thr Thr Thr Lys Pro Thr Lys
        190                 195                 200 aaa cca acc ttc aag aca acc aaa aaa gat cac aaa cct caa acc act    675
Lys Pro Thr Phe Lys Thr Thr Lys Lys Asp His Lys Pro Gln Thr Thr
205                 210                 215                 220 aaa cca aag gaa gta ccc acc acc aag ccc aca gaa gag cca acc atc    723
Lys Pro Lys Glu Val Pro Thr Thr Lys Pro Thr Glu Glu Pro Thr Ile
                225                 230                 235 aac acc acc aaa aca aac atc ata act aca cta ctc acc aac aac acc    771
Asn Thr Thr Lys Thr Asn Ile Ile Thr Thr Leu Leu Thr Asn Asn Thr
                240                 245                 250 aca gga aat cca aaa ctc aca agt caa atg gaa acc ttc cac tca acc    819
Thr Gly Asn Pro Lys Leu Thr Ser Gln Met Glu Thr Phe His Ser Thr
                255                 260                 265 tcc tcc gaa ggc aat cta agc cct tct caa gtc tcc aca aca tcc gag    867
Ser Ser Glu Gly Asn Leu Ser Pro Ser Gln Val Ser Thr Thr Ser Glu
        270                 275                 280 cac cca tca caa ccc tca tct cca ccc aac aca aca cgc cag tag        912
His Pro Ser Gln Pro Ser Ser Pro Pro Asn Thr Thr Arg Gln *
285                 290                 295 ttatt                                                              917
```

*FIG. 3B*

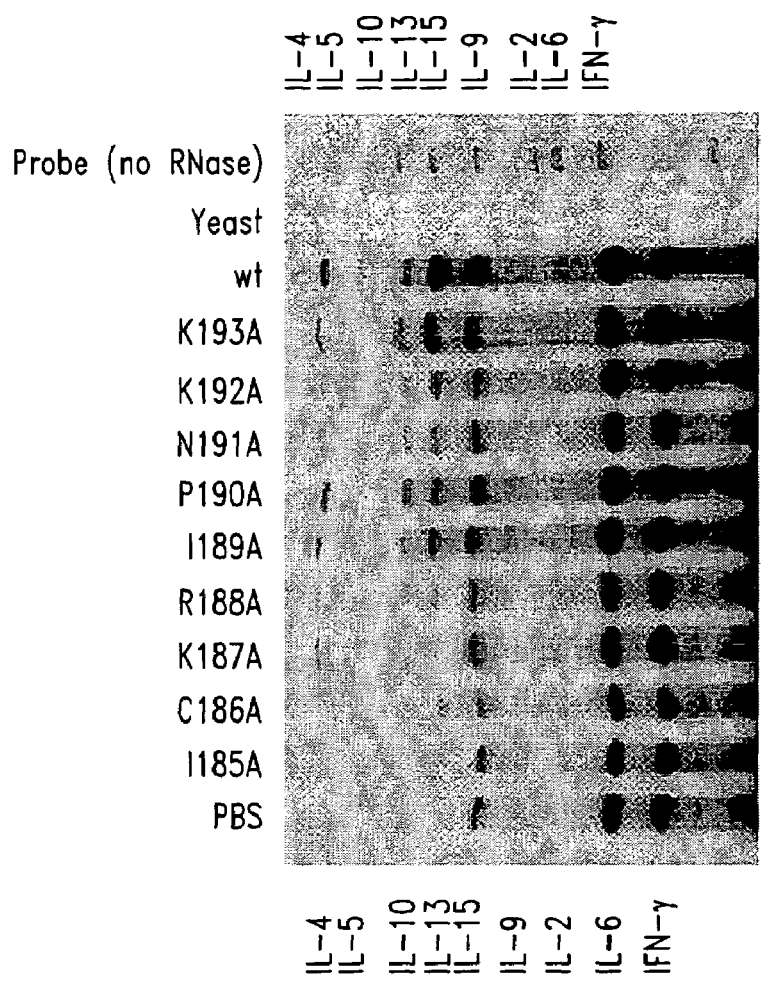 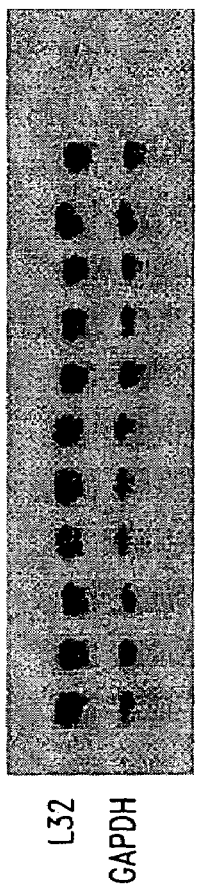
FIG. 4A
FIG. 4B

SUBUNIT VACCINE AGAINST RESPIRATORY SYNCYTIAL VIRUS INFECTION

CROSS-REFERENCE TO RELATED APPLICATIONS

This application claims the benefit of U.S. Provisional Patent Application No. 60/567,586, filed May 3, 2004; and U.S. Provisional Patent Application No. 60/487,804, filed Jul. 15, 2003, in which these provisional applications are incorporated herein by reference in their entireties.

TECHNICAL FIELD

The present invention relates generally to the prevention of infectious disease, and more specifically, to compositions, and the use thereof, comprising one or more respiratory syncytial virus G protein immunogens and fragments or variants thereof capable of eliciting protective immunity without eliciting an immunopathological response or with a reduced immunopathological response (e.g., reducing associated pulmonary pathology).

BACKGROUND

Respiratory syncytial virus (RSV) is the leading cause of lower respiratory tract infection (acute bronchiolitis and pneumonia) in early infancy (Glezen et al., *Amer. J. Dis. Child.* 140:543, 1986; Holberg et al., *Am. J. Epidemiol.* 133:1135, 1991; "Fields Virology", Fields, B. N. et al. Raven Press, N.Y. (1996), particularly, Chapter 44, pp 1313-1351 "Respiratory Syncytial Virus" by Collins, P., McIntosh, K., and Chanock, R. M.). Virtually all children are infected with RSV by the age of two years and 1-2% of all infected children require hospitalization (Holberg et al.; Parrott et al., *Am. J. Epidemiol.* 98:289, 1973). Outbreaks of RSV infection and lower respiratory tract deaths in infants and young children show a strong correlation (Anderson et al., *J. Infect. Dis.* 161:640, 1990), and mortality rates among hospitalized children range between 0.1-1% in the U.S. and Canada (Holberg et al.; Parrott et al.; Navas et al., *J. Pediatr.* 121:348, 1992; Law et al., *Pediatr. Infect. Dis. J.* 12:659, 1993; Ruuskanen and Ogra, *Curr. Prob. Pediatr.* 23:50, 1993). The consequences of RSV infection during infancy range from bronchiolitis or pneumonia to an increased risk for childhood asthma.

Despite intense efforts spanning the past four decades, the search for a safe and effective vaccine against RSV remains elusive. Initial RSV vaccines, including formalin-inactivated and live attenuated virus (reviewed in Murphy et al., *Virus Res.* 32:13, 1994), proved to be disappointingly non-protective and actually led to more severe lung disease in vaccinated children who subsequently acquired natural RSV infection. Immunopathological responses, especially involving inflammatory cell infiltration, may likely underlie RSV-mediated damage to lung tissue. Children who received the formalin-inactivated RSV vaccine developed high levels of virus-specific antibodies, but the antibodies had low levels of neutralizing activity (Murphy et al., *J. Clin. Microbiol.* 24:197, 1986) and failed to protect against infection by RSV (Kim et al., *Am. J. Epidemiol.* 89:422, 1969; Kapikian et al., *Am. J. Epidemiol.* 89:405, 1969; Fulginiti et al., *Am. J. Epidemiol.* 89:435, 1969; Chin et al., *Virol.* 1:1, 1969).

More recent efforts for development of an RSV vaccine have focused on subunit and recombinant methods. RSV has two major surface glycoproteins (designated F and G), which have been examined for use in potential vaccines. The F protein is involved in membrane fusion between the virus and target cell (Walsh and Hruska, *J. Virol.* 47:171, 1983), whereas the G protein is thought to mediate attachment of the virus to a cell receptor (Levine et al., *J. Gen. Virol.* 68:2521, 1987). Both RSV F and G proteins induce strong serum and mucosal immunity, which are important for protection against RSV infection (Glezen et al., 1986; Holberg et al.; Glezen et al., *J. Pediatr.* 98:708, 1981; Lamprecht et al., *J. Infect. Dis.* 134:211, 1976; Hemming et al., *Clin. Microbiol. Rev.* 8:22, 1995). Studies with mice have demonstrated that formalin-inactivated RSV and some G protein-encoding vaccinia recombinants prime for a harmful lung inflammatory response in which eosinophils are a prominent participant (Connors et al., *J. Virol.* 68:5321, 1994; Doherty, *Trends Microbiol.* 2:148, 1994; Waris et al., *J. Virol.* 70:2852, 1996; Graham et al., *J. Immunol.* 151: 2032, 1993; Beasley et al., *Thorax* 43:679, 1988; Openshaw et al., *Int. Immunol.* 4:493, 1992).

Eosinophils and the eosinophil-attractant cytokine IL-5 are considered to be a feature of the so-called type 2 immune response, which has fostered the idea that immunization with RSV antigen has the potential to trigger type 2 responses depending on factors, such as the nature of specific viral immunogens and their route of presentation (Openshaw et al., 1992; Kakuk et al., *J. Infect. Dis.* 167:553, 1993; Openshaw and O'Donnell, *Thorax* 49:101, 1994). Recent work indicates that a portion of the conserved region of the RSV G protein is involved in protective immunity against RSV and in the generation of inflammatory responses, including the induction of eosinophilia (Sparer et al., *J. Expt'l. Med.* 187:1921, 1998; Tebbey et al., *J. Expt'l. Med.* 188:1967, 1998; Srikiatchachom et al., *J. Virol.* 73:6590, 1999; Varga et al., *J. Immunol.* 165:6487, 2000; Huang and Anderson, *Vaccine* 21:2500, 2003).

Hence, a need exists for identifying and developing compositions therapeutically effective against RSV infections, particularly those compositions that can function as a vaccine by eliciting protective immunity without any or with a reduced associated harmful pulmonary inflammation. Furthermore, there is a need for vaccine formulations that can be varied to protect against or treat for infection by different RSV immunogenic subtypes and subgroups. The present invention meets such needs, and further provides other related advantages.

BRIEF SUMMARY OF THE DISCLOSURE

The present invention provides the discovery of therapeutic formulations of respiratory syncytial virus (RSV) immunogens, particularly G protein immunogens useful for eliciting a protective immune response without eliciting an, or with a reduced, immunopathological response.

In one aspect, the invention provides a method for treating or preventing an RSV infection, comprising administering to a subject in need thereof a composition comprising at least one respiratory syncytial virus G protein immunogen or fragment thereof comprising an amino acid sequence that is at least 80% identical to SEQ ID NO:2, wherein said G protein immunogen has an epitope that elicits a protective immune response without eliciting an, or with a reduced, immunopathological response, and a pharmaceutically acceptable carrier, diluent, or excipient, at a dose sufficient to elicit an immune response specific for one or more G protein immunogen or fragments and variants thereof. In a related embodiment, the G protein immunogen is an amino acid sequence comprising or consisting of SEQ ID NO:2. In other embodiments, the invention provides a method for treating or preventing a respiratory syncytial virus infection wherein the G protein immunogen comprises an amino acid sequence selected from SEQ ID NOS:6, 8, 10, 12, 14, 16, 18, 20, 22, 56, 58, 60, 62, 64, 66, 68 or 70. In still more embodiments, the invention provides a method wherein the composition further comprises at least one respiratory syncytial virus F protein immunogen or M protein immunogen, wherein the F protein and M protein immunogens have an epitope that elicits a protective immune response without eliciting an, or with a reduced, immunopathological response, or has at least two G protein immunogens.

In another embodiment, any of the aforementioned G protein immunogens and fragments or variants thereof further comprise a hydrophobic portion or moiety (e.g., to act as an anchor or foot in a lipid environment such as a membrane or proteosome or liposome), particularly when formulated with a proteosome adjuvant delivery vehicle. In yet other embodiments, the hydrophobic moiety comprises an amino acid sequence or a lipid. In certain embodiments, the carrier is a liposome, and in other embodiments the liposome contains *Deinococcus radiodurans* lipids or α-galactosylphosphotidylglycerol alkylamine. In another embodiment, any of the aforementioned compositions further comprise an adjuvant, such as alum, Freund's adjuvant, or a proteosome-based formulation (e.g., a proteosome adjuvant delivery system). Preferably, the adjuvant is suitable for use in humans. In other embodiments, the G protein immunogen or fragment and variants thereof further comprise a second amino acid sequence to form a fusion protein, wherein the second amino acid sequence can be a tag, an enzyme or a combination thereof, such as a polyhistidine, thioredoxin, or both. In certain embodiments, such fusion proteins may further comprise a hydrophobic moiety. In yet other embodiments, any of the aforementioned methods are provided for use when the immunopathological response resulting from or associated with RSV infection is eosinophilia (such as pulmonary eosinophilia) or asthma. In still more embodiments, the invention provides any of the aforementioned methods for use when the infection is due to an RSV of subgroup A, subgroup B, or both subgroup A and subgroup B. In related embodiments, any of the disclosed compositions may be administered in any of the aforementioned methods by a route selected from enteral, parenteral, transdermal, transmucosal, nasal or inhalation.

In another aspect, the invention provides a plurality of antibodies, Th cells, or both produced by a method according to any one of aforementioned methods. In one embodiment, there is provided a method for treating or preventing an RSV infection, comprising administering to a subject in need thereof a composition comprising a pharmaceutically acceptable carrier or a proteosome adjuvant delivery vehicle, and a plurality of antibodies as just described.

In still another aspect, there is provided a composition comprising a respiratory syncytial virus G protein immunogen formulated with a proteosome adjuvant delivery vehicle, wherein said G protein immunogen comprises an amino acid sequence that is at least 80% identical to SEQ ID NO:2 or fragment thereof and wherein said G protein immunogen or fragment thereof has an epitope that elicits a protective immune response without eliciting an immunopathological response or with a reduced immunopathological response. In other embodiments, the composition includes any of the aforementioned G protein immunogens and fragments or variants thereof, fusion proteins, multivalent fusions, cocktail compositions or any combination thereof, and other additives, such as an adjuvant. In some embodiments, the adjuvant is alum, proteosome or protollin.

These and other aspects of the present invention will become evident upon reference to the following detailed description and attached drawings.

BRIEF DESCRIPTION OF THE DRAWINGS

FIGS. 3A and 3B show the nucleic acid sequence (SEQ ID NO:1) and amino acid sequence (SEQ ID NO:2) of RSV group A, Long strain G protein. Shown in bold is an exemplary mutation of an amino acid (N191A, from codon AAC to GCC) to generate a G protein immunogen of the invention, from which fragments and variants thereof can be used as described herein.

FIGS. 4A and 4B show polyacrylamide gel autoradiograms of ribonuclease protection assays (RPAs) of cytokine mRNA in lung tissue. The results illustrate relative levels of cytokine mRNA in lungs of mice assayed four days after RSV challenge, having been previously immunized twice subcutaneously at 14-day intervals with PBS/alum alone, alum-adjuvanted wild type Trx-G128-229 protein, or variant Trx-G128-229 proteins. Panels A and B show different regions of the polyacrylamide gel that exposed radiographic film for 3 days (A) or 1 hour (B).

FIG. 5 shows the detection by ELISA of specific serum IgG antibodies from BALB/c mice immunized with wild type or mutant Trx-(polyHis)-G(1128-229) fusion proteins alone, or adjuvanted with protollin or alum. Mice were immunized three times with a dose of 6 µg or 2 µg of Trx-(polyHis)-G(128-229) fusion proteins. Protollin alone or fusion proteins formulated with protollin were administered intranasally, and alum alone or fusion proteins formulated with alum were administered subcutaneously. Serum samples were obtained after the second immunization (day 35) and two weeks after the third immunization (day 62).

FIG. 6 shows the detection by ELISA of specific bronchoalveolar lavage (BAL) IgA antibodies from BALB/c mice immunized with wild type or mutant Trx-(polyHis)-G (128-229) fusion proteins alone, or adjuvanted with protollin or alum. Mice were immunized three times with a dose of 6 µg or 2 µg of Trx-(polyHis)-G(128-229) fusion proteins. Protollin alone or fusion proteins formulated with protollin were administered intranasally, and alum alone or fusion proteins formulated with alum were administered subcutaneously. BAL samples were collected on day 62 (two weeks after the third immunization).

DETAILED DESCRIPTION

Figure 1:
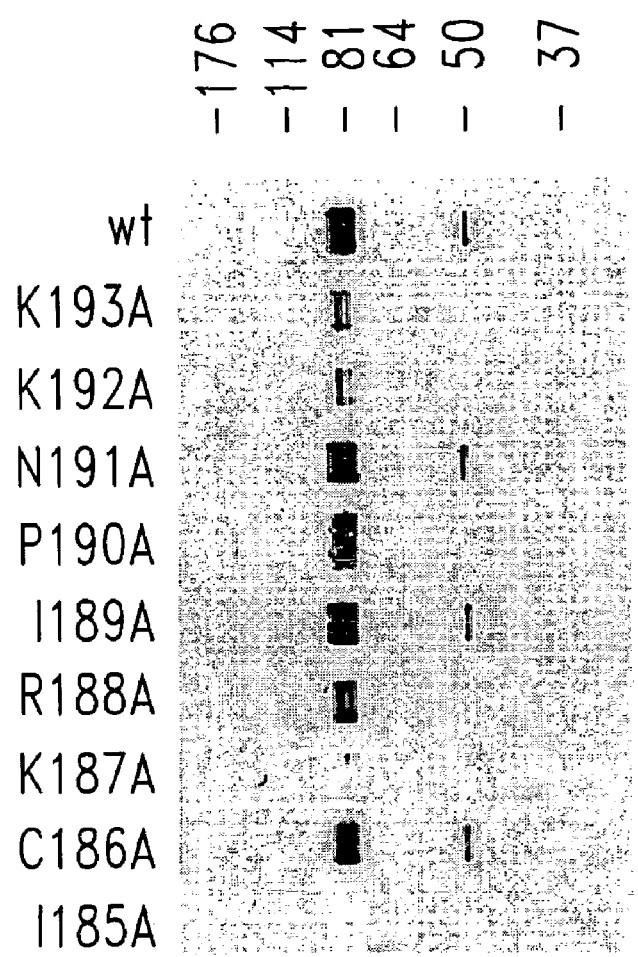
FIG. 1 shows the induction of serum antibodies in mice immunized with wild type or mutant Trx-(polyHis)-G(128-229) proteins in alum and their ability to recognize wild type RSV G protein and the effect of G protein mutations on such induction. Extracts of RSV-infected HEp-2 cells were resolved by SDS-PAGE, transferred to membranes, and probed with pooled sera from each group of mice (mice were immunized twice at 14-day intervals with PBS/alum, or alum-adjuvanted wild type or mutant Trx-(polyHis)-G(128-229) proteins). Shown is an immunoblot of an SDS-PAGE gel illustrating the specificity of mouse sera (1:100 dilution) for the RSV G protein.

As set forth above, the present invention provides compositions and methods for using and making respiratory syncytial virus (RSV) G protein immunogen to treat or prevent respiratory syncytial virus infection. Although protection against RSV re-infection (i.e., challenge) could be obtained with previous vaccines consisting of various forms and immunization modes of the RSV G protein, this was often associated with an unwanted and harmful pulmonary inflammation characterized by pronounced eosinophilia. In addition, immunization of subjects prone to serious RSV disease (e.g., human subjects between the ages of 2 and 7 months of age) may be difficult due to possible immunosuppressive effects of maternally derived serum RSV-neutralizing antibodies or because of the immunological immaturity of the subject. The instant invention, therefore, relates generally to the surprising discovery that certain RSV G protein fragments can be modified to induce or elicit protective immunity against RSV and not induce or have a reduced level of a concomitant immunopathological event that leads to, for example, pulmonary inflammation and aggravated disease upon subsequent infection with RSV. In particular, these G protein immunogens are useful for treating or preventing infections involving RSV. Discussed in more detail below are G protein immunogens or fragments and variants thereof suitable for use within the present invention, as well as representative compositions and therapeutic uses.

In the present description, any concentration range, percentage range, ratio range or integer range is to be understood to include the value of any integer within the recited range and, when appropriate, fractions thereof (such as one tenth and one hundredth of an integer), unless otherwise indicated. As used herein, "about" or "comprising essentially of" mean±15%. The use of the alternative (e.g., "or") should be understood to mean either one, both or any combination thereof of the alternatives. In addition, it should be understood that the individual compounds, or groups of compounds, derived from the various combinations of the sequences, structures, and substituents described herein, are disclosed by the present application to the same extent as if each compound or group of compounds was set forth individually. Thus, selection of particular sequences, structures, or substituents is within the scope of the present invention.

RSV G Protein Immunogens

The present invention is directed generally to immunogenic RSV polypeptide immunogens of G protein or fragments and variants thereof, including fusions to other polypeptides (e.g., a tag, another protein, a hydrophobic amino acid sequence, or any combination thereof) or other modifications (e.g., addition of a lipid or glycosylation). The immunogenic G polypeptides may comprise any portion or fragment of a G protein that has an epitope capable of eliciting a protective immune response against RSV infection without eliciting an immunopathological response or with a reduced immunopathological response. Immunogenic polypeptides of the instant invention may be arranged or combined in a linear form, and each immunogen may or may not be reiterated, wherein the reiteration may occur once or multiple times. In addition, a plurality of different RSV immunogenic polypeptides (e.g., different G protein, F protein, or M protein variants and fragments or variants thereof) can be selected and mixed or combined into a cocktail composition or fused, conjugated or linked to provide a multivalent vaccine for use in eliciting a protective immune response without a harmful associated immune response.

As used herein, "G protein immunogen" or "RSV immunogen" refers to all full length polypeptides, full length variants, fragments and variants thereof, multivalent fusions, cocktail compositions, fusion proteins, or any combination thereof, capable of eliciting a protective immune response against RSV infection without eliciting an immunopathological response or with a reduced immunopathological response, as described herein.

The present invention further provides methods for producing synthetic or recombinant multivalent RSV polypeptide immunogens, including fusion proteins. For example, host cells containing G protein immunogen-encoding nucleic acid expression constructs may be cultured to produce recombinant G protein immunogens and fragments or variants thereof. Also contemplated are methods for treating or preventing RSV infections or eliciting an immune response using a G protein immunogens and fragments or variants thereof, or a combination of polypeptides (including fusion proteins).

As used herein, the phrase "immunopathological response" refers to a condition or disease resulting from an immune reaction, which may or may not have detectable clinical symptoms. Exemplary immunopathological responses include hypersensitivity or asthma. Another exemplary immunopathological response can be an a typical induction of granulocytes in response to type 2 cytokines, such as is found in blood eosinophilia or pulmonary eosinophilia, which can be characteristic of an allergic state or a microbial infection (such as a parasitic infection or a respiratory syncytial virus infection).

By way of background and not wishing to be bound by theory, RSV has a negative-sense, non-segmented, single-stranded RNA genome, which encodes at least 10 viral proteins (G, F, SH, M, M2, N, P, L, NS1, and NS2). RSV has two major surface glycoproteins (designated F and G), which have been examined for use in potential vaccines. The F protein is involved in membrane fusion between the virus and target cell (Walsh and Hruska, *J. Virol.* 47:171, 1983), whereas the G protein is thought to mediate attachment of the virus to a cell receptor (Levine et al., *J. Gen. Virol.* 68:2521, 1987). Both RSV F and G proteins induce strong serum and mucosal immunity, which are important for protection against RSV infection (Glezen et al., 1986; Holberg et al.; Glezen et al., *J. Pediatr.* 98:708, 1981; Lamprecht et al., *J. Infect. Dis.* 134:211, 1976; Hemming et al., *Clin. Microbiol. Rev.* 8:22, 1995). Studies with mice have demonstrated that formalin-inactivated RSV and some G protein-encoding vaccinia recombinants prime for a harmful lung inflammatory response in which eosinophils are a prominent participant (Connors et al., *J. Virol.* 68:5321, 1994; Doherty, *Trends Microbiol.* 2:148, 1994; Waris et al., *J. Virol.* 70:2852, 1996; Graham et al., *J. Immunol.* 151: 2032, 1993; Beasley et al., *Thorax* 43:679, 1988; Openshaw et al., *Int. Immunol.* 4:493, 1992). A surprising result of the instant invention is the identification of G protein immunogens (e.g., variants and mutants of wild-type G protein; an exemplary wild-type G protein is set forth in SEQ ID NO:4, which can be encoded by a nucleic acid sequence as set forth in SEQ ID NO:3) that elicit a protective immune response without eliciting an, or with a reduced, immunopathological response. Thus, in certain embodiments of the instant invention, a respiratory syncytial virus G protein immunogen or fragment thereof that has an epitope that elicits a protective immune response without eliciting an, or with a reduced, immunopathological response is used to prepare compositions useful for treating or preventing RSV infections.

In certain embodiments, the RSV G protein immunogens have at least 50% to 100% amino acid identity to an amino acid sequence of the full length G protein mutant as set forth in SEQ ID NO:2 (from RSV Group A, Long strain; SEQ ID NO:1 is the nucleic acid sequence that encodes amino acid sequence of SEQ ID NO:2), or fragments thereof as set forth in SEQ ID NOS:6, 8, 10, 12, 14, 16, 18, 20, 22, 56, 58, 60, 62, 64, 66, 68 or 70; preferably 60%-99% identity, more preferably 70%-97% identity, and most preferably 80%-95% identity, wherein the G protein immunogen variants retain at least one epitope that elicits a protective immune response against RSV without eliciting an immunopathological response or with a reduced immunopathological response (e.g., eosinophilia). As used herein, "percent identity" or "% identity" is the percentage value returned by comparing the whole of the subject polypeptide, peptide, or variant thereof sequence to a test sequence using a computer implemented algorithm, typically with default parameters.

In one preferred embodiment, a G protein immunogen is a variant of wild-type G protein having a point mutation, wherein an amino acid at, for example, position 191 (Asn) is changed to an Ala (see SEQ ID NO:2 and FIG. 3, also referred to as G protein N 191 A), and in a more preferred embodiment, a G protein immunogen variant is a fragment of full length G protein. For example such a G protein fragment may include from about amino acid 128 to about amino acid 229, wherein the fragment contains the N191A mutation (SEQ ID NO:6). In other embodiments, G protein immunogen variants span amino acids 128 to 229, wherein the variants include double point mutants, such as P190A and N191A (SEQ ID NO:56), or R188A and N191A (SEQ ID NO:58). Other point mutants of use in the instant invention could include those at the Asn at positions 178 (SEQ ID NO:60) and 179 (SEQ ID NO:62), and at the Lys at positions 196 (SEQ ID NO:64), 197 (SEQ ID NO:66), 204 (SEQ ID NO:68), or 205 (SEQ ID NO:70).

The representative G protein immunogen variants described herein include an Ala substitution, but the invention is not so limited and a person of skill in the art would know that other amino acids could be used for substitutions. Moreover, the variant immunogens of the instant invention could be made to include one or more of a variety of mutations, such as point mutations, frameshift mutations, missense mutations, additions, deletions, and the like, or the variants can be a result of modifications, such as by certain chemical substituents, including glycosylation, alkylation, etc. Each of the variants of the instant disclosure preferably is capable of eliciting a protective immune response against RSV without eliciting an immunopathological response or with a reduced immunopathological response (e.g., eosinophilia).

As described herein, preferred fragments of G protein, whether derived from RSV group A or group B, are immunogens that retain at least one epitope that elicits a protective immune response against RSV and elicits a reduced immunopathological response, or is incapable of eliciting an immunopathological response. In certain embodiments, the immunogen fragments or variants thereof (e.g., the N191A mutation) have mutations or variations from wild-type G protein in amino acid sequences that span from about amino acid 120 to about amino acid 300 of SEQ ID NO:2, preferably from about amino acid 125 to about amino acid 250, more preferably from about amino acid 150 to about amino acid 225, and most preferably from about amino acid 165 to about amino acid 195. In one embodiment, the G protein immunogen fragment includes amino acids 128 to 229 and mutations can be found in the range of about amino acids 178 to about 205 of G protein.

Sequence comparisons can be performed using any standard software program, such as BLAST, tBLAST, pBLAST, or MegAlign. Still others include those provided in the Lasergene bioinformatics computing suite, which is produced by DNASTAR® (Madison, Wis.). References for algorithms such as ALIGN or BLAST may be found in, for example, Altschul, *J. Mol. Biol.* 219:555-565, 1991; or Henikoff and Henikoff, *Proc. Natl. Acad. Sci. USA* 89:10915-10919, 1992. BLAST is available at the NCBI website (www.ncbi.nlm.nih.gov/BLAST). Other methods for comparing multiple nucleotide or amino acid sequences by determining optimal alignment are well known to those of skill in the art (see, e.g., Peruski and Peruski, *The Internet and the New Biology: Tools for Genomic and Molecular Research* (ASM Press, Inc. 1997); Wu et al. (eds.), "Information Superhighway and Computer Databases of Nucleic Acids and Proteins," in Methods in Gene Biotechnology, pages 123-151 (CRC Press, Inc. 1997); and Bishop (ed.), Guide to Human Genome Computing, 2nd Edition, Academic Press, Inc., 1998).

As used herein, "similarity" between two peptides or polypeptides is generally determined by comparing the amino acid sequence of one peptide or polypeptide to the amino acid sequence and conserved amino acid substitutes thereto of a second peptide or polypeptide. Fragments or portions of the G protein immunogens or variants thereof of the present description may be employed for producing the corresponding full-length G protein immunogens by peptide synthesis; therefore, the fragments may be employed as intermediates for producing the full-length G protein immunogens. Similarly, fragments or portions of the nucleic acids of the present invention may be used to synthesize full-length nucleic acids of the present disclosure.

As described herein, G protein immunogens and fragments or variants thereof of the instant disclosure have an epitope that elicits a protective immune response without eliciting an immunopathological response or with a reduced immunopathological response. The fragments and variants may be identified using in vivo and in vitro assays known in the art, such as animal immunization studies (e.g., using a mouse or rabbit model) and Western immunoblot analysis, respectively, and combinations thereof. Other examples include plaque reduction assays to assess whether G protein immunogens and fragments or variants thereof of the instant description are capable of eliciting an immune response, particularly a protective (neutralizing) immune response. Briefly, an animal is immunized with one or more G protein immunogens, or composition thereof, by subcutaneous administration, sera is collected from the immunized animals, and then the sera is tested for its ability to inhibit RSV infection of a cell culture monolayer (infection being measured as the number of plaques that form; i.e., "holes" in the monolayer arising from RSV causing cells to lyse) (see, e.g., Example 8). In addition, altered (reduced or enhanced) immunopathological responses can be indirectly identified by, for instance, examining cytokine expression patterns in animals challenged with RSV after immunization with G protein immunogens of the invention. For example, specific cytokine levels can be measured in tissues of interest using a ribonuclease protection assay (RPA) to deduce whether a type 1 or type 2 response is prevalent after immunization with a G protein immunogen of the invention and subsequent challenge with RSV (see Example 9). These and other assays known in the art can be used to identify G protein immunogens and fragments or variants thereof that have an epitope that elicits a protective immune response without eliciting an immunopathological response or with a reduced immunopathological response, according to the instant description.

The RSV G protein polypeptides, fragments thereof, and fusion proteins thereof, as well as corresponding nucleic acids of the present invention, are preferably provided in an isolated form, and in certain preferred embodiments, are purified to homogeneity. As used herein, the term "isolated" means that the material is removed from its original or natural environment. For example, a naturally occurring nucleic acid molecule or polypeptide present in a living animal or cell is not isolated, but the same nucleic acid molecule or polypeptide is isolated when separated from some or all of the co-existing materials in the natural system. The nucleic acid molecules, for example, could be part of a vector and/or such nucleic acids or polypeptides could be part of a composition and still be isolated in that such vector or composition is not part of its natural environment.

The present invention also pertains to RSV G protein immunogens and fragments or variants thereof produced synthetically or recombinantly, and preferably recombinantly. The immunogenic polypeptide components of the immunogens may be synthesized by standard chemical methods, including synthesis by automated procedure. In general, immunogenic peptides are synthesized based on the standard solid-phase Fmoc protection strategy with HATU as the coupling agent. The immunogenic peptide is cleaved from the solid-phase resin with trifluoroacetic acid containing appropriate scavengers, which also deprotects side chain functional groups. Crude immunogenic peptide is further purified using preparative reverse phase chromatography. Other purification methods, such as partition chromatography, gel filtration, gel electrophoresis, or ion-exchange chromatography may be used. Other synthesis techniques known in the art may be employed to produce similar immunogenic peptides, such as the tBoc protection strategy, use of different coupling reagents, and the like. In addition, any naturally occurring amino acid or derivative thereof may be used, including D- or L-amino acids and combinations thereof. In particularly preferred embodiments, a synthetic G protein immunogen of the invention will have an amino acid sequence that is at least 80% identical to SEQ ID NOS:2, 6, 8, 10, 12, 14, 16, 18, 20, 22, 56, 58, 60, 62, 64, 66, 68 or 70.

As described herein, the G protein immunogens and fragments or variants thereof of certain embodiments may be recombinant, wherein a desired G protein immunogen is expressed from a polynucleotide that is operably linked to an expression control sequence (e.g., promoter) in a nucleic acid expression construct. In particularly preferred embodiments, a recombinant G protein immunogen will comprise an amino acid sequence that is at least 80% identical to SEQ ID NO:2. Some preferable recombinant G protein immunogens comprise an amino acid sequence of SEQ ID NO:2 or consist solely of an amino acid sequence as set forth in SEQ ID NO:2. More preferably, a recombinant G protein immunogens and variants thereof comprise an amino acid sequence as set forth in SEQ ID NOS:6, 8, 10, 12, 14, 16, 18, 20, 22, 56, 58, 60, 62, 64, 66, 68 or 70, and more preferably comprise an amino acid sequence as set forth in SEQ ID NO:6, SEQ ID NO:56 or SEQ ID NO:58. In preferred embodiments, recombinant G protein immunogens and fragments or variants thereof have an epitope that elicits a protective immune response without eliciting an, or with a reduced, immunopathological response.

"Nucleic acid" or "nucleic acid molecule" refers to any of deoxyribonucleic acid (DNA), ribonucleic acid (RNA), oligonucleotides, fragments generated by the polymerase chain reaction (PCR), and fragments generated by any of ligation, scission, endonuclease action, and exonuclease action. Nucleic acids may be composed of monomers that are naturally occurring nucleotides (such as deoxyribonucleotides and ribonucleotides), analogs of naturally occurring nucleotides (e.g., α-enantiomeric forms of naturally-occurring nucleotides), or a combination of both. Modified nucleotides can have modifications in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety may be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid" also includes so-called "peptide nucleic acids," which comprise naturally occurring or modified nucleic acid bases attached to a polyamide backbone. Nucleic acids can be either single stranded or double stranded.

Further, an "isolated nucleic acid molecule" refers to a polynucleotide molecule in the form of a separate fragment, or as a component of a larger nucleic acid construct, which has been separated from its source cell (including the chromosome it normally resides in) at least once in a substantially pure form. For example, a DNA molecule that encodes an RSV polypeptide, peptide, or variant thereof, which has been separated from an RSV particle or from a host cell infected with or harboring RSV, is an isolated DNA molecule. Another example of an isolated nucleic acid molecule is a chemically synthesized nucleic acid molecule. Nucleic acid molecules may be comprised of a wide variety of nucleotides, including DNA, cDNA, RNA, nucleotide analogues or some combination thereof. In one embodiment, an isolated nucleic acid molecule comprises a sequence encoding a G protein immunogen or fragment thereof comprising an amino acid sequence that is at least 80% identical to SEQ ID NO:2, wherein said G protein immunogen has an epitope that elicits a protective immune response without eliciting an, or with a reduced, immunopathological response. In another embodiment, an isolated nucleic acid molecule comprises a sequence encoding a G protein immunogen that has an amino acid sequence comprising or consisting of SEQ ID NO:2. In other embodiments, an isolated nucleic acid molecule comprises a sequence encoding a G protein immunogen fragment that comprises an amino acid sequence as set forth in NOS:6, 8, 10, 12, 14, 16, 18, 20, 22, 56, 58, 60, 62, 64, 66, 68 or 70, and more preferably comprises an amino acid sequence as set forth in SEQ ID NO:6, SEQ ID NO:56, or SEQ ID NO:58.

In certain aspects, the invention relates to nucleic acid vectors and constructs that include nucleic acid sequences of the present invention, and in particular to "nucleic acid expression constructs" that include any polynucleotide encoding an RSV polypeptide and fragments or variants thereof as provided above. In another aspect, the instant disclosure pertains to host cells that are genetically engineered with vectors or constructs of the invention, and to the production and use in methods for treating or preventing an RSV infection or eliciting an immune response. The RSV polypeptides and fragments or variants thereof may be expressed in mammalian cells, yeast, bacteria or other cells under the control of appropriate expression control sequences. Cell-free translation systems may also be employed to produce such proteins using RNAs derived from the nucleic acid expression constructs of the present invention. Appropriate cloning and expression vectors for use with prokaryotic and eukaryotic hosts are described, for example, by Sambrook et al., *Molecular Cloning: A Laboratory Manual*, Second Edition, Cold Spring Harbor, N.Y., (1989), and may include plasmids, cosmids, shuttle vectors, viral vectors and vectors comprising a chromosomal origin of replication as disclosed therein.

In one embodiment, a nucleic acid expression construct comprises an expression control sequence operably linked to a polynucleotide encoding a G protein immunogen or fragment thereof comprising an amino acid sequence that is at least 80% identical to SEQ ID NO:2, wherein said G protein immunogen has an epitope that elicits a protective immune response without eliciting an immunopathological response or with a reduced immunopathological response. In certain embodiments, a nucleic acid expression construct comprises an expression control sequence operably linked to a polynucleotide encoding a G protein immunogen that has an amino acid sequence comprising or consisting of SEQ ID NO:2. In other embodiments, a nucleic acid expression construct comprises an expression control sequence operably linked to a polynucleotide encoding a G protein immunogen or fragment thereof comprising an amino acid sequence as set forth in NOS:6, 8, 10, 12, 14, 16, 18, 20, 22, 56, 58, 60, 62, 64, 66, 68 or 70, and more preferably comprises an amino acid sequence as set forth in SEQ ID NO:6, SEQ ID NO:56, or SEQ ID NO:58.

In other embodiments, the nucleic acid expression constructs described herein have an inducible promoter, which may be lac, tac, trc, ara, trp, λ phage, T7 phage, and T5 phage promoter, and more preferably is a T5 phage promoter/lac operator expression control sequence (plasmid pT5) as described in U.S. Patent Ppplication Publication No. 2003/0143685. The "expression control sequence" refers to any sequence sufficient to allow expression of a protein of interest in a host cell, including one or more promoter sequences, enhancer sequences, operator sequences (e.g., lacO), and the like. In certain embodiments, the RSV polypeptide-encoding nucleic acid is in a plasmid, preferably in plasmid pT5, and the host cell is a bacterium, preferably *Escherichia coli*.

Injection of mammals with gene delivery vehicles (e.g., naked DNA) encoding antigens of various pathogens has been shown to result in protective immune responses (Ulmer et al., *Science* 259:1745-9, 1993; Bourne et al., *J Infect. Dis.* 173:800-7, 1996; Hoffman et al., *Vaccine* 12:1529-33, 1994). Since the original description of in vivo expression of foreign proteins from naked DNA injected into muscle tissue (Wolff et al., *Science* 247:1465-8, 1990), there have been several advances in the design and delivery of DNA for purposes of vaccination.

The RSV vaccines described herein are ideally suited for delivery via naked DNA because antibodies ultimately establish protective immunity. For example, within one embodiment, polynucleotide sequences that encode a G protein immunogen or fragment thereof are ligated into plasmids that are specifically engineered for mammalian cell expression (see, e.g., Hartikka et al., *Hum Gene Ther* 7:1205-17, 1996, which contains the promoter/enhancer element from cytomegalovirus early gene, the signal peptide from human tissue plasminogen activator and a terminator element from the bovine growth hormone gene). The RSV polypeptides can be cloned into a plasmid that is used to transfect human cell lines to assure recombinant protein expression. The plasmid may be propagated in bacteria, such as *E. coli*, and purified in quantities sufficient for immunization studies by cesium chloride gradient centrifugation. Animals, such as mice, can be immunized with, for example, 50 μg of an isolated recombinant plasmid in 50 μl saline intramuscularly (i.m.). Booster injections of the same dose may be further given at three and six week intervals after the initial injection.

A wide variety of other gene delivery vehicles can likewise be utilized within the context of the present invention, including viruses, retrotransposons and cosmids. Representative examples include adenoviral vectors (e.g., WO 94/26914, WO 93/9191; Yei et al., *Gene Therapy* 1:192-200, 1994; Kolls et al., *PNAS* 91(1):215-219, 1994; Kass-Eisler et al., *PNAS* 90(24):11498-502, 1993; Guzman et al., *Circulation* 88(6):2838-48, 1993; Guzman et al., *Cir. Res.* 73(6):1202-1207, 1993; Zabner et al., *Cell* 75(2):207-216, 1993; Li et al., *Hum Gene Ther.* 4(4):403-409, 1993; Caillaud et al., *Eur. J. Neurosci.* 5(10):1287-1291, 1993), adeno-associated type 1 ("AAV-1") or adeno-associated type 2 ("AAV-2") vectors (see WO 95/13365; Flotte et al., *PNAS* 90(22):10613-10617, 1993), hepatitis delta vectors, live, attenuated delta viruses, vaccinia vectors and herpes viral vectors (e.g., U.S. Pat. No. 5,288,641), as well as vectors which are disclosed within U.S. Pat. No. 5,166,320. Other representative vectors include retroviral vectors (e.g., EP 0 415 731; WO 90/07936; WO 91/02805; WO 94/03622; WO 93/25698; WO 93/25234; U.S. Pat. No. 5,219,740; WO 93/11230; WO 93/10218). Methods of using such vectors in gene therapy are well known in the art (see, e.g., Larrick, J. W. and Burck, K. L., *Gene Therapy: Application of Molecular Biology*, Elsevier Science Publishing Co., Inc., New York, N.Y., 1991; and Kreigler, M., *Gene Transfer and Expression: A Laboratory Manual*, W.H. Freeman and Company, New York, 1990).

Gene-delivery vehicles may be introduced into a host cell utilizing a vehicle, or by various physical methods. Representative examples of such methods include transformation using calcium phosphate precipitation (Dubensky et al., *PNAS* 81:7529-7533, 1984), direct microinjection of such nucleic acid molecules into intact target cells (Acsadi et al., *Nature* 352:815-818, 1991), and electroporation whereby cells suspended in a conducting solution are subjected to an intense electric field in order to transiently polarize the membrane, allowing entry of the nucleic acid molecules. Other procedures include the use of nucleic acid molecules linked to an inactive adenovirus (Cotton et al., *PNAS* 89:6094, 1990), lipofection (Felgner et al., *Proc. Natl. Acad. Sci. USA* 84:7413-7417, 1989), microprojectile bombardment (Williams et al., *PNAS* 88:2726-2730, 1991), polycation compounds (such as polylysine), receptor specific ligands, liposomes entrapping the nucleic acid molecules, spheroplast fusion whereby *E. coli* containing the nucleic acid molecules are stripped of their outer cell walls and fused to animal cells using polyethylene glycol, viral transduction, (Cline et al., *Pharmac. Ther.* 29:69, 1985; and Friedmann et al., *Science* 244:1275, 1989), and DNA ligand (Wu et al, *J. of Biol. Chem.* 264:16985-16987, 1989), as well as psoralen inactivated viruses such as Sendai or Adenovirus.

Serum from a subject immunized with gene delivery vehicles containing RSV polypeptide immunogens and fragments or variants thereof, and fusions thereof can be assayed for total antibody titer by ELISA using native RSV polypeptides as the antigen. Serum protective antibodies may be assayed as described herein or as known in the art. Protective efficacy of DNA RSV polypeptide vaccines can be determined by, for example, direct animal protection assays (i.e., challenge infection studies) using an RSV serotype that is represented in the pharmaceutical composition or vaccine (i.e., challenge infection studies).

As will be appreciated by those of ordinary skill in the art, an RSV polypeptide-encoding nucleic acid may be a variant of the natural sequence due to, for example, the degeneracy of the genetic code (including homologs or strain variants or other variants). Briefly, such "variants" may result from natural polymorphisms or may be synthesized by recombinant methodology (e.g., to obtain codon optimization for expression in a particular host) or chemical synthesis, and may differ from wild-type polypeptides by one or more amino acid substitutions, insertions, deletions, and the like. Variants encompassing conservative amino acid substitutions include, for example, substitutions of one aliphatic amino acid for another, such as Ile, Val, Leu, or Ala or substitutions of one polar residue for another, such as between Lys and Arg, Glu and Asp, or Gln and Asn. Such substitutions are well known in the art to provide variants having similar physical properties, structural properties, and functional activities, such as for example, the ability to elicit and cross-react with similar antibodies (e.g., antibodies that specifically bind to wild-type G protein). Other variants include nucleic acids sequences that encode G protein immunogen fragments having at least 50% to 100% amino acid identity to SEQ ID NOS:2, 6, 8, 10, 12, 14, 16, 18, 20, 22, 56, 58, 60, 62, 64, 66, 68 or 70. Preferred embodiments are those variants having greater than 90% or 95% identity with the amino acid sequence of SEQ ID NOS:2, 6, 8, 10, 12, 14, 16, 18, 20, 22, 56, 58, 60, 62, 64, 66, 68 or 70.

In certain embodiments, the present invention includes any of the aforementioned degenerate nucleic acid molecules that encode G protein immunogens and fragments or variants thereof comprising an amino acid sequence as set forth in SEQ ID NOS:2, 6, 8, 10, 12, 14, 16, 18, 20, 22, 56, 58, 60, 62, 64, 66, 68 or 70, and that retain functional activity (such as having an epitope that elicits a protective immune response without eliciting an immunopathological response or with a reduced immunopathological response). In another aspect, contemplated are nucleic acid molecules that encode G protein immunogens and fragments or variants thereof having conservative amino acid substitutions or deletions or substitutions, such that the RSV polypeptide variant(s) retain (from wild-type) or have at least one epitope capable of eliciting antibodies specific for one or more RSV strains.

In certain aspects, a nucleic acid sequence may be modified to encode an RSV immunogen or functional variant thereof wherein specific codons of the nucleic acid sequence have been changed to codons that are favored by a particular host and can result in enhanced levels of expression (see, e.g., Haas et al., *Curr. Biol.* 6:315, 1996; Yang et al., *Nucleic Acids Res.* 24:4592, 1996). For example, certain codons of the immunogenic peptides can be optimized, without changing the primary sequence of the peptides, for improved expression in *Escherichia coli*. By way of illustration and not limitation, arginine (Arg) codons of AGG/AGA can be changed to the Arg codons of CGT/CGC. Similarly, AGG/AGA Arg codons can be optimized to CGT/CGC codons. As is known in the art, codons may be optimized for a host in which the G protein immunogens and fragments or variants thereof are to be expressed, including bacteria, fungi, insect cells, plant cells, and mammalian cells. Additionally, codons encoding different amino acids may be changed as well, wherein one or more codons encoding different amino acids may be altered simultaneously as would best suit a particular host (e.g., codons for arginine, glycine, leucine, and serine may all be optimized or any combination thereof). Exemplary nucleic acid sequences with codons optimized for expression in bacteria include sequences as set forth in SEQ ID NOS:23, 25, 27, 29, 31 and 33. These nucleic acid sequences encode G protein immunogen fragment fusion proteins (i.e., fused to thioredoxin or a hexahistidine tag) as set forth in SEQ ID NOS:24, 26, 28, 30, 32 and 34, respectively. Alternatively, codon optimization may result in one or more changes in the primary amino acid sequence, such as a conservative amino acid substitution, addition, deletion, and combinations thereof.

While particular embodiments of isolated nucleic acids encoding RSV immunogens are depicted in SEQ ID NOS:1, 3, 5, 7, 9, 11, 13, 15, 17, 19, 21, 55, 57, 59, 61, 63, 65 67 or 69, within the context of the present disclosure, reference to one or more isolated nucleic acids includes variants of these sequences that are substantially similar in that they encode native or non-native RSV polypeptides with similar structure and similar functional ability to elicit specific antibodies to at least one G protein epitope contained in the RSV polypeptides of SEQ ID NOS:2, 4, 6, 8, 10, 12, 14, 16, 18, 20, 22, 56, 58, 60, 62, 64, 66, 68 or 70. As used herein, the nucleotide sequence is deemed to be "substantially similar" when: (a) the nucleotide sequence is derived from the coding region of an RSV G protein gene (including, for example, portions of the sequence or homologous variations of the sequences discussed herein) and contains a G protein epitope with substantially the same ability to elicit a protective immune response without eliciting an, or with a reduced, immunopathological response; (b) the nucleotide sequence is capable of hybridization to the nucleotide sequences of the present invention under moderate or high stringency; (c) the nucleotide sequences are degenerate (i.e., sequences which code for the same amino acids using a different codon sequences) as a result of the genetic code to the nucleotide sequences defined in (a) or (b); or (d) is a complement of any of the sequences described in (a), (b) or (c).

As used herein, two nucleotide sequences are said to "hybridize" under conditions of a specified stringency when stable hybrids are formed between substantially complementary nucleic acid sequences. Stringency of hybridization refers to a description of the environment under which hybrids are annealed and washed (i.e., conditions under which annealed hybrids remain hybridized or annealed), which typically includes varying ionic strength and temperature. Other factors that might affect hybridization include the probe size and the length of time the hybrids are allowed to form. For example, "high," "medium" and "low" stringency encompass the following conditions or equivalent conditions thereto: high stringency is 0.1×SSPE or SSC, 0.1% SDS, 65° C.; medium stringency is 0.2×SSPE or SSC, 0.1% SDS, 50° C.; and low stringency is 1.0×SSPE or SSC, 0.1% SDS, 50° C. As used herein, the term "high stringency conditions" means that one or more sequences will remain hybridized only if there is at least 95%, and preferably at least 97%, identity between the sequences. In preferred embodiments, the nucleic acid sequences that remain hybridized to a G protein immunogen-encoding nucleic acid molecule encode polypeptides that retain at least one epitope of a G protein immunogen of any one of SEQ ID NOS:2, 6, 8, 10, 12, 14, 16, 18, 20, 22, 56, 58, 60, 62, 64, 66, 68 or 70, and have an epitope with substantially the same ability to elicit a protective immune response without eliciting an immunopathological response or with a reduced immunopathological response.

Methods for producing the RSV polypeptides of the subject invention are also provided wherein any of the nucleic acid molecules and host cells described herein may be used. In a preferred embodiment, a method of producing a G protein immunogen and fragments or variants thereof (having at least one epitope that elicits a protective immune response without eliciting an, or with a reduced, immunopathological response) comprises culturing a host cell containing a nucleic acid expression vector comprising at least one expression control sequence operably linked to a nucleic acid molecule encoding an RSV polypeptide, such as an RSV G protein immunogen and fragment or variant thereof as set forth in any one of SEQ ID NOS:2, 6, 8, 10, 12, 14, 16, 18, 20, 22, 56, 58, 60, 62, 64, 66, 68 or 70, under conditions and for a time sufficient for expression of the polypeptide. In one embodiment, an RSV G protein immunogen and fragment or variant thereof is produced by this method, and more preferably the RSV polypeptides produced comprise an amino acid sequence as set forth in SEQ ID NOS: 2, 6, 8, 10, 12, 14, 16, 18, 20, 22, 56, 58, 60, 62, 64, 66, 68 or 70, and more preferably the RSV polypeptides produced comprise an amino acid sequence as set forth in SEQ ID NO:6, 56, or 58.

In certain embodiments, multivalent vaccines are contemplated. For example, such multivalent compositions may comprise a combination of two or more different G protein immunogens, or a combination of one or more G protein immunogens with one or more other RSV immunogens (such as an F protein or an M protein immunogen). The combination of antigens may be formulated as a cocktail (i.e., a mixture of a plurality of different immunogens), or the combination may be a plurality of different immunogens conjugated, linked or fused together (chemically or recombinantly). In addition, the fused immunogens may have one or more immunogens reiterated at least once within the multivalent fusion protein, which reiteration may occur at the amino-terminal end, the carboxy-terminal end, an internal position of a selected multivalent immunogen polypeptide, at multiple positions, or any combination thereof. For example, such multivalent hybrid RSV immunogens may comprise one or more peptide fragments of the G protein and one or more peptides fragments of an F protein or M protein of RSV, and any combination thereof. In certain embodiments, such multivalent hybrid RSV multivalent hybrid RSV immunogen vaccine compositions may combine immunogenic epitopes from different RSV antigenic groups, for example, immunogens from subgroup A viruses (e.g., Long and A2) or subgroup B viruses (e.g., CH-18537 and 8/60), or immunogens from both subgroup A and B viruses (or any other RSV subgroups that are found to, for example, infect humans).

In some embodiments, the RSV immunogens may be linked by, for example, at least two amino acids encoded by a nucleic acid sequence that is a restriction enzyme recognition site, wherein the restriction sites may be any one or more of BamHI, ClaI, EcoRI, HindIII, KpnI, NcoI, NheI, PmlI, PstI, SalI, XhoI, and the like. Additional amino acid linkers may also be added synthetically, as is known in the art and described herein. Preferably, the additional amino acids do not create any identity in sequence encompassing a five amino acid stretch of a human protein so as to minimize the possibility of eliciting human tissue cross-reactive antibodies. In addition, the hybrid polypeptides of the subject invention may further comprise at least one additional carboxy-terminal amino acid, wherein the additional amino acid is a D- or an L-amino acid. Any of the twenty naturally occurring amino acids or derivatives thereof may be added, such as cysteine, histidine, leucine, and glutamic acid. For example, the addition of cysteine may be useful to attach (e.g., enzymatically or by chemical cross-linking) other constituents, such as a lipid, a carrier protein, a tag, an enzyme, and the like.

As described herein, the invention also provides RSV immunogen fusion proteins comprising a G protein immunogen or fragment thereof fused to an additional functional or non-functional polypeptide sequence that permits, for example, detection, isolation, and purification of the hybrid polypeptide fusion proteins. For instance, an additional functional polypeptide sequence may be a tag sequence, which includes fusion proteins that may in certain embodiments be detected, isolated or purified by protein-protein affinity (e.g., receptor-ligand), metal affinity or charge affinity methods. In certain other embodiments the hybrid polypeptide fusion proteins may be detected by specific protease cleavage of a fusion protein having a sequence that comprises a protease recognition sequence, such that the hybrid polypeptides may be separable from the additional polypeptide sequence. In addition, the hybrid polypeptides may be made synthetically including additional amino acids, a carrier protein, a hydrophobic portion or moiety (e.g., a lipid), or a tag sequence, which may be located at the amino-terminal end, carboxy-terminal end, or at a site internal (non-terminal) of the fusion protein. In particularly preferred embodiments, for example, recombinant RSV immunogens are fused in-frame to a tag, which tag may be any one of alkaline phosphatase, thioredoxin (Trx), β-galactosidase, hexahistidine (6×His), FLAG® epitope tag (DYKDDDDK, SEQ ID NO:71), GST or the like, and any combination thereof.

Preferred embodiments include hybrid polypeptide fusion proteins that facilitate affinity detection and isolation of the hybrid polypeptides, and may include, for example, poly-His or the defined antigenic peptide epitopes described in U.S. Pat. No. 5,011,912 and in Hopp et al., (1988 *Bio/Technology* 6:1204), or the XPRESS™ epitope tag (DLYDDDDK, SEQ ID NO:72; Invitrogen, Carlsbad, Calif.), or thioredoxin. The affinity sequence may be a hexa-histidine tag as supplied by a vector. For example, a pBAD/His (Invitrogen), a pET vector (Invitrogen) or a pQE vector (Qiagen, Valencia, Calif.) can provide a polyhistidine tag for purification of the mature protein fusion from a particular host, such as a bacterium, using a nickel affinity column. Alternatively, the affinity sequence may be added either synthetically or engineered into the primers used to recombinantly generate the nucleic acid sequence (e.g., using the polymerase chain reaction) encoding an immunogenic peptide of RSV. Optionally, any of the aforementioned G protein immunogens and fragments or variants thereof, and fusion proteins thereof, may also have a hydrophobic portion (anchor or foot) that is conjugated, linked or fused (chemically or recombinantly) to the amino-terminal end or carboxy-terminal end. Representative hydrophobic moieties include an amino acid sequence of at least five amino acids, such as MFLLAVFYGG (SEQ ID NO:35) or GGYFVALLF (SEQ ID NO:36), or a lipid.

In certain embodiments, RSV immunogens are fused to a thioredoxin or a polyhistidine tag, which are encoded by a recombinant nucleic acid sequence encoding such a fusion protein. In preferred embodiments, RSV G protein immunogen fragments are fused to a thioredoxin and a polyhistidine tag, which are encoded by a nucleic acid sequence as set forth in SEQ ID NOS: 23 or 25. Exemplary amino acid sequences of RSV G protein immunogen fragments fused to a thioredoxin and a polyhistidine tag are set forth in SEQ ID NOS:24 and 26. In related embodiments, provided are nucleic acid sequences that encode an RSV G protein immunogen fusion protein further comprising a nucleic acid sequence that encodes a hydrophobic moiety or foot linked or fused to the G immunogen fusion protein, as found in the sequences set forth in SEQ ID NOS:27, 29, 31 or 33. Exemplary amino acid sequences of RSV G protein immunogen fragments fused to a thioredoxin and a polyhistidine tag, and further comprising a hydrophobic portion or foot are set forth in SEQ ID NOS:28, 30, 32 and 34. In preferred embodiments, the hydrophobic moiety is an amino acid sequence of MFLLAVFYGG (SEQ ID NO:35) fused to the amino-terminal end of the fusion protein or GGYFVALLF (SEQ ID NO:36) fused to the carboxy-terminal end of the fusion protein.

A fusion protein may comprise a hydrophobic moiety fused to the amino-terminal end or carboxy-terminal end of a G protein immunogen or fragment thereof. Alternatively, fusion protein may comprise a hydrophobic portion fused to a linker (e.g., one or more amino acids, preferably two or four) which in turn is fused to the amino-terminal end or carboxy-terminal end of a G protein immunogen or fragment thereof. In still other embodiments, a fusion protein may comprise a hydrophobic moiety fused to one or more amino acid sequences (e.g., a tag, such as a thioredoxin or a polyhistidine) which in turn is fused to the amino-terminal end of a G protein immunogen or fragment thereof, or a fusion protein may comprise one or more amino acid sequences (e.g., a tag, such as a thioredoxin or a polyhistidine) fused to the amino-terminal end of a G protein immunogen or fragment thereof which in turn is fused to a hydrophobic portion. As will be appreciated by those of skill in the art, a fusion protein of the instant disclosure may be constructed to contain one or more G protein immunogens or fragments and variants thereof, one or more linkers, one or more additional amino acid tag sequences, one or more hydrophobic portions, or any combination thereof.

Therapeutic Formulations and Methods of Use

This description also relates to pharmaceutical compositions that contain one or more RSV immunogens, which may be used to elicit an immune response without the concomitant immunopathological response or at least a reduced immunopathological response. This description further relates to methods for treating and preventing RSV infections by administering to a subject a G protein immunogen or fragment and variants thereof, fusion protein, multivalent immunogen, or a mixture of such immunogens at a dose sufficient to elicit antibodies specific for RSV, as described herein. G protein immunogens or fragments and variants thereof, or a cocktail of such immunogens are preferably part of a pharmaceutically acceptable composition when used in the methods of the present invention.

By way of background, natural or experimental infection of an animal or human subject does not appear to elicit a CD8+ CTL immune response recognizing G protein, while in contrast the F protein does elicit a CD8+ CTL immune response. Accordingly, a G plus F composite RSV antigen vaccine of the instant description is expected to elicit both a CD4+ and a CD8+ protective immune response, without eliciting an, or with a reduced, immunopathological proliferative lymphocyte response, such a response being harmful or otherwise unwanted. Moreover, the use of proteosome technology-based components combined with RSV antigen(s) may influence a shift in the immune response raised to an RSV antigen from a predominantly type 2 response towards a preferential type 1 response (as determined by cytokine profiles known by those of ordinary skill in the art), and thereby eliminating or reducing, in a statistically significant manner, an undesired eosinophilic response, an undesired IgE response or both, following immunization with a vaccine or pharmaceutical composition of the instant description. For example, by combining one or more MHC class I CD8+ immunogenic epitopes of the RSV F protein with one or more CD4+ MHC class II immunogenic epitopes contained in RSV G protein.

As known in the art, the pattern of cytokine expression and CD4+ lymphocyte activation at the time of first exposure to an RSV antigen influences the pattern of immune responses to subsequent exposures. Therefore, along with protection from respiratory disease and eosinophilia, immunogenic compositions of the instant application may prove to be useful in protecting against childhood asthma associated with an RSV infection. In one preferred embodiment, for example, a vaccine of the instant invention is capable of eliciting an immune response that protects from or otherwise moderates the pathological consequences of an RSV infection, while at the same time ablating or otherwise diminishing a subsequent IgE antibody response to common allergens.

In certain embodiments, the invention provides a composition comprising a respiratory syncytial virus G protein immunogen formulated with a proteosome or a liposome, wherein said G protein immunogen comprises an amino acid sequence that is at least 80% identical to SEQ ID NO:2 or fragment thereof and wherein said G protein immunogen or fragment thereof has an epitope that elicits a protective immune response without eliciting an, or with a reduced, immunopathological response. One embodiment is a G protein immunogen comprising an amino acid sequence as set forth in SEQ ID NO:2 or consisting of SEQ ID NO:2. In other preferred embodiments are G protein immunogens that comprise an amino acid sequence selected from SEQ ID NOS:6, 8, 10, 12, 14, 16, 18, 20, 22, 56, 58, 60, 62, 64, 66, 68 or 70, more preferably SEQ ID NO:6, SEQ ID NO:56 or SEQ ID NO:58. Preferably, liposomes formulated to contain one or more RSV immunogens further comprise *Deinococcus radiodurans* lipids or α-galactosylphosphotidylglycerolalkylamine. The addition of such lipids in a liposome can enhance the efficacy of an RSV vaccine composition by increasing protective immunity and suppressing harmful eosinophilia (see, e.g., Huang and Anderson, *Vaccine* 20:1586, 2002).

Respiratory syncytial virus immunogens of the present invention may further include a covalently attached hydrophobic moiety. A hydrophobic moiety may be, for example, an amino acid sequence or a lipid, as disclosed in U.S. Pat. No. 5,726,292. In certain embodiments, the hydrophobic moiety is an amino acid sequence of MFLLAVFYGG (SEQ ID NO:35) fused to the amino-terminal end of an immunogen or GGYFVALLF (SEQ ID NO:36) fused to the carboxy-terminal end of an immunogen. Naturally occurring RSV G protein contains a hydrophobic transmembrane amino acid sequence, which may function as a hydrophobic moiety according to the instant invention. In one embodiment, an RSV composition (e.g., a vaccine composition) of the instant application comprises an RSV G protein immunogen or fragment thereof as described herein formulated with a proteosome or protollin. When formulated with a proteosome or protollin, the G protein immunogens preferably further comprise a hydrophobic moiety, which may be composed of a hydrophobic amino acid sequence or a lipid (as used herein, lipid refers to a solubility characteristic and, therefore, includes alkyls, arylalkls, aryls, fatty acids, glycerides and glyceryl ethers, phospholipids, sphingolipids, long chain alcohols, steroids, vitamins, and the like). In certain embodiments, the G protein immunogens, with or without a hydrophobic moiety, may further contain a second amino acid sequence to form a fusion, wherein the second amino acid sequence is a tag, carrier, enzyme or a combination thereof, as described herein. One preferred RSV vaccine of the instant invention can comprise a non-infectious RSV polypeptide or fragment thereof that is highly immunogenic and capable of immunoneutralizing virus growth. In preferred embodiments of the instant invention, such an RSV subunit vaccine has reduced or no unwanted immunopathological side effects (e.g., eosinophilia or asthma) in a vaccinated subject, such as a human or animal.

The pharmaceutical composition will preferably include at least one of a pharmaceutically acceptable vehicle, carrier, diluent, or excipient, in addition to one or more RSV immunogen or fusion protein thereof and, optionally, other components. For example, pharmaceutically acceptable carriers suitable for use with a composition of a G protein immunogen or fusion protein thereof, or cocktail of two or more G protein immunogens or fusion proteins thereof, or cocktail of G, F, and M immunogens or fusion proteins thereof, may include, for example, a thickening agent, a buffering agent, a solvent, a humectant, a preservative, a chelating agent, an adjuvant, and the like, and combinations thereof.

Exemplary adjuvants include alum (aluminum hydroxide, REHYDRAGEL®), aluminum phosphate, proteosome adjuvant with LPS (protollin) or without LPS (see, e.g., U.S. Pat. Nos. 5,726,292 and 5,985,284, and U.S. Patent Application Publication Nos. 2001/0053368 and US 2003/0044425), virosomes, liposomes with and without Lipid A, Detox (Ribi/Corixa), MF59, or other oil and water emulsions type adjuvants, such as nanoemulsions (see, e.g., U.S. Pat. No. 5,716,637) and submicron emulsions (see, e.g., U.S. Pat. No. 5,961,970), and Freund's complete and incomplete. Pharmaceutically acceptable carriers for therapeutic use are well known in the pharmaceutical art, and as described herein and, for example, in *Remington's Pharmaceutical Sciences*, Mack Publishing Co. (A. R. Gennaro, ed., 18$^{th}$ Edition, 1990) and in *CRC Handbook of Food, Drug, and Cosmetic Excipients*, CRC Press LLC (S.C. Smolinski, ed., 1992).

In certain embodiments, the G protein immunogens and fragments or variants thereof (including fusion proteins and multivalent compositions) are formulated with proteosome. As used herein, "proteosome" or "projuvant" refers to preparations of outer membrane proteins (OMPs, also known as porins) from Gram-negative bacteria, such as *Neisseria* species (see, e.g., Lowell et al., *J. Exp. Med.* 167:658, 1988; Lowell et al., *Science* 240:800, 1988; Lynch et al., *Biophys. J.* 45:104, 1984; Lowell, in "New Generation Vaccines" 2nd ed., Marcel Dekker, Inc., New York, Basil, Hong Kong, page 193, 1997; U.S. Pat. No. 5,726,292; U.S. Pat. No. 4,707,543), which are useful as a carrier or an adjuvant for immunogens, such as bacterial or viral antigens. Proteosomes are hydrophobic and safe for human use, and comparable in size to certain viruses. Proteosomes have the interesting ability to auto-assemble into vesicle or vesicle-like OMP clusters of 20-800 nm, and to noncovalently incorporate, coordinate, associate (e.g., electrostatically or hydrophobically), or otherwise cooperate with protein antigens (Ags), particularly antigens that have a hydrophobic moiety. Any preparation method that results in the outer membrane protein component in vesicular or vesicle-like form, including multi-molecular membranous structures or molten globular-like OMP compositions of one or more OMPs, is included within the definition of Proteosome. Proteosomes may be prepared, for example, as described in the art (see, e.g., U.S. Pat. No. 5,726,292 or 5,985,284).

In certain embodiments, the G protein immunogens and fragments or variants thereof (including fusion proteins and multivalent compositions) are formulated with protollin. As used herein, "proteosome:LPS" or "protollin" (also known as "IVX-908") refers to preparations of projuvant admixed as described herein with at least one kind of liposaccharide to provide an OMP-LPS composition (which can function as an immunostimulatory composition). Thus, the OMP-LPS adjuvant can be comprised of two of the basic components of Protollin, which include (1) an outer membrane protein preparation of Proteosomes (i.e., projuvant) prepared from Gram-negative bacteria, such as *Neisseria meningitides*, and (2) a preparation of one or more liposaccharides. It is also contemplated that components of Protollin may be or include lipids, glycolipids, glycoproteins, small molecules, or the like. The Protollin may be prepared, for example, as described in U.S. Patent Application Publication No. 2003/0044425.

Projuvant is generally used in conjunction with antigens (naturally-occurring or modified) that possess a naturally occurring, modified, or supplementary hydrophobic moiety or portion (also referred to as a "foot" or "anchor"). Protollin (containing exogenously added LPS) can also be used with an antigen that does not contain a hydrophobic foot domain and that can be largely hydrophilic in nature. Protollin can be admixed or combined with an antigen containing a hydrophobic foot, an antigen lacking a hydrophobic foot, or with a combination of antigens having and not having a hydrophobic portion or foot.

As used herein, "liposaccharide" (such as that used in preparing protollin) refers to native (isolated or prepared synthetically with a native structure) or modified lipopolysaccharide or lipooligosaccharide (collectively, also referred to as "LPS") derived from Gram-negative bacteria, such as *Shigella flexneri* or *Plesiomonas shigelloides*, or other Gram-negative bacteria (including *Alcaligenes, Bacteroides, Bordetella, Borrellia, Brucella, Campylobacter, Chlamydia, Citrobacter, Edwardsiella, Ehrlicha, Enterobacter, Escherichia, Francisella, Fusobacterium, Gardnerella, Hemophillus, Helicobacter, Klebsiella, Legionella, Leptospira* (including *Leptospira interrogans*), *Moraxella, Morganella, Neiserria, Pasteurella, Proteus, Providencia*, other *Plesiomonas, Porphyromonas* (including *Porphyromonas gingivalis*), *Prevotella, Pseudomonas, Rickettsia, Salmonella, Serratia*, other *Shigella, Spirillum, Veillonella, Vibrio*, or *Yersinia* species). The liposaccharide may be in a detoxified form (i.e., having the Lipid A core removed) or may be in a form that has not been detoxified. In the instant disclosure, the liposaccharide need not be and preferably is not detoxified.

The two components of an OMP-LPS adjuvant may be formulated at specific initial ratios to optimize interaction between the components resulting in stable association and formulation of the components for use in the preparation of an immunogenic composition of the invention. The process generally involves the mixing of components in a selected detergent solution (e.g., Empigen® BB, Triton® X-100, or Mega-10) and then effecting complexing of the OMP and LPS components while reducing the amount of detergent to a predetermined, preferred concentration, by dialysis or, preferably, by diafiltration/ultrafiltration methodologies. Mixing, co-precipitation, or lyophilization of the two components may also be used to effect an adequate and stable association or formulation. In a preferred embodiment, an immunogenic composition comprises one or more G protein immunogens and an adjuvant, wherein the adjuvant comprises a Projuvant (i.e., Proteosome) and liposaccharide.

In certain embodiments, the final liposaccharide content by weight as a percentage of the total Proteosome protein can be in a range from about 1% to about 500%, more preferably in range from about 10% to about 200%, or in a range from about 30% to about 150%. Another embodiment includes an adjuvant wherein the Proteosomes are prepared from *Neisseria meningitides* and the liposaccharide is prepared from *Shigella flexneri* or *Plesiomonas shigelloides*, and the final liposaccharide content is between 50% to 150% of the total Proteosome protein by weight. In another embodiment, Proteosomes are prepared with endogenous lipooligosaccharide (LOS) content ranging from about 0.5% up to about 5% of total OMP. Another embodiment of the instant invention provides Proteosomes with endogenous liposaccharide in a range from about 12% to about 25%, and in a preferred embodiment between about 15% and about 20% of total OMP. The instant disclosure also provides a composition containing liposaccharide derived from any Gram-negative bacterial species, which may be from the same Gram-negative bacterial species that is the source of Proteosomes or is a different bacterial species.

In certain embodiments, the Proteosome or Protollin to G protein immunogen ratio in the immunogenic composition is greater than 1:1, greater than 2:1, greater than 3:1 or greater than 4:1. The ratio can be as high as 8:1 or higher. In other embodiments, the ratio of Proteosome or Protollin to coronavirus antigen of the immunogenic composition ranges from about 1:1 to about 1:500, preferably the ratio is at least 1:5, at least 1:10, at least 1:20, at least 1:50, or at least 1:100. An advantage of Protollin:G protein immunogen ratios ranging from 1:2 to 1:200 is that the amount of Proteosome-based adjuvant can be reduced dramatically with no significant effect on the ability of a G protein immunogen to elicit an immune response.

As used herein, "pharmaceutically acceptable salt" refers to salts of the compounds of the present invention derived from the combination of such compounds and an organic or inorganic acid (acid addition salts) or an organic or inorganic base (base addition salts). The compounds of the present invention may be used in either the free base or salt forms, with both forms being considered as being within the scope of the present invention.

In addition, the pharmaceutical composition of the instant invention may further include a diluent or excipient, such as water or phosphate buffered saline (PBS). Preferably, a diluent or excipient is PBS with a final phosphate concentration range from about 0.1 mM to about 1 M, more preferably from about 0.5 mM to about 500 mM, even more preferably from about 1 mM to about 50 mM, and most preferably from about 2.5 mM to about 10 mM; and the final salt concentration ranges from about 100 mM to about 200 mM and most preferably from about 125 mM to about 175 mM. Preferably, the final PBS concentration is about 5 mM phosphate and about 150 mM salt (such as NaCl). In certain embodiments, pharmaceutical compositions of the instant disclosure comprising any of the herein described RSV immunogens or cocktails of RSV immunogens are sterile.

The compositions can be sterile either by preparing them under an aseptic environment or they can be terminally sterilized using methods available in the art. Many pharmaceuticals are manufactured to be sterile and this criterion is defined by the USP XXII <1211>. Sterilization in this embodiment may be accomplished by a number of means accepted in the industry and listed in the USP XXII <1211>, including gas sterilization, ionizing radiation or filtration. Sterilization may be maintained by what is termed aseptic processing, defined also in USP XXII <1211>. Acceptable gases used for gas sterilization include ethylene oxide. Acceptable radiation types used for ionizing radiation methods include gamma, for instance from a cobalt 60 source and electron beam. A typical dose of gamma radiation is 2.5 MRad. When appropriate, filtration may be accomplished using a filter with suitable pore size, for example 0.22 µm and of a suitable material, for instance Teflon®. The term "USP" refers to U.S. Pharmacopeia (see www.usp.org; Rockville, Md.).

The present description also pertains to methods for treating or preventing RSV infection, comprising administering to a subject in need thereof a composition comprising at least one respiratory syncytial virus G protein immunogen or fragment thereof comprising an amino acid sequence that is at least 80% identical to SEQ ID NO: 2, wherein the G protein immunogen has an epitope that elicits a protective immune response without eliciting an immunopathological response or with a reduced immunopathological response, and pharmaceutically acceptable carrier, diluent, or excipient, at a dose sufficient to elicit an immune response specific for one or more G protein immunogen or fragment thereof. In certain embodiments, an infection is due to a subgroup A, subgroup B, or both subgroups A and B of RSV. In certain preferred embodiments, the G protein immunogens used in any of the compositions and methods described herein have an amino acid sequence as set forth in SEQ ID NOS:6, 8, 10, 12, 14, 16, 18, 20, 22, 56, 58, 60, 62, 64, 66, 68 or 70, more preferably SEQ ID NO:6, SEQ ID NO:56 or SEQ ID NO:58.

The present description also pertains to methods for reducing the risk of an immunopathological response associated with RSV infection, comprising administering to a subject in need thereof a composition comprising at least one respiratory syncytial virus G protein immunogen or fragment thereof comprising an amino acid sequence that is at least 80% identical to SEQ ID NO: 2, wherein the G protein immunogen has an epitope that elicits a protective immune response without eliciting an immunopathological response or with a reduced immunopathological response, and pharmaceutically acceptable carrier, diluent, or excipient, at a dose sufficient to elicit an immune response specific for one or more G protein immunogen or fragment thereof. In certain embodiments, an infection is due to a subgroup A, subgroup B, or both subgroups A and B of RSV. In certain preferred embodiments, the G protein immunogens used in any of the compositions and methods described herein have an amino acid sequence as set forth in SEQ ID NOS:6, 8, 10, 12, 14, 16, 18, 20, 22, 56, 58, 60, 62, 64, 66, 68 or 70, more preferably SEQ ID NO:6, SEQ ID NO:56 or SEQ ID NO:58.

A subject suitable for treatment with a RSV immunogen formulation may be identified by well-established indicators of risk for developing a disease or well-established hallmarks of an existing disease. For example, indicators of an infection include fever, pus, microorganism positive cultures, inflammation, and the like. Infections that may be treated or prevented with a RSV immunogen vaccine of the subject invention include those caused by or due to RSV, whether the infection is primary, secondary, opportunistic, or the like. Examples of RSV include any subtype, strain, antigenic variant, and the like, of these viruses. For preventative purposes, for example, certain known risk factors for acquiring an RSV infection include premature birth, children with chronic lung disease, children that attend daycare, presence of school-age siblings in the home, exposure to passive smoke in the home, and immunocompromised subjects (adult and children).

Pharmaceutical compositions containing one or more RSV immunogens of the instant description may be in any form that allows the composition to be administered to a subject, such as a human or animal. For example, G protein immunogen, fusion protein, and multivalent compositions of the present description may be prepared and administered as a liquid solution or prepared as a solid form (e.g., lyophilized), which may be administered in solid form, or resuspended in a solution in conjunction with administration. The hybrid polypeptide composition is formulated so as to allow the active ingredients contained therein to be bioavailable upon administration of the composition to a subject or patient or bioavailable via slow release. Compositions that will be administered to a subject or patient take the form of one or more dosage units, where for example, a tablet may be a single dosage unit, and a container of one or more compounds of the invention in aerosol form may hold a plurality of dosage units. In certain preferred embodiments, any of the herein described pharmaceutical compositions comprising a RSV immunogen or cocktail of immunogens of the invention are in a container, preferably in a sterile container.

In one embodiment, the therapeutic composition is administered nasally, wherein cells, such as cells located in the nasal associated lymphoid tissue, can take up an RSV immunogen or cocktail composition of this disclosure. Other typical routes of administration include, without limitation, enteral, parenteral, transdermal/transmucosal, nasal, and inhalation. The term "enteral", as used herein, is a route of administration in which the immunogenic composition is absorbed through the gastrointestinal tract or oral mucosa, including oral, rectal, and sublingual. The term "parenteral", as used herein, describes administration routes that bypass the gastrointestinal tract, including intraarterial, intradermal, intramuscular, intranasal, intraocular, intraperitoneal, intravenous, subcutaneous, submucosal, and intravaginal injection or infusion techniques. The term "transdermal/transmucosal", as used herein, is a route of administration in which the immunogenic composition is administered through or by way of the skin, including topical. The terms "nasal" and "inhalation" encompass techniques of administration in which an immunogenic composition is introduced into the pulmonary tree, including intrapulmonary or transpulmonary. Preferably, the compositions of the present invention are administered nasally.

In another embodiment, the instant compositions comprising at least one respiratory syncytial virus G protein immunogen or fragment thereof can be used in prophylactic methods. For example, an RSV immunogen or cocktail composition of the invention may be administered to a mother during gestation to prevent an RSV infection in the mother and to provide passive immunity to the fetus or newborn. A prophylactic method may comprise administering to a first subject a composition comprising an RSV immunogen and pharmaceutically acceptable carrier, diluent or excipient, followed by administration to a second subject of a second composition comprising at least one respiratory syncytial virus immunogen wherein said first composition comprises a different RSV immunogen than that administered to the second subject and the second composition comprises at least one respiratory syncytial virus G protein immunogen or fragment thereof comprising an amino acid sequence that is at least 80% identical to SEQ ID NO: 2 and a pharmaceutically acceptable carrier, diluent or excipient, wherein the G protein immunogen has an epitope that elicits a protective immune response without eliciting an, or with a reduced, immunopathological response. In certain embodiments, the G protein immunogens for prophylactic use can have an amino acid sequence as set forth in SEQ ID NOS:6, 8, 10, 12, 14, 16, 18, 20, 22, 56, 58, 60, 62, 64, 66, 68 or 70, more preferably SEQ ID NO:6, SEQ ID NO:56 or SEQ ID NO:58.

A representative first subject can be a mother during gestation and a representative second subject can be the mother's newborn child. Each composition is provided at a dose sufficient to elicit an immune response specific for one or more RSV immunogen (such as G protein immunogens described herein). For instance, not wishing to be bound by theory, G protein immunogens and compositions thereof can be administered systemically (e.g., intravenously) to the mother, which would elicit IgG antibodies similar to the antibodies the mother already has due to exposure to RSV. The newborn child can then be immunized via the mucosa (e.g., intranasally), which would elicit secretory IgA antibodies—hence, the G protein immunogens administered via the mucosa will not be detected by the systemic maternal (IgG) antibodies the child inherited because the IgG antibodies will not be at the mucosal interface. That is, the maternally inherited antibodies will not adversely affect the IgA response elicited by intranasal immunization of the child. In certain embodiments, the administered compositions may prevent an infection due to a subgroup A, subgroup B, or both subgroups A and B of RSV. A subject suitable for treatment with a RSV immunogen formulation may be identified by well-established indicators of risk for developing a disease or well-established hallmarks of an existing disease as described herein and is known in the art. Infections that may be treated with a RSV immunogen of the subject invention include those caused by or due to RSV, whether the infection is primary, secondary, opportunistic, or the like. Examples of RSV include any strain, subtype, antigenic variant, and the like of these viruses.

The invention further provides a plurality of antibodies produced by the method for preventing a RSV infection that comprises administering to a subject a composition of the subject invention at a dose sufficient to elicit antibodies specific for one or more RSV immunogen wherein said G protein immunogen has an epitope that elicits a protective immune response without eliciting an, or with a reduced, immunopathological response. In one embodiment, the antibodies comprise at least one antibody specific for a subgroup A RSV, or a subgroup B RSV, or for both subgroup A and B RSVs. In another embodiment, a method for treating or preventing a RSV infection comprises administering to a subject a composition comprising a pharmaceutically acceptable carrier, with or without an adjuvant, and a plurality of antibodies of the subject invention.

In addition, a subject at risk for an RSV infection can have a plurality of antibodies according to this description administered before, simultaneous with, or after administration of a composition comprising at least one different respiratory syncytial virus G protein immunogen or fragment thereof comprising an amino acid sequence that is at least 80% identical to SEQ ID NO: 2 and pharmaceutically acceptable carrier, diluent or excipient, according to the instant description. In certain preferred embodiments, the G protein immunogens used in any of the compositions and methods described herein have an amino acid sequence as set forth in SEQ ID NOS:6, 8, 10, 12, 14, 16, 18, 20, 22, 56, 58, 60, 62, 64, 66, 68 or 70, more preferably SEQ ID NO:6, SEQ ID NO:56 or SEQ ID NO:58. In some embodiments, antibodies specific for one or more RSV immunogens can be provided passively, while the subject is vaccinated to actively elicit antibodies against one or more different RSV immunogens.

In another aspect, the RSV G protein immunogens and fragments, variants hereof of the present invention are utilized to elicit antibodies specific for at least one epitope present on the G protein immunogens and fragments or variants thereof provided herein. Accordingly, the present invention also provides such antibodies. In preferred embodiments the antibodies bind to specific protective epitopes present on an RSV G protein. Within the context of the present invention, the term "antibodies" includes polyclonal antibodies, monospecific antibodies, monoclonal antibodies, anti-idiotypic antibodies, fragments thereof such as F(ab')$_2$ and Fab fragments, and recombinantly or synthetically produced antibodies. Such antibodies incorporate the variable regions that permit a monoclonal antibody to specifically bind, which means an antibody is able to selectively bind to a peptide or polypeptide from an RSV G protein from subtype A or B. "Specific for" refers to the ability of a protein (e.g., an antibody) to selectively bind a polypeptide or peptide encoded by a nucleic acid molecule encoding a from an RSV G protein from subtype A or B, or a synthesized RSV G protein from subtype A or B, of this invention. Association or "binding" of an antibody to a specific antigen generally involve electrostatic interactions, hydrogen bonding, Van der Waals interactions, and hydrophobic interactions. Any one of these or any combination thereof can play a role in the binding between an antibody and its antigen. Such an antibody generally associates with an antigen, such as a G protein immunogen, with an affinity constant ($K_a$) of at least $10^4$, preferably at least $10^5$, more preferably at least $10^6$, still more preferably at least $10^7$ and most preferably at least $10^8$. Affinity constants may be determined by one of ordinary skill in the art using well-known techniques (see Scatchard, *Ann. N.Y. Acad. Sci.* 51:660-672, 1949). The affinity of a monoclonal antibody or antibody can be readily determined by one of ordinary skill in the art (see Scatchard, *Ann. N.Y. Acad. Sci.* 51:660-672, 1949).

In addition, the term "antibody," as used herein, includes naturally occurring antibodies as well as non-naturally occurring antibodies, including, for example, single chain antibodies, chimeric, bifunctional and humanized antibodies, fully human antibodies, as well as antigen-binding fragments thereof. Such non-naturally occurring antibodies may be constructed using solid phase peptide synthesis, may be produced recombinantly, or may be obtained, for example, by screening combinatorial libraries consisting of variable heavy chains and variable light chains (Huse et al., *Science* 246:1275-1281 (1989)). These and other methods of making, for example, chimeric, humanized, CDR-grafted, single chain, and bifunctional antibodies are well known in the art (Winter and Harris, *Immunol. Today* 14:243, 1993; Ward et al., *Nature* 341:544, 1989; Harlow and Lane, *Antibodies: A Laboratory Manual*, Cold Spring Harbor Laboratory, New York, 1992; Borrabeck, *Antibody Engineering,* 2d ed., Oxford Univ. Press, 1995; Hilyard et al., *Protein Engineering: A practical approach*, IRL Press, 1992).

Polyclonal antibodies can be readily generated by one of ordinary skill in the art from a variety of warm-blooded animals, including horses, cows, goats, sheep, dogs, chickens, turkeys, rabbits, mice, or rats. Briefly, the desired G protein immunogen or fragment thereof, or mixtures of RSV immunogens, or variants thereof are administered to immunize an animal through parenteral, intraperitoneal, intramuscular, intraocular, or subcutaneous injections. The immunogenicity of the hybrid polypeptide of interest may be increased through the use of an adjuvant, such as alum and Freund's complete or incomplete adjuvant. Following several booster immunizations over a period of weeks, small samples of serum are collected and tested for reactivity to the desired immunogen. Once the titer of the animal has reached a plateau in terms of its reactivity to a G protein immunogen of the invention, larger quantities of polyclonal immune sera may be readily obtained either by weekly bleedings or by exsanguinating the animal.

The RSV immunogens of the instant invention can be easily identified using in vitro and in vivo assays known in the art and as described herein. Representative assays are described in the Examples. Similarly, several assays are available as described herein to examine the activity of the antibodies elicited by the RSV immunogens of the subject invention.

All of the U.S. patents, U.S. patent application publications, U.S. patent applications, foreign patents, foreign patent applications and non-patent publications referred to in this specification or listed in the Application Data Sheet, are incorporated herein by reference, in their entirety. The invention having been described, the following examples are intended to illustrate, and not limit, the invention.

EXAMPLES

Example 1

Preparation of Proteosomes

Immunogens of the instant invention may be formulated with proteosomes by way of non-covalent interactions to form a vaccine composition capable of eliciting a protective immune response in an immunized human or animal subject. Proteosomes of the instant application are mucosal adjuvant delivery vehicles comprising outer membrane proteins purified from, for example, Group B type 2 *Neisseria meningitides*. The use of proteosomes for the formulation of vaccines has been reviewed by Lowell, G. H., in "New Generation Vaccines $2^{nd}$ ed., Marcel Dekker, Inc., New York, Basil, Hong Kong (1997) pages 193-206. Proteosomes of the instant invention may be prepared by extraction of phenol-killed bacterial paste with a solution of 6% Empigen BB (EBB) (Albright and Wilson, Whithaven, UK) in 1 M calcium chloride followed by precipitation with ethanol, solubilization in 1% EBB-Tris/EDTA-saline and then precipitation with ammonium sulfate. The precipitates are re-solubilized in the 1% EBB buffer, dialyzed, and stored in 0.1% EBB at −70° C. Alternative processes may be used in the preparation of proteosomes, for example, proteosomes may be prepared by omitting the ammonium sulfate precipitation step to shorten the process. Preparation of proteosomes are disclosed in U.S. Patent Application Publication No. 2001/0053368 and in U.S. Pat. No. 6,476,201 B1.

Example 2

Preparation of Liposomes

Immunogens of the instant invention may be combined non-covalently with liposomes as a vaccine composition capable of eliciting a protective immune response in an immunized human or animal subject. Immunogens may be encapsulated with multilamellar liposomes according to procedures known to those of ordinary skill in the art using, for example, a dehydration coupled reconstitution method (Kirby and Gregoriadis, *BioTechnology* 2:979, 1984). Briefly, liposomes are prepared by sonication of dioleoylphosphatidyl choline (DOPC/cholesterol, Sigma Chemical Co., St. Louis, Mo.; 5:1, W/W) at a final lipid concentration of 30 mg/ml in PBS or generating liposomes using *Deinococcus radiodurans* lipids or α-galactosylphosphotidylglycerolalkylamine as desribed in Huang and Anderson, *Vaccine* 20:1586, 2002, in the presence or absence of antigen. The liposome, with or without one or more immunogens, are lyophilized and resuspended in sterile water. Immunogen that is not incorporated into liposomes may be removed by repeated washing and centrigugation (e.g., microcentrifugation for 1 min at 13,200 rpm) of the liposomes in phosphate buffered saline (PBS). The protein content of washed liposomes, with and without immunogen, is determined by, for example, quantitative silver-stained SDS-PAGE using calibrated amounts known protein standards, such as serum albumin. The protein content of the liposomes is determined and adjusted as desired, for example, the protein content may be adjusted to 0.3 mg per mg of lipid (as liposomes) per ml.

In some cases, to evaluate the manner in which the protein antigen interacts with a liposome, liposomes containing aliquots of G protein immunogens and fragments thereof (wild type or mutant) may be incubated for 1 hour at 37° C. in PBS with proteinase K (Gibco/BRL) at 1.0, 0.1 and 0.01 µg/ml. Some incubations may also contain 1% Triton X-100 to disrupt liposomes, thereby allowing complete access of the proteinase K to the proteins, fusion proteins, or polypeptide fragments thereof. Incubations are terminated and samples analyzed by SDS-PAGE and silver staining. Such procedures may be used to determine the extent of liposome encapsulation of the immunogen (e.g., one or more viral proteins) preparation.

Example 3

Preparation of Nucleic Acids and Expression Constructs Encoding G Protein Immunogens and Fragments Thereof G protein encoding nucleic acid sequences from the RSV (Long strain) corresponding to amino acids 128-229, as well as, for example, mutant 128-229 sequences were amplified from viral RNA by RT-PCR, and the resultant PCR products cloned into the EcoRI and XhoI sites of a pET-32-LIC bacterial expression plasmid (Novagen, Madison, Wis.). Site-directed mutagenesis of the RSV G128-229 protein sequence was performed according to the Stratagene QuikChange® site-directed mutagenesis protocol. Briefly, PCR was performed on template pET-32-LIC-G128-229 DNA (G128-229 sequence cloned into EcoRI and XhoI sites).

In these experiments, the primer pairs designed for mutagenesis were as follows:

```
CCTGCTGGGCTGCCTGCAAAAGAATACCAAACAAAAAACCAGG    (SEQ ID NO:37)

and

CCTGGTTTTTTGTTTGGTATTCTTTTGCAGGCAGCCCAGC AGG   (SEQ ID NO:38)

(for the G128-229, I185A mutant);

CTGCTGGGCTATCGCCAAAAGAATACCAAACAAAAAACCAGG     (SEQ ID NO:39)

and

CCTGGTTTTTTGTTTGGTATTCTTTTGGCGATAGCCCAGCAG     (SEQ ID NO:40)

(for the G128-229, C186A mutant);

CTGCTGGGCTATCTGCGCAAGAATACCAAACAAAAAACCAGG     (SEQ ID NO:41)

and

CCTGGTTTTTTGTTTGGTATTCTTGCGCAGATAGCCCAGCAG     (SEQ ID NO:42)

(for the G128-229, K187A mutant);

CTGCTGGGCTATCTGCAAAGCAATACCAAACAAAAAACCAGG     (SEQ ID NO:43)

and

CCTGGTTTTTTGTTTGGTATTGCTTTGCAGATAGCCCAGCAG     (SEQ ID NO:44)

(for the G128-229, R188A mutant);

CTGCTGGGCTATCTGCAAAAGAGCACCAAACAAAAAACCAGG     (SEQ ID NO:45)

and
```

-continued

```
CCTGGTTTTTGTTTGGTGCTCTTTTGCAGATAGCCCAGCAG    (SEQ ID NO:46)

(for the G128-229, I189A mutant);

CTGCTGGGCTATCTGCAAAAGAATAGCAAACAAAAAACCAGG   (SEQ ID NO:47)

and

CCTGGTTTTTGTTTGCTATTCTTTTGCAGATAGCCCAGCAG    (SEQ ID NO:48)

(for the G128-229, P190A mutant);

CTGCAAAAGAATACCAGCCAAAAAACCAGGAAAGAAAACCACC  (SEQ ID NO:49)

and

GGTGGTTTTCTTTCCTGGTTTTTGGCTGGTATTCTTTTGCAG   (SEQ ID NO:50)

(for the G128-229, N191A mutant);

CTGGGCTATCTGCAAAAGAATACCAAACGCAAAACCAGGAAAG  (SEQ ID NO:51)

and

CTTTCCTGGTTTTGCGTTTGGTATTCTTTTGCAGATAGCCCAG  (SEQ ID NO:52)

(for the G128-229, K192A mutant);

GCAAAAGAATACCAAACAAAGCACCAGGAAAGAAAACCACCAC  (SEQ ID NO:53)

and

GTGGTGGTTTTCTTTCCTGGTGCTTTGTTTGGTATTCTTTTGC  (SEQ ID NO:54)

(for the G128-229, K193A mutant).
```

Thioredoxin (Trx)-fusion proteins containing wild type, and the above mutant RSV G protein fragments were prepared as described in Example 4.

Example 4

Production of G Protein Immunogens and Fragments Thereof

RSV G protein immunogens can be prepared as pharmaceutical compositions by mixing with a pharmaceutically acceptable carrier, excipient or diluent. For example, the RSV G protein sequences described herein and encoded by nucleic acid contained in modified pET-32-LIC plasmids were expressed as thioredoxin (Trx)-fusion proteins in transformed *E. coli* BL21/DE3 cells following induction with IPTG. All Trx-fusion proteins were recovered from transformed cell pellets by extraction with 8M urea, followed by affinity purification using TALON® (Clontech, Palo Alto, Calif.) and dialysis against PBS. Purified Trx-G128-229 polypeptides were freed from contaminating endotoxin by treatment with polymyxin B beads (BioRad, Mississauga, ON, Canada). Details and modifications of this procedure are well known to those of ordinary skill in the art. Upon use for immunization, immunogens can be further combined or admixed with an adjuvant, such as alum or a proteosome-based adjuvant.

Example 5

Preparation of RSV

RSV (Long strain) was obtained from the American Type Culture Collection and propagated on HEp-2 cells cultured in Earle's Minimal Essential Medium (MEM) containing penicillin G (100 U/ml) and streptomycin sulfate (100 ug/ml) and supplemented with 1% serum (fetal calf serum/calf serum, 1:3). Cells and virus were verified negative for mycoplama contamination by PCR assay (American Type Culture Collection). As described in this Example, confluent monolayer cultures of HEp-2 cells were inoculated with RSV (Long strain) at a multiplicity of infection (MOI) of 1, adsorbed 90 min at 4° C., washed and incubated at 37° C. in RPMI-1640 medium (Sigma, St. Louis, Mo.) supplemented with 1% fetal calf serum (Sigma, St. Louis, Mo.). Cultures were harvested after 24-30 h, at which time the cell monolayers were almost completely fused; virus was released from cells by disruption with a hand-held Teflon scraper (Gibco-BRL) and cellular debris was removed by microcentrifugation for 5 min at 13,000×g. The supernatant was used as the source of virus for mouse challenge studies (see Example 6).

Example 6

Mouse Immunization

All immunizations were performed using BALB/c mice (Charles River, Ste. Constance, QC, Canada), which were anaesthetized with ketamine (2.3 mg/mouse; Bimeda-MTC Pharmaceuticals, Cambridge, ON, Canada) and xylazine (0.5 mg/mouse; Bayer, Toronto, ON, Canada). For vaccine/challenge experiments, groups of seven to nine BALB/c mice (6-8 wks old) were immunized twice subcutaneously, at 14-day intervals, with PBS/alum, Trx-G128-229, or mutant Trx-G128-229 proteins, in PBS/alum (10 μg protein in a volume of 50 μl). Fourteen days after the second dose, mice were challenged intranasally with RSV ($2\times10^6$ pfU in 50 μl). Mice were sacrificed using sodium pentobarbital four days later and assayed for lung virus titers and leukocyte infiltration in bronchoalveolar fluids according to procedures well known to a person of ordinary skill in the art.

Immunoblot analysis demonstrated that serum antibodies raised against amino acids 128-229 of RSV G protein were capable of specifically recognizing RSV G protein in mice immunized with wild type or mutant Trx-G128-229 proteins (FIG. 1). Extracts of RSV-infected HEp-2 cells were resolved by SDS-PAGE, and transferred to membranes (e.g., polyvinyldene difluoride (PVDF) membranes). Membranes containing transferred protein were blocked (to prevent non-specific interactions) with 4% skim milk and 0.5% casein (Hammerstein grade) in TBST (0.8% NaCl, 0.1% Tween-20, 20 mM Tris, pH 7.6) by overnight incubation at room temperature. Blocked membranes were then incubated with serum samples, washed with TBST, followed by 1 hour incubation with horse-radish peroxidase (HRP)-conjugated goat antimouse antibody, and then signal was then detected using diaminobezidine (DAB; 1 mg/ml, 0.03% NiCl2 and 0.1% H2O2, according to procedures known in the art. A strong G protein-specific antibody (IgG) response was observed with wild type and N191A mutant proteins. Very little RSV G protein antibody specific signal was observed in sera obtained from mice immunized with I185A or K187A mutant RSV G polypeptide fusion proteins. The remaining Trx-G128-229 mutant proteins induced intermediate levels of RSV G-specific antibodies (FIG. 1).

Example 7

RSV Challenge of Immunized Mice

Figure 2A:
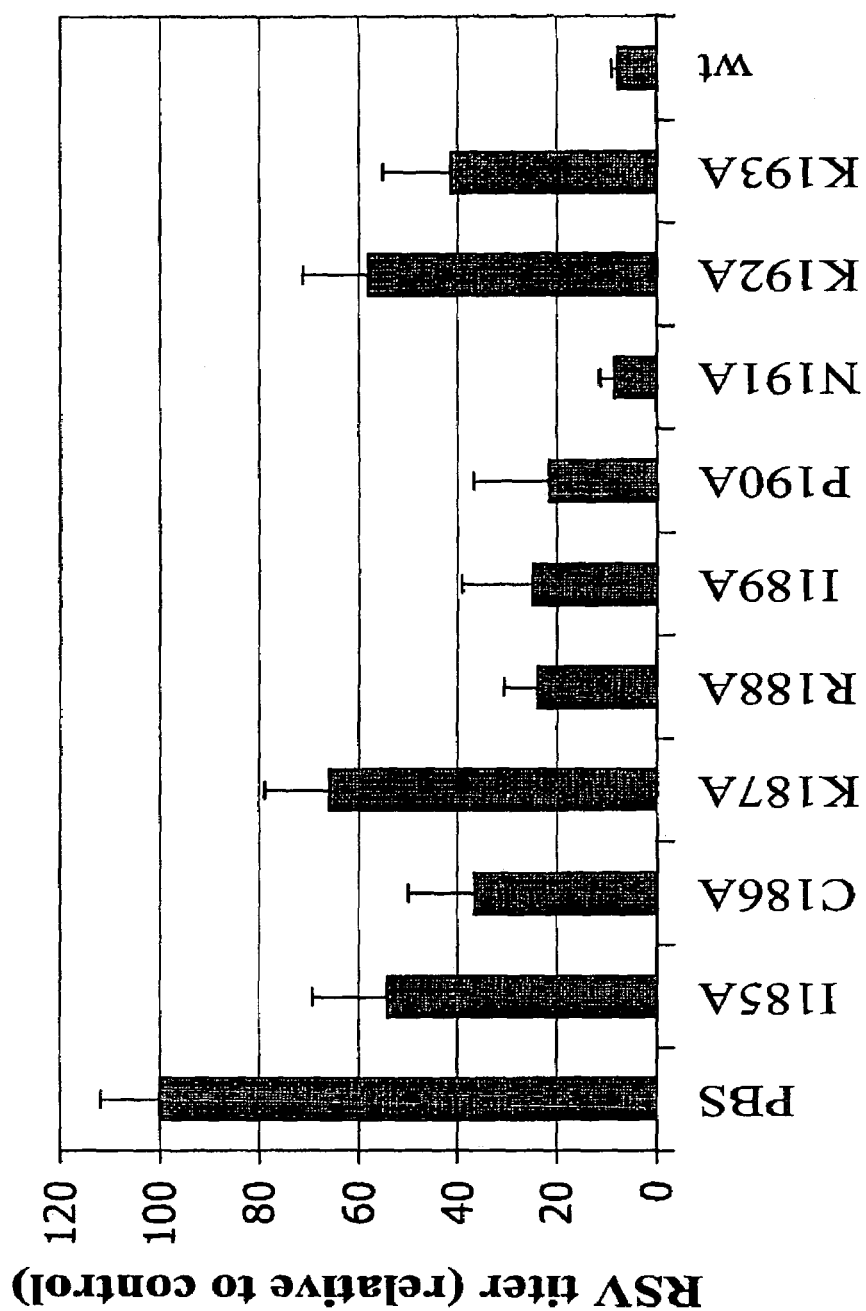
FIGS. 2A and 2B show how G protein variants affect protective immunity (A) and eosinophilic infiltration in bronchoalveolar fluids (B) in immunized mice challenged with RSV. Mice were immunized twice subcutaneously at 14-day intervals with PBS/alum or wild type or mutant Trx-G128-229 proteins in alum, followed by RSV challenge. RSV titers in lung homogenates, as well as bronchoalveolar lavage eosinophils (as % of total cells) were determined four days after RSV challenge. Results are shown as means±SD.
Figure 2B:
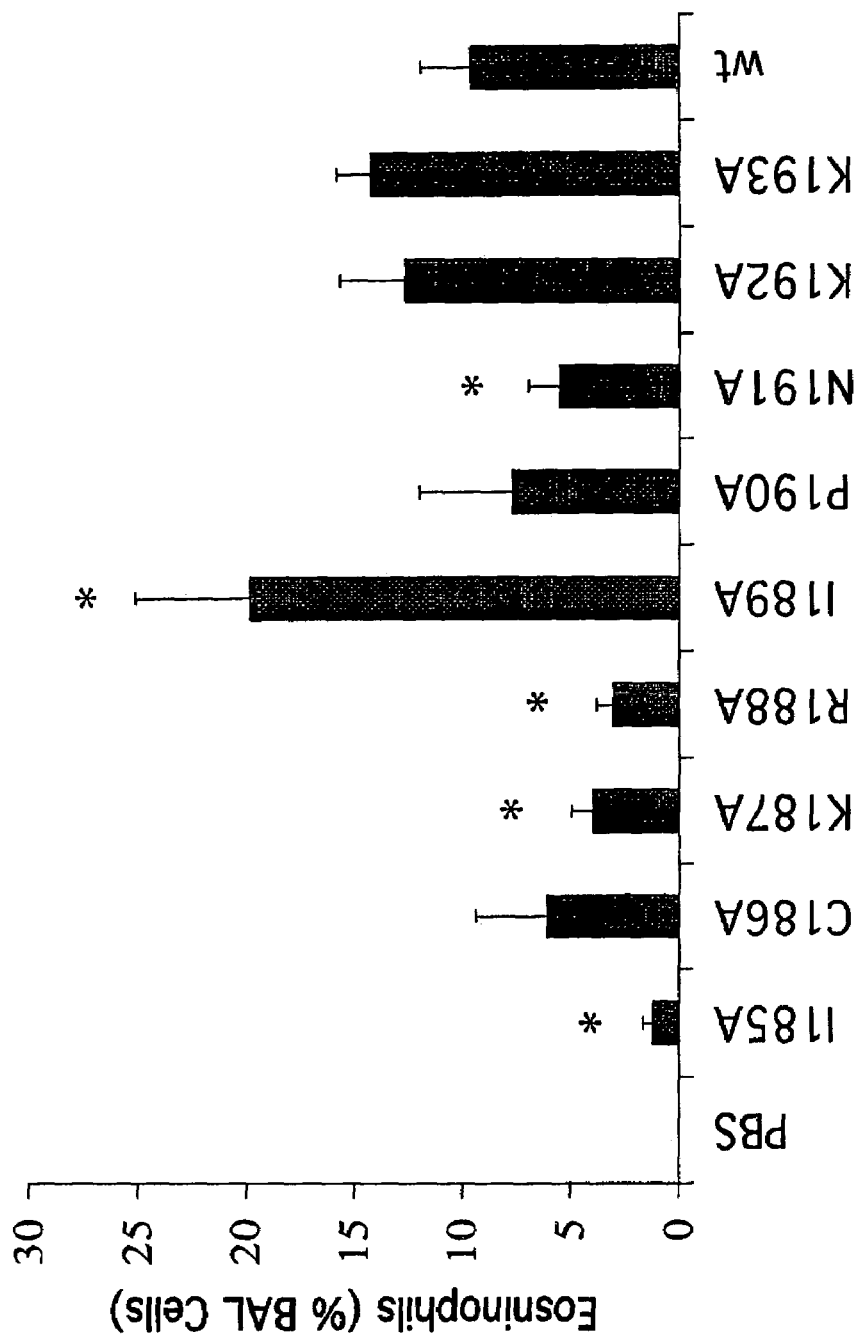

In these experiments, mice were immunized (as described in Example 6) with either wild type Trx-G128-229 or one of each of the 9 mutants and then challenged with RSV. Induction of eosinophilia was determined according to procedures described in Mader et al. *Vaccine* 18:1110, 2000. As shown in FIG. 2A, wild type Trx-G128-229 and various single mutants protected mice against RSV challenge to varying degrees. Comparatively, the N191 A mutated Trx-G128-229 provided better protection than did mutants P190A, R188A and I189A. The remaining Trx-G128-229 mutant proteins conferred intermediate levels of protection. Furthermore, comparatively, the R188A and N191A mutants demonstrated the highest level of protection. This surprising result indicates that a single point mutation in a G protein can result in a polypeptide capable of eliciting a protective immune response concomitantly with a much reduced immunopathological response (e.g., pulmonary eosinophilia).

Example 8

RSV Neutralization Assay

In these experiments, aliquots of pre-titered RSV were mixed with serially diluted samples of individual mouse sera and incubated for 1 hr at room temperature. Serum from individual mice was collected 14 days after the second of two subcutaneous administrations of an immunogen in alum, as described in Example 6. Sera were assayed for RSV neutralizing antibodies by plaque reduction assay. Mixtures were applied in duplicate to 24-well plates containing 60-80% confluent monolayers of HEp-2 cells, adsorbed for 90 minutes at 4° C., followed by washing and incubation of the plates for 40 h at 37° C. in 1 ml of RPMI medium supplemented with 1% fetal calf serum. After incubation, the monolayers were fixed with 15% formaldehyde and stained with 0.01% crystal violet for visualization of viral plaques. Plaque reduction is calculated as the plaque reduction neutralization titerso ($PRNT_{50}$), which is the reciprocal dilution of sera required to neutralize 50% of RSV plaques on a sub-confluent monolayer of HEp-2 cells.

Results of an RSV plaque reduction assay are shown in Table 1. The RSV neutralization titers in sera from immunized mice showed a strong dependence of neutralizing antibody responses upon the amino acid sequence within the 185-193 region of the Trx-G 128-229 protein used for immunization (similar to the immunization results of Example 6).

TABLE 1

Neutralization titers of sera from mice immunized with Trx-G variant proteins

| Immunogen | $PRNT_{50}$* |
|---|---|
| PBS | 7 ± 3 |
| Trx-G128-229 | 144 ± 37 |
| Trx-G128-229 (I185A) | 18 ± 5 |
| Trx-G128-229 (C186A) | 81 ± 12 |
| Trx-G128-229 (K187A) | 34 ± 11 |
| Trx-G128-229 (R188A) | 39 ± 13 |
| Trx-G128-229 (I189A) | 115 ± 38 |
| Trx-G128-229 (P190A) | 98 ± 26 |
| Trx-G128-229 (N191A) | 95 ± 21 |
| Trx-G128-229 (K192A) | 27 ± 7 |
| Trx-G128-229 (K193A) | 31 ± 12 |

*$PRNT_{50}$ (Plaque Reduction Neutralization $Titer_{50}$) is calculated by determining the reciprocal dilution of sera required to neutralize 50% of RSV plaques on HEp-2 cells. The results are expressed as a mean ± SD.

Example 9

Response of Cytokine mRNA to RSV G Protein Variants

Cytokine mRNA levels in lungs of mice immunized with various RSV G protein variants were measured using a ribonuclease protection assay, which can be an indicator of whether a harmful eosinophilic response will result. One lobe from each mouse lung was stored at −20° C. in RNAlater™ solution (Qiagen, Mississauga, ON, Canada) and subsequently processed for RNA extraction using the RNeasy® mini kit (Qiagen, Mississauga, ON, Canada). RNA was quantitated and subjected to ribonuclease protection assay (RPA) using a transcription kit (BD-Pharmingen, Mississauga, ON, Canada) to synthesize probe from a cytokine (MCK-1) template (BD-Pharmingen, Mississauga, ON, Canada), radiolabeled using $\alpha$-$^{32}$P [UTP] and followed by hybridization and RNase digestion using an RPAIII kit (Ambion, Austin, Tex.). Reaction mixtures were resolved on a 5% polyacrylamide 8M urea gel according to the manufacturer's instructions followed by drying and autoradiography at −70° C. using an intensifying screen.

The RPA results illustrated striking differences among the mice immunized with wild-type or mutant Trx-G proteins and subsequently challenged with RSV (FIG. 4). As shown in FIG. 4, the Th2 type cytokines most prone to upregulation were IL-4, IL-10, IL-13 and, to a lesser extent, IL-5. G protein variants K193A, P190A and I189A were found to provoke dramatic IL-4, IL-10 and IL-13 responses. Weak IL-4, IL-10 and IL-13 responses were observed with other G protein variants, such as N192A, N191A, R188A, K187A and C186A. The results of the present study highlight the apparent importance of IL-13, which has been recently implicated in asthma (Grunig et al., *Science* 282: 2261, 1998) as well as in RSV vaccine-induced disease (Johnson and Graham, *J. Virol.* 73:8485, 1999). High levels of IL-13 and IL-10 correlated well with high levels of eosinophilia observed in RSV-challenged mice that had been immunized with wild type or mutants I189A, P190A, K192A and K193A. In contrast, mutants such as N191A, K187A and R188A were poor inducers of IL-13, IL-10 and eosinophilia, despite being decent inducers of IL-4.

In comparison, the prototype Th1 cytokine, IFN-γ, was elevated in all experimental mouse groups. By way of example and not wishing to be bound by theory, this may reflect the expression of IFN-γ from NK cells as well as Th1 cells (Trinchieri, *Adv. Immunol.* 47:187,1989), the rapid induction of IFN-γ upon RSV infection (Hussell and Openshaw, *J. Gen. Virol.* 79: 2593, 1998), and/or the prevalent nature of IFN-γ expression even in immune processes in which a Th2 response appears to predominate (Waris et al., *J. Virol.* 70:2852, 1996; Spender et al., *J. Gen. Virol.* 79: 1751, 1998; Srikiatkhachorn and Braciale, *J. Virol.* 71: 678, 1997).

Example 10

Preparation of Proteosomes Containing RSV G Protein Immunogens

Portions of stock RSV G protein product immunogens (e.g., wild type or mutant peptides) may be formulated with proteosomes using, by way of example, diafiltration/ultrafiltration methods or by using dialysis. For either method, the RSV G protein product is dissolved in, for example, a saline buffered solution containing the desired detergent (e.g., Empigen BB (EBB) at 1% or, at 0.1%-2% of EBB or other suitable detergent depending on the type of detergent used) and is then mixed with proteosomes in saline buffered 1% Empigen solution (or other appropriate detergent at appropriate concentrations) at various proteosome:RSV G (wt/wt) ratios ranging from 1:4 to 8:1, including 1:4, 1:1, 2:1, 4:1 and 8:1. To remove Empigen, the mixture may then be subjected to ultrafiltration/diafilt-ration technology or is exhaustively dialyzed across a dialysis membrane with, for example, a 10,000 molecular weight cut-off (MWCO) or functionally similar membranes with MWCO ranges of 1,000-30,000 against buffered saline for 1-2 weeks at 4° C. exchanging at least 500 parts buffer each day. At various steps, immunological assays such as ELISA and single radial immunodiffusion (SRID) may be used to measure potency. The halo immunodiffusion technique is used to determine the content of formulate RSV G antigen with proteosomes at various ratios (for details on the preparation of proteosomes, see, e.g., U.S. Patent Application Publication No. 2001/0053368).

Multivalent vaccines may also be prepared by making individual monovalent proteosome vaccines and then combining them at the required proportions prior to final formulation and fill. Multivalent preparations may also be formulated by pooling individual RSV G antigens in the desired proportions and formulating the mixture with proteosomes. Multivalent vaccine preparations may contain one or more RSV F protein immunogens and/or one or more M protein immunogens in combination with one or more RSV G protein immunogens. The vaccine composition is then passed through membrane filters of 0.8 µm pore size and stored at 4° C. prior to and during immunizations.

RSV G protein immunogens (e.g., wild type or mutant peptides in any of the previous forms) may also be formulated with various amounts of proteosome-LPS adjuvant as disclosed in, for example, U.S. Pat. No. 6,476,201 B1, and described herein.

Example 11

Immunization with Protollin Formulated RSV G Protein Immunogens

Mice were immunized intranasally with RSV G wild-type (amino acids 128-229) or the mutant (N191A) proteins formulated with Protollin to determine whether RSV-specific systemic and mucosal titers were elicited. BALB/c mice were immunized three times with a dose of 6 µg or 2 µg of either the Trx-(polyHis)-G(128-229) fusion proteins alone, or adjuvanted with protollin or alum. Protollin alone or fusion proteins formulated with protollin were administered intranasally, and alum alone or fusion proteins formulated with alum were administered subcutaneously. Blood was drawn from the saphenous vein after the second dose (day 35) and serum was obtained by exsanguination two weeks after the third dose (day 62). Bronchoalveolar lavage (BAL) samples were also collected on day 62.

Figure 5:
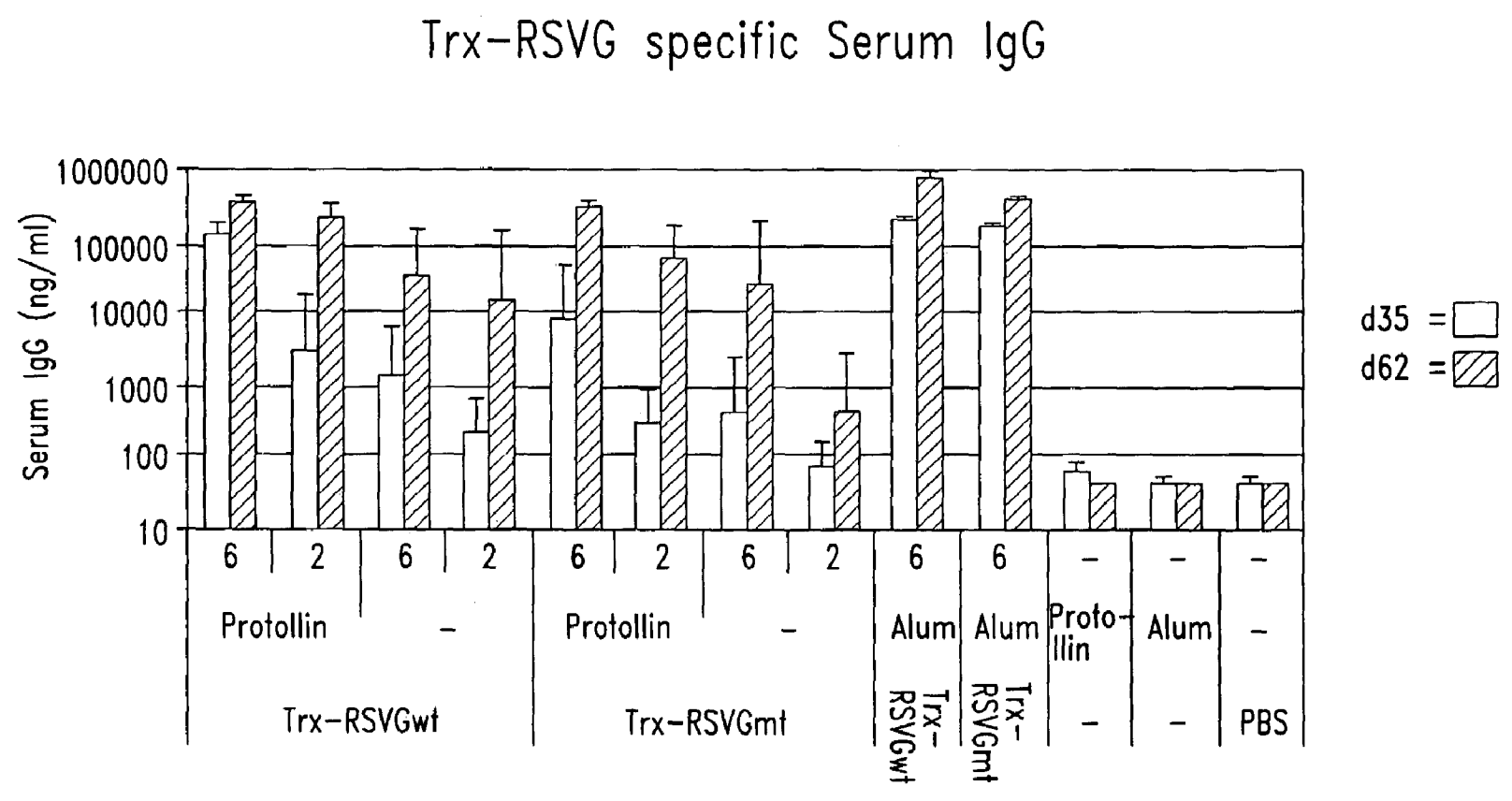
Figure 6:
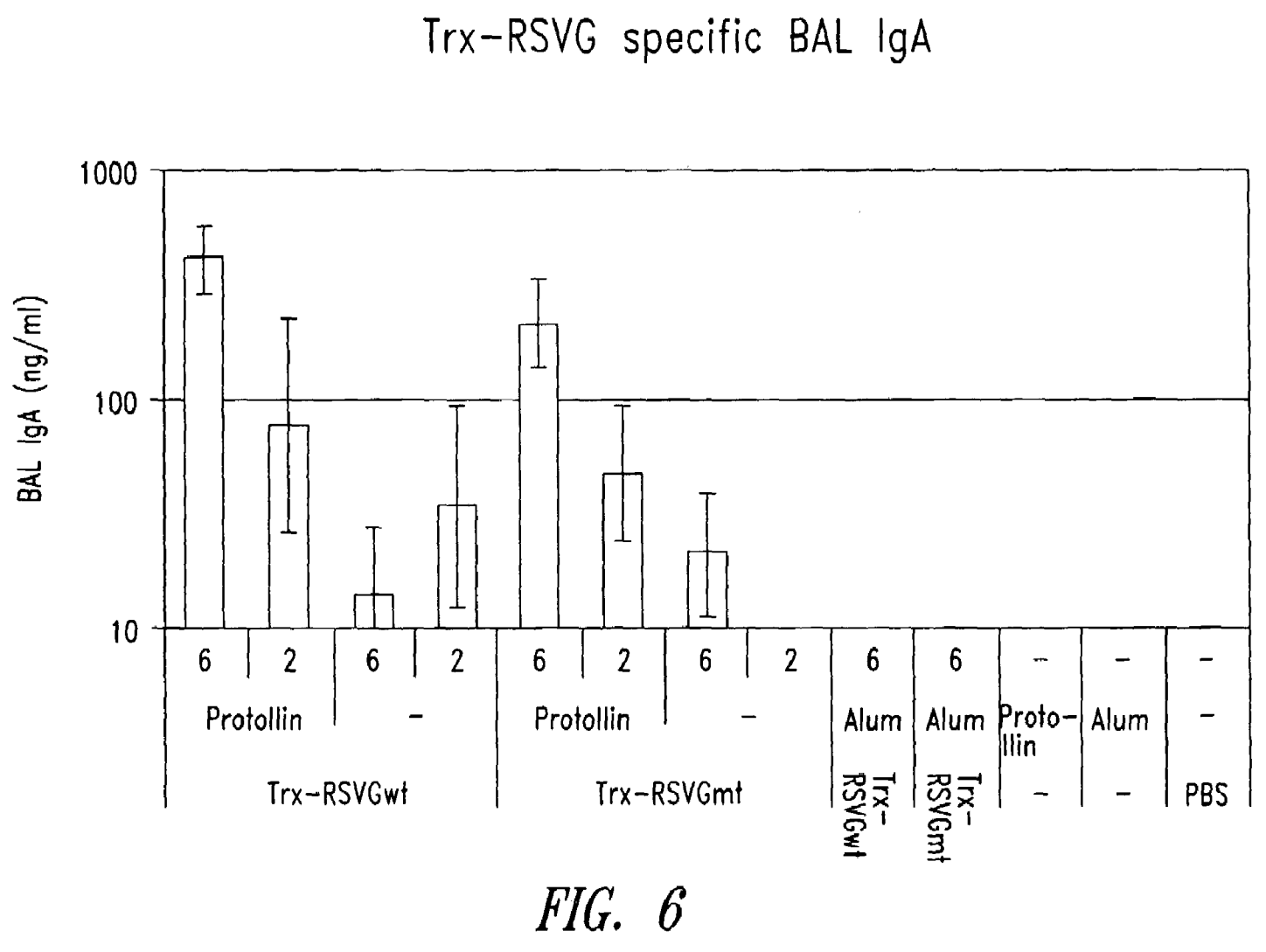

RSV G-specific serum IgG and BAL IgA titers were determined by ELISA. A 10-fold increase in serum IgG titers was observed in mice immunized intranasally with Trx-(polyHis)-G(128-229) formulated with Protollin compared to mice immunized with Trx-(polyHis)-G(128-229) alone, at both the 6 and 2 µg doses (FIG. 5). There was no significant difference in serum IgG titers between the groups immunized intranasally with Protollin formulations or subcutaneously with alum formulations. Comparable titers were obtained for both G(128-229) wild-type and G(128-229) mutant N191A when given with either adjuvant. RSV G(128-229)-specific BAL IgA titers were significantly higher in the groups having received the G(128-229) immunogens (wild-type or mutant) formulated with Protollin compared to the groups immunized with the immunogens alone (FIG. 6). Again, comparable titers were obtained for both wild-type and mutant G(128-229) immunogens. As expected, no IgA was detected in the groups immunized subcutaneously with the G(128-229) immunogens formulated with alum. These results indicate the Protollin formulated G(128-229) immunogens (wild-type or mutant) vaccines are well tolerated and are immunogenic when administered intranasally.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A composition comprising a respiratory syncytial virus G protein inimunogen formulated with an adjuvant comprising proteosome, wherein said G protein immunogen comprises the amino acid sequence set forth in SEQ ID NO:6.

2. The composition according to claim 1 wherein said G protein immunogen comprises the amino acid sequence set forth in SEQ ID NO:2, or a fragment thereof comprising the amino acid sequence of SEQ ID NO:6.

3. The composition according to claim 1 wherein said G protein immunogen further comprises a hydrophobic moiety.

4. The composition according to claim 3 wherein said hydrophobic moiety comprises an amino acid sequence.

5. The composition according to claim 3 wherein said hydrophobic portion is a lipid.

6. The composition according to claim 3 wherein said hydrophobic moiety is at the amino-terminus of the G protein immunogen.

7. The composition according to claim 3 wherein said hydrophobic moiety is at the carboxy-terminus of the G protein immunogen.

8. The composition according to any one of claims 1 to 3 wherein said G protein immunogen or fragment thereof further comprises a second amino acid sequence to form a fusion protein.

9. The composition according to claim 8 wherein said second amino acid sequence is a tag or an enzyme.

10. The composition according to claim 8 wherein said second amino acid sequence is thioredoxin, polyhistidine, or a combination thereof.

11. The composition according to claim 8 wherein said fusion protein further comprises a hydrophobic moiety.

12. The composition according to claim 11 wherein said hydrophobic moiety is at the amino-terminus of the fusion protein.

13. The composition according to claim 11 wherein said hydrophobic moiety is at the carboxy-terminus of the fusion protein.

14. The composition according to claim 1, wherein the adjuvant further comprises a liposaccharide.

* * * * *

SEQUENCE LISTING

<160> NUMBER OF SEQ ID NOS: 72

<210> SEQ ID NO 1
<211> LENGTH: 917
<212> TYPE: DNA
<213> ORGANISM: Artificial Sequence
<220> FEATURE:
<223> OTHER INFORMATION: RSV mutant sequence
<220> FEATURE:
<221> NAME/KEY: misc_feature
<222> LOCATION: 9
<223> OTHER INFORMATION: n = A,T,C or G

<400> SEQUENCE: 1

```
ggggcaaang caaacatgtc caaaaacaag gaccaacgca ccgctaagac actagaaaag      60
acctgggaca ctctcaatca tttattattc atatcatcgg gcttatataa gttaaatctt     120
aaatctatag cacaaatcac attatccatt ctggcaatga taatctcaac ttcacttata     180
attacagcca tcatattcat agcctcggca aaccacaaag tcacactaac aactgcaatc     240
atacaagatg caacaagcca gatcaagaac acaaccccaa catacctcac tcaggatcct     300
cagcttggaa tcagcttctc caatctgtct gaaattacat cacaaaccac caccatacta     360
gcttcaacaa caccaggagt caagtcaaac ctgcaaccca aacagtcaa gactaaaaac      420
acaacaacaa cccaaacaca acccagcaag cccactacaa aacaacgcca aaacaaacca     480
ccaaacaaac caataatga ttttcacttc gaagtgttta actttgtacc ctgcagcata      540
tgcagcaaca atccaacctg ctgggctatc tgcaaaagaa taccagccaa aaaaccagga     600
aagaaaacca ccaccaagcc tacaaaaaaa ccaaccttca agacaaccaa aaagatcac      660
aaacctcaaa ccactaaacc aaaggaagta cccaccacca gcccacaga gagccaacc      720
atcaacacca ccaaaacaaa catcataact acactactca ccaacaacac cacaggaaat     780
ccaaaactca caagtcaaat ggaaaccttc cactcaacct cctccgaagg caatctaagc     840
ccttctcaag tctccacaac atccgagcac ccatcacaac cctcatctcc acccaacaca     900
acacgccagt agttatt                                                    917
```

<210> SEQ ID NO 2
<211> LENGTH: 298
<212> TYPE: PRT
<213> ORGANISM: Artificial Sequence
<220> FEATURE:
<223> OTHER INFORMATION: RSV mutant sequence

<400> SEQUENCE: 2

```
Met Ser Lys Asn Lys Asp Gln Arg Thr Ala Lys Thr Leu Glu Lys Thr
 1               5                  10                  15

Trp Asp Thr Leu Asn His Leu Leu Phe Ile Ser Ser Gly Leu Tyr Lys
            20                  25                  30

Leu Asn Leu Lys Ser Ile Ala Gln Ile Thr Leu Ser Ile Leu Ala Met
        35                  40                  45

Ile Ile Ser Thr Ser Leu Ile Ile Thr Ala Ile Ile Phe Ile Ala Ser
    50                  55                  60

Ala Asn His Lys Val Thr Leu Thr Thr Ala Ile Ile Gln Asp Ala Thr
65                  70                  75                  80

Ser Gln Ile Lys Asn Thr Thr Pro Thr Tyr Leu Thr Gln Asp Pro Gln
                85                  90                  95

Leu Gly Ile Ser Phe Ser Asn Leu Ser Glu Ile Thr Ser Gln Thr Thr
```

-continued

```
            100                 105                 110

Thr Ile Leu Ala Ser Thr Thr Pro Gly Val Lys Ser Asn Leu Gln Pro
        115                 120                 125

Thr Thr Val Lys Thr Lys Asn Thr Thr Thr Thr Gln Thr Gln Pro Ser
    130                 135                 140

Lys Pro Thr Thr Lys Gln Arg Gln Asn Lys Pro Pro Asn Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Ala Lys
            180                 185                 190

Lys Pro Gly Lys Lys Thr Thr Thr Lys Pro Thr Lys Lys Pro Thr Phe
        195                 200                 205

Lys Thr Thr Lys Lys Asp His Lys Pro Gln Thr Thr Lys Pro Lys Glu
    210                 215                 220

Val Pro Thr Thr Lys Pro Thr Glu Glu Pro Thr Ile Asn Thr Thr Lys
225                 230                 235                 240

Thr Asn Ile Ile Thr Thr Leu Leu Thr Asn Asn Thr Thr Gly Asn Pro
                245                 250                 255

Lys Leu Thr Ser Gln Met Glu Thr Phe His Ser Thr Ser Ser Glu Gly
            260                 265                 270

Asn Leu Ser Pro Ser Gln Val Ser Thr Thr Ser Glu His Pro Ser Gln
        275                 280                 285

Pro Ser Ser Pro Pro Asn Thr Thr Arg Gln
    290                 295
```

<210> SEQ ID NO 3
<211> LENGTH: 917
<212> TYPE: DNA
<213> ORGANISM: Respiratory syncytial virus
<220> FEATURE:
<221> NAME/KEY: misc_feature
<222> LOCATION: 9
<223> OTHER INFORMATION: n = A,T,C or G

<400> SEQUENCE: 3

```
ggggcaaang caaacatgtc caaaaacaag gaccaacgca ccgctaagac actagaaaag     60
acctgggaca ctctcaatca tttattattc atatcatcgg gcttatataa gttaaatctt    120
aaatctatag cacaaatcac attatccatt ctggcaatga taatctcaac ttcacttata    180
attacagcca tcatattcat agcctcggca aaccacaaag tcacactaac aactgcaatc    240
atacaagatg caacaagcca gatcaagaac acaaccccaa catacctcac tcaggatcct    300
cagcttggaa tcagcttctc caatctgtct gaaattacat cacaaaccac caccatacta    360
gcttcaacaa caccaggagt caagtcaaac ctgcaaccca caacagtcaa gactaaaaac    420
acaacaacaa cccaaacaca acccagcaag cccactacaa aacaacgcca aaacaaacca    480
ccaaacaaac ccaataatga ttttcacttc gaagtgttta actttgtacc ctgcagcata    540
tgcagcaaca atccaacctg ctgggctatc tgcaaaagaa taccaaacaa aaaaccagga    600
aagaaaacca ccaccaagcc tacaaaaaaa ccaaccttca agacaaccaa aaaagatcac    660
aaacctcaaa ccactaaacc aaaggaagta cccaccacca agcccacaga agagccaacc    720
atcaacacca ccaaaacaaa catcataact acactactca ccaacaacac cacaggaaat    780
ccaaaactca caagtcaaat ggaaaccttc cactcaacct cctccgaagg caatctaagc    840
ccttctcaag tctccacaac atccgagcac ccatcacaac cctcatctcc acccaacaca    900
```
acacgccagt agttatt                                                  917

<210> SEQ ID NO 4
<211> LENGTH: 298
<212> TYPE: PRT
<213> ORGANISM: Respiratory sy

<400> SEQUENCE: 4

Met Ser Lys Asn Lys Asp Gln Arg Thr Ala Lys Thr Leu Glu Lys Thr
 1               5                  10                  15

Trp Asp Thr Leu Asn His Leu Leu Phe Ile Ser Ser Gly Leu Tyr Lys
             20                  25                  30

Leu Asn Leu Lys Ser Ile Ala Gln Ile Thr Leu Ser Ile Leu Ala Met
         35                  40                  45

Ile Ile Ser Thr Ser Leu Ile Ile Thr Ala Ile Ile Phe Ile Ala Ser
     50                  55                  60

Ala Asn His Lys Val Thr Leu Thr Thr Ala Ile Ile Gln Asp Ala Thr
65                  70                  75                  80

Ser Gln Ile Lys Asn Thr Thr Pro Thr Tyr Leu Thr Gln Asp Pro Gln
                 85                  90                  95

Leu Gly Ile Ser Phe Ser Asn Leu Ser Glu Ile Thr Ser Gln Thr Thr
            100                 105                 110

Thr Ile Leu Ala Ser Thr Thr Pro Gly Val Lys Ser Asn Leu Gln Pro
        115                 120                 125

Thr Thr Val Lys Thr Lys Asn Thr Thr Thr Thr Gln Thr Gln Pro Ser
    130                 135                 140

Lys Pro Thr Thr Lys Gln Arg Gln Asn Lys Pro Pro Asn Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro Thr Phe
        195                 200                 205

Lys Thr Thr Lys Lys Asp His Lys Pro Gln Thr Thr Lys Pro Lys Glu
    210                 215                 220

Val Pro Thr Thr Lys Pro Thr Glu Glu Pro Thr Ile Asn Thr Thr Lys
225                 230                 235                 240

Thr Asn Ile Ile Thr Thr Leu Leu Thr Asn Asn Thr Thr Gly Asn Pro
                245                 250                 255

Lys Leu Thr Ser Gln Met Glu Thr Phe His Ser Thr Ser Ser Glu Gly
            260                 265                 270

Asn Leu Ser Pro Ser Gln Val Ser Thr Thr Ser Glu His Pro Ser Gln
        275                 280                 285

Pro Ser Ser Pro Pro Asn Thr Thr Arg Gln
    290                 295

<210> SEQ ID NO 5
<211> LENGTH: 306
<212> TYPE: DNA
<213> ORGANISM: Artificial Sequence
<220> FEATURE:
<223> OTHER INFORMATION: RSV mutant fragment

<400> SEQUENCE: 5
cccacaacag tcaagactaa aaacacaaca acaacccaaa cacaacccag caagcccact    60

```
acaaaacaac gccaaaacaa accaccaaac aaacccaata atgattttca cttcgaagtg    120
tttaactttg taccctgcag catatgcagc aacaatccaa cctgctgggc tatctgcaaa    180
agaataccag ccaaaaaacc aggaaagaaa accaccacca agcctacaaa aaaaccaacc    240
ttcaagacaa ccaaaaaaga tcacaaacct caaaccacta aaccaaagga agtacccacc    300
accaag                                                               306
```

```
<210> SEQ ID NO 6
<211> LENGTH: 102
<212> TYPE: PRT
<213> ORGANISM: Artificial Sequence
<220> FEATURE:
<223> OTHER INFORMATION: RSV mutant fragment

<400> SEQUENCE: 6

Pro Thr Thr Val Lys Thr Lys Asn Thr Thr Thr Gln Thr Gln Pro
 1               5                  10                  15

Ser Lys Pro Thr Thr Lys Gln Arg Gln Asn Lys Pro Pro Asn Lys Pro
            20                  25                  30

Asn Asn Asp Phe His Phe Glu Val Phe Asn Phe Val Pro Cys Ser Ile
        35                  40                  45

Cys Ser Asn Asn Pro Thr Cys Trp Ala Ile Cys Lys Arg Ile Pro Ala
    50                  55                  60

Lys Lys Pro Gly Lys Lys Thr Thr Thr Lys Pro Thr Lys Lys Pro Thr
65                  70                  75                  80

Phe Lys Thr Thr Lys Lys Asp His Lys Pro Gln Thr Thr Lys Pro Lys
                85                  90                  95

Glu Val Pro Thr Thr Lys
            100
```

```
<210> SEQ ID NO 7
<211> LENGTH: 306
<212> TYPE: DNA
<213> ORGANISM: Artificial Sequence
<220> FEATURE:
<223> OTHER INFORMATION: RSV mutant sequence

<400> SEQUENCE: 7
cccacaacag tcaagactaa aaacacaaca acaacccaaa cacaacccag caagcccact     60
acaaaacaac gccaaaacaa accaccaaac aaacccaata atgattttca cttcgaagtg    120
tttaactttg taccctgcag catatgcagc aacaatccaa cctgctgggc tatctgcaaa    180
gcaataccaa acaaaaaacc aggaaagaaa accaccacca agcctacaaa aaaaccaacc    240
ttcaagacaa ccaaaaaaga tcacaaacct caaaccacta aaccaaagga agtacccacc    300
accaag                                                               306
```

```
<210> SEQ ID NO 8
<211> LENGTH: 102
<212> TYPE: PRT
<213> ORGANISM: Artificial Sequence
<220> FEATURE:
<223> OTHER INFORMATION: RSV mutant fragment

<400> SEQUENCE: 8

Pro Thr Thr Val Lys Thr Lys Asn Thr Thr Thr Gln Thr Gln Pro
 1               5                  10                  15

Ser Lys Pro Thr Thr Lys Gln Arg Gln Asn Lys Pro Pro Asn Lys Pro
            20                  25                  30
```

```
Asn Asn Asp Phe His Phe Glu Val Phe Asn Phe Val Pro Cys Ser Ile
            35                  40                  45

Cys Ser Asn Asn Pro Thr Cys Trp Ala Ile Cys Lys Ala Ile Pro Asn
    50                  55                  60

Lys Lys Pro Gly Lys Lys Thr Thr Thr Lys Pro Thr Lys Lys Pro Thr
65                  70                  75                  80

Phe Lys Thr Thr Lys Lys Asp His Lys Pro Gln Thr Thr Lys Pro Lys
                85                  90                  95

Glu Val Pro Thr Thr Lys
            100

<210> SEQ ID NO 9
<211> LENGTH: 306
<212> TYPE: DNA
<213> ORGANISM: Artificial Sequence
<220> FEATURE:
<223> OTHER INFORMATION: RSV mutant fragment

<400> SEQUENCE: 9
cccacaacag tcaagactaa aaacacaaca acaacccaaa cacaacccag caagcccact      60
acaaaacaac gccaaaacaa accaccaaac aaacccaata atgattttca cttcgaagtg     120
tttaactttg taccctgcag catatgcagc aacaatccaa cctgctgggc tatctgcaaa     180
agaatagcaa acaaaaaacc aggaaagaaa accaccacca agcctacaaa aaaaccaacc     240
ttcaagacaa ccaaaaaaga tcacaaacct caaaccacta aaccaaagga agtacccacc     300
accaag                                                                306

<210> SEQ ID NO 10
<211> LENGTH: 102
<212> TYPE: PRT
<213> ORGANISM: Artificial Sequence
<220> FEATURE:
<223> OTHER INFORMATION: RSV mutant fragment

<400> SEQUENCE: 10

Pro Thr Thr Val Lys Thr Lys Asn Thr Thr Thr Thr Gln Thr Gln Pro
 1               5                  10                  15

Ser Lys Pro Thr Thr Lys Gln Arg Gln Asn Lys Pro Pro Asn Lys Pro
            20                  25                  30

Asn Asn Asp Phe His Phe Glu Val Phe Asn Phe Val Pro Cys Ser Ile
            35                  40                  45

Cys Ser Asn Asn Pro Thr Cys Trp Ala Ile Cys Lys Arg Ile Ala Asn
    50                  55                  60

Lys Lys Pro Gly Lys Lys Thr Thr Thr Lys Pro Thr Lys Lys Pro Thr
65                  70                  75                  80

Phe Lys Thr Thr Lys Lys Asp His Lys Pro Gln Thr Thr Lys Pro Lys
                85                  90                  95

Glu Val Pro Thr Thr Lys
            100

<210> SEQ ID NO 11
<211> LENGTH: 306
<212> TYPE: DNA
<213> ORGANISM: Artificial Sequence
<220> FEATURE:
<223> OTHER INFORMATION: RSV mutant fragment

<400> SEQUENCE: 11
```

-continued

```
cccacaacag tcaagactaa aaacacaaca acaacccaaa cacaacccag caagcccact     60
acaaaacaac gccaaaacaa accaccaaac aaacccaata atgattttca cttcgaagtg    120
tttaactttg taccctgcag catatgcagc aacaatccaa cctgctgggc tgcctgcaaa    180
agaataccaa acaaaaaacc aggaaagaaa accaccacca agcctacaaa aaaaccaacc    240
ttcaagacaa ccaaaaaaga tcacaaacct caaaccacta aaccaaagga agtacccacc    300
accaag                                                               306
```

<210> SEQ ID NO 12
<211> LENGTH: 102
<212> TYPE: PRT
<213> ORGANISM: Artificial Sequence
<220> FEATURE:
<223> OTHER INFORMATION: RSV mutant fragment

<400> SEQUENCE: 12

Pro Thr Thr Val Lys Thr Lys Asn Thr Thr Thr Gln Thr Gln Pro
 1               5                  10                  15

Ser Lys Pro Thr Thr Lys Gln Arg Gln Asn Lys Pro Pro Asn Lys Pro
                20                  25                  30

Asn Asn Asp Phe His Phe Glu Val Phe Asn Phe Val Pro Cys Ser Ile
                35                  40                  45

Cys Ser Asn Asn Pro Thr Cys Trp Ala Ala Cys Lys Arg Ile Pro Asn
    50                  55                  60

Lys Lys Pro Gly Lys Lys Thr Thr Thr Lys Pro Thr Lys Lys Pro Thr
65                  70                  75                  80

Phe Lys Thr Thr Lys Lys Asp His Lys Pro Gln Thr Lys Pro Lys
                85                  90                  95

Glu Val Pro Thr Thr Lys
            100

<210> SEQ ID NO 13
<211> LENGTH: 306
<212> TYPE: DNA
<213> ORGANISM: Artificial Sequence
<220> FEATURE:
<223> OTHER INFORMATION: RSV mutant fragment

<400> SEQUENCE: 13

```
cccacaacag tcaagactaa aaacacaaca acaacccaaa cacaacccag caagcccact     60
acaaaacaac gccaaaacaa accaccaaac aaacccaata atgattttca cttcgaagtg    120
tttaactttg taccctgcag catatgcagc aacaatccaa cctgctgggc tatcgccaaa    180
agaataccaa acaaaaaacc aggaaagaaa accaccacca agcctacaaa aaaaccaacc    240
ttcaagacaa ccaaaaaaga tcacaaacct caaaccacta aaccaaagga agtacccacc    300
accaag                                                               306
```

<210> SEQ ID NO 14
<211> LENGTH: 102
<212> TYPE: PRT
<213> ORGANISM: Artificial Sequence
<220> FEATURE:
<223> OTHER INFORMATION: RSV mutant fragment

<400> SEQUENCE: 14

Pro Thr Thr Val Lys Thr Lys Asn Thr Thr Thr Gln Thr Gln Pro
 1               5                  10                  15

Ser Lys Pro Thr Thr Lys Gln Arg Gln Asn Lys Pro Pro Asn Lys Pro

```
                     20                  25                  30
Asn Asn Asp Phe His Phe Glu Val Phe Asn Phe Val Pro Cys Ser Ile
            35                  40                  45

Cys Ser Asn Asn Pro Thr Cys Trp Ala Ile Ala Lys Arg Ile Pro Asn
         50                  55                  60

Lys Lys Pro Gly Lys Lys Thr Thr Thr Lys Pro Thr Lys Lys Pro Thr
 65                  70                  75                  80

Phe Lys Thr Thr Lys Lys Asp His Lys Pro Gln Thr Thr Lys Pro Lys
                 85                  90                  95

Glu Val Pro Thr Thr Lys
            100

<210> SEQ ID NO 15
<211> LENGTH: 306
<212> TYPE: DNA
<213> ORGANISM: Artificial Sequence
<220> FEATURE:
<223> OTHER INFORMATION: RSV mutant fragment

<400> SEQUENCE: 15
cccacaacag tcaagactaa aaacacaaca acaacccaaa cacaacccag caagcccact    60
acaaaacaac gccaaaacaa accaccaaac aaacccaata atgattttca cttcgaagtg   120
tttaactttg taccctgcag catatgcagc aacaatccaa cctgctgggc tatctgcgca   180
agaataccaa acaaaaaacc aggaaagaaa accaccacca agcctacaaa aaaaccaacc   240
ttcaagacaa ccaaaaaaga tcacaaacct caaaccacta accaaggaa agtacccacc   300 accaag                                                             306

<210> SEQ ID NO 16
<211> LENGTH: 102
<212> TYPE: PRT
<213> ORGANISM: Artificial Sequence
<220> FEATURE:
<223> OTHER INFORMATION: RSV mutant fragment

<400> SEQUENCE: 16

Pro Thr Thr Val Lys Thr Lys Asn Thr Thr Thr Thr Gln Thr Gln Pro
 1               5                  10                  15

Ser Lys Pro Thr Thr Lys Gln Arg Gln Asn Lys Pro Pro Asn Lys Pro
             20                  25                  30

Asn Asn Asp Phe His Phe Glu Val Phe Asn Phe Val Pro Cys Ser Ile
            35                  40                  45

Cys Ser Asn Asn Pro Thr Cys Trp Ala Ile Cys Ala Arg Ile Pro Asn
         50                  55                  60

Lys Lys Pro Gly Lys Lys Thr Thr Thr Lys Pro Thr Lys Lys Pro Thr
 65                  70                  75                  80

Phe Lys Thr Thr Lys Lys Asp His Lys Pro Gln Thr Thr Lys Pro Lys
                 85                  90                  95

Glu Val Pro Thr Thr Lys
            100

<210> SEQ ID NO 17
<211> LENGTH: 306
<212> TYPE: DNA
<213> ORGANISM: Artificial Sequence
<220> FEATURE:
<223> OTHER INFORMATION: RSV mutant fragment

<400> SEQUENCE: 17
```

```
cccacaacag tcaagactaa aaacacaaca acaacccaaa cacaacccag caagcccact      60
acaaaacaac gccaaaacaa accaccaaac aaacccaata atgattttca cttcgaagtg     120
tttaactttg taccctgcag catatgcagc aacaatccaa cctgctgggc tatctgcaaa    180
agagcaccaa acaaaaaacc aggaaagaaa accaccacca agcctacaaa aaaaccaacc    240
ttcaagacaa ccaaaaaaga tcacaaacct caaaccacta aaccaaagga agtacccacc    300
accaag                                                               306
```

<210> SEQ ID NO 18
<211> LENGTH: 102
<212> TYPE: PRT
<213> ORGANISM: Artificial Sequence
<220> FEATURE:
<223> OTHER INFORMATION: RSV mutant fragment

<400> SEQUENCE: 18

```
Pro Thr Thr Val Lys Thr Lys Asn Thr Thr Thr Thr Gln Thr Gln Pro
 1               5                  10                  15

Ser Lys Pro Thr Thr Lys Gln Arg Gln Asn Lys Pro Pro Asn Lys Pro
            20                  25                  30

Asn Asn Asp Phe His Phe Glu Val Phe Asn Phe Val Pro Cys Ser Ile
        35                  40                  45

Cys Ser Asn Asn Pro Thr Cys Trp Ala Ile Cys Lys Arg Ala Pro Asn
    50                  55                  60

Lys Lys Pro Gly Lys Lys Thr Thr Thr Lys Pro Thr Lys Lys Pro Thr
65                  70                  75                  80

Phe Lys Thr Thr Lys Lys Asp His Lys Pro Gln Thr Thr Lys Pro Lys
                85                  90                  95

Glu Val Pro Thr Thr Lys
            100
```

<210> SEQ ID NO 19
<211> LENGTH: 306
<212> TYPE: DNA
<213> ORGANISM: Artificial Sequence
<220> FEATURE:
<223> OTHER INFORMATION: RSV mutant fragment

<400> SEQUENCE: 19

```
cccacaacag tcaagactaa aaacacaaca acaacccaaa cacaacccag caagcccact      60
acaaaacaac gccaaaacaa accaccaaac aaacccaata atgattttca cttcgaagtg     120
tttaactttg taccctgcag catatgcagc aacaatccaa cctgctgggc tatctgcaaa    180
agaataccaa acgcaaaaacc aggaaagaaa accaccacca agcctacaaa aaaaccaacc    240
ttcaagacaa ccaaaaaaga tcacaaacct caaaccacta aaccaaagga agtacccacc    300
accaag                                                               306
```

<210> SEQ ID NO 20
<211> LENGTH: 102
<212> TYPE: PRT
<213> ORGANISM: Artificial Sequence
<220> FEATURE:
<223> OTHER INFORMATION: RSV mutant fragment

<400> SEQUENCE: 20

```
Pro Thr Thr Val Lys Thr Lys Asn Thr Thr Thr Thr Gln Thr Gln Pro
 1               5                  10                  15
```

```
Ser Lys Pro Thr Thr Lys Gln Arg Gln Asn Lys Pro Asn Lys Pro
         20                  25                  30

Asn Asn Asp Phe His Phe Glu Val Phe Asn Phe Val Pro Cys Ser Ile
             35                  40                  45

Cys Ser Asn Asn Pro Thr Cys Trp Ala Ile Cys Lys Arg Ile Pro Asn
 50                  55                  60

Ala Lys Pro Gly Lys Lys Thr Thr Thr Lys Pro Thr Lys Lys Pro Thr
 65                  70                  75                  80

Phe Lys Thr Thr Lys Lys Asp His Lys Pro Gln Thr Thr Lys Pro Lys
                 85                  90                  95

Glu Val Pro Thr Thr Lys
            100
```

```
<210> SEQ ID NO 21
<211> LENGTH: 306
<212> TYPE: DNA
<213> ORGANISM: Artificial Sequence
<220> FEATURE:
<223> OTHER INFORMATION: RSV mutant fragment

<400> SEQUENCE: 21
cccacaacag tcaagactaa aaacacaaca caacccaaa cacaacccag caagcccact      60
acaaaacaac gccaaaacaa accaccaaac aaacccaata atgattttca cttcgaagtg    120
tttaactttg taccctgcag catatgcagc aacaatccaa cctgctgggc tatctgcaaa    180
agaataccaa acaaagcacc aggaaagaaa accaccacca agcctacaaa aaaaccaacc    240
ttcaagacaa ccaaaaaaga tcacaaacct caaaccacta accaaagga agtacccacc    300 accaag                                                               306
```

```
<210> SEQ ID NO 22
<211> LENGTH: 102
<212> TYPE: PRT
<213> ORGANISM: Artificial Sequence
<220> FEATURE:
<223> OTHER INFORMATION: RSV mutant fragment

<400> SEQUENCE: 22

Pro Thr Thr Val Lys Thr Lys Asn Thr Thr Thr Gln Thr Gln Pro
 1               5                  10                  15

Ser Lys Pro Thr Thr Lys Gln Arg Gln Asn Lys Pro Asn Lys Pro
         20                  25                  30

Asn Asn Asp Phe His Phe Glu Val Phe Asn Phe Val Pro Cys Ser Ile
             35                  40                  45

Cys Ser Asn Asn Pro Thr Cys Trp Ala Ile Cys Lys Arg Ile Pro Asn
 50                  55                  60

Lys Ala Pro Gly Lys Lys Thr Thr Thr Lys Pro Thr Lys Lys Pro Thr
 65                  70                  75                  80

Phe Lys Thr Thr Lys Lys Asp His Lys Pro Gln Thr Thr Lys Pro Lys
                 85                  90                  95

Glu Val Pro Thr Thr Lys
            100
```

```
<210> SEQ ID NO 23
<211> LENGTH: 825
<212> TYPE: DNA
<213> ORGANISM: Artificial Sequence
<220> FEATURE:
<223> OTHER INFORMATION: RSV mutant fragment
<220> FEATURE:
```

<221> NAME/KEY: CDS
<222> LOCATION: (1)...(825)

<400> SEQUENCE: 23

```
atg tcc gac aaa atc atc cac ctg act gac gac agt ttt gac acg gat      48
Met Ser Asp Lys Ile Ile His Leu Thr Asp Asp Ser Phe Asp Thr Asp
 1               5                  10                  15 gta ctc aaa gcg gac ggg gcg atc ctc gtc gat ttc tgg gca gag tgg      96
Val Leu Lys Ala Asp Gly Ala Ile Leu Val Asp Phe Trp Ala Glu Trp
             20                  25                  30 tgc ggt ccg tgc aaa atg atc gcc ccg att ctg gat gaa atc gct gac     144
Cys Gly Pro Cys Lys Met Ile Ala Pro Ile Leu Asp Glu Ile Ala Asp
         35                  40                  45 gaa tat cag ggc aaa ctg acc gtt gca aaa ctg aac atc gat caa aac     192
Glu Tyr Gln Gly Lys Leu Thr Val Ala Lys Leu Asn Ile Asp Gln Asn
     50                  55                  60 cct ggc act gcg ccg aaa tat ggc atc cgt ggt atc ccg act ctg ctg     240
Pro Gly Thr Ala Pro Lys Tyr Gly Ile Arg Gly Ile Pro Thr Leu Leu
 65                  70                  75                  80 ctg ttc aaa aac ggt gaa gtg gcg gca acc aaa gtg ggt gca ctg tct     288
Leu Phe Lys Asn Gly Glu Val Ala Ala Thr Lys Val Gly Ala Leu Ser
                 85                  90                  95 aaa ggt cag ttg aaa gag ttc ctc gac gct aac ctg gcc ggt tct ggt     336
Lys Gly Gln Leu Lys Glu Phe Leu Asp Ala Asn Leu Ala Gly Ser Gly
            100                 105                 110 tct ggc cac atg cac cat cat cat cat cat tct tct ggt ctg gtg cca     384
Ser Gly His Met His His His His His His Ser Ser Gly Leu Val Pro
        115                 120                 125 cgc ggt tct ggt atg aaa gaa acc gct gct gct aaa ttc gaa cgc cag     432
Arg Gly Ser Gly Met Lys Glu Thr Ala Ala Ala Lys Phe Glu Arg Gln
    130                 135                 140 cac atg gac agc cca gat ctg ggt acc gat gac gac gac aag acc ggg     480
His Met Asp Ser Pro Asp Leu Gly Thr Asp Asp Asp Asp Lys Thr Gly
145                 150                 155                 160 ctt ctc ctc aac cat ggc gat atc gga tcc gaa ttc ccc aca aca gtc     528
Leu Leu Leu Asn His Gly Asp Ile Gly Ser Glu Phe Pro Thr Thr Val
                165                 170                 175 aag act aaa aac aca aca aca acc caa aca caa ccc agc aag ccc act     576
Lys Thr Lys Asn Thr Thr Thr Thr Gln Thr Gln Pro Ser Lys Pro Thr
            180                 185                 190 aca aaa caa cgc caa aac aaa cca cca aac aaa ccc aat aat gat ttt     624
Thr Lys Gln Arg Gln Asn Lys Pro Pro Asn Lys Pro Asn Asn Asp Phe
        195                 200                 205 cac ttc gaa gtg ttt aac ttt gta ccc tgc agc atc tgc agc aac aat     672
His Phe Glu Val Phe Asn Phe Val Pro Cys Ser Ile Cys Ser Asn Asn
    210                 215                 220 cca acc tgc tgg gct atc tgc aaa aga ata cca aac aaa aaa cca gga     720
Pro Thr Cys Trp Ala Ile Cys Lys Arg Ile Pro Asn Lys Lys Pro Gly
225                 230                 235                 240 aag aaa acc acc acc aag cct aca aaa aaa cca acc ttc aag aca acc     768
Lys Lys Thr Thr Thr Lys Pro Thr Lys Lys Pro Thr Phe Lys Thr Thr
                245                 250                 255 aaa aaa gat ctc aaa cct caa acc act aaa cca aag gaa gta ccc acc     816
Lys Lys Asp Leu Lys Pro Gln Thr Thr Lys Pro Lys Glu Val Pro Thr
            260                 265                 270 acc aag tga                                                         825
Thr Lys *
```

<210> SEQ ID NO 24
<211> LENGTH: 274

```
<212> TYPE: PRT
<213> ORGANISM: Artificial Sequence
<220> FEATURE:
<223> OTHER INFORMATION: :

<400> SEQUENCE: 24

Met Ser Asp Lys Ile Ile His Leu Thr Asp Asp Ser Phe Asp Thr Asp
 1               5                  10                  15

Val Leu Lys Ala Asp Gly Ala Ile Leu Val Asp Phe Trp Ala Glu Trp
             20                  25                  30

Cys Gly Pro Cys Lys Met Ile Ala Pro Ile Leu Asp Glu Ile Ala Asp
         35                  40                  45

Glu Tyr Gln Gly Lys Leu Thr Val Ala Lys Leu Asn Ile Asp Gln Asn
     50                  55                  60

Pro Gly Thr Ala Pro Lys Tyr Gly Ile Arg Gly Ile Pro Thr Leu Leu
 65                  70                  75                  80

Leu Phe Lys Asn Gly Glu Val Ala Ala Thr Lys Val Gly Ala Leu Ser
                 85                  90                  95

Lys Gly Gln Leu Lys Glu Phe Leu Asp Ala Asn Leu Ala Gly Ser Gly
            100                 105                 110

Ser Gly His Met His His His His His His Ser Ser Gly Leu Val Pro
        115                 120                 125

Arg Gly Ser Gly Met Lys Glu Thr Ala Ala Ala Lys Phe Glu Arg Gln
    130                 135                 140

His Met Asp Ser Pro Asp Leu Gly Thr Asp Asp Asp Lys Thr Gly
145                 150                 155                 160

Leu Leu Leu Asn His Gly Asp Ile Gly Ser Glu Phe Pro Thr Thr Val
                165                 170                 175

Lys Thr Lys Asn Thr Thr Thr Thr Gln Thr Gln Pro Ser Lys Pro Thr
            180                 185                 190

Thr Lys Gln Arg Gln Asn Lys Pro Pro Asn Lys Pro Asn Asn Asp Phe
        195                 200                 205

His Phe Glu Val Phe Asn Phe Val Pro Cys Ser Ile Cys Ser Asn Asn
    210                 215                 220

Pro Thr Cys Trp Ala Ile Cys Lys Arg Ile Pro Asn Lys Lys Pro Gly
225                 230                 235                 240

Lys Lys Thr Thr Thr Lys Pro Thr Lys Lys Pro Thr Phe Lys Thr Thr
                245                 250                 255

Lys Lys Asp Leu Lys Pro Gln Thr Thr Lys Pro Lys Glu Val Pro Thr
            260                 265                 270

Thr Lys

<210> SEQ ID NO 25
<211> LENGTH: 825
<212> TYPE: DNA
<213> ORGANISM: Artificial Sequence
<220> FEATURE:
<223> OTHER INFORMATION: RSV mutant fragment
<220> FEATURE:
<221> NAME/KEY: CDS
<222> L

```
                     20                  25                  30
tgc ggt ccg tgc aaa atg atc gcc ccg att ctg gat gaa atc gct gac      144
Cys Gly Pro Cys Lys Met Ile Ala Pro Ile Leu Asp Glu Ile Ala Asp
             35                  40                  45 gaa tat cag ggc aaa ctg acc gtt gca aaa ctg aac atc gat caa aac      192
Glu Tyr Gln Gly Lys Leu Thr Val Ala Lys Leu Asn Ile Asp Gln Asn
 50                  55                  60 cct ggc act gcg ccg aaa tat ggc atc cgt ggt atc ccg act ctg ctg      240
Pro Gly Thr Ala Pro Lys Tyr Gly Ile Arg Gly Ile Pro Thr Leu Leu
 65                  70                  75                  80 ctg ttc aaa aac ggt gaa gtg gcg gca acc aaa gtg ggt gca ctg tct      288
Leu Phe Lys Asn Gly Glu Val Ala Ala Thr Lys Val Gly Ala Leu Ser
                 85                  90                  95 aaa ggt cag ttg aaa gag ttc ctc gac gct aac ctg gcc ggt tct ggt      336
Lys Gly Gln Leu Lys Glu Phe Leu Asp Ala Asn Leu Ala Gly Ser Gly
            100                 105                 110 tct ggc cac atg cac cat cat cat cat cat tct tct ggt ctg gtg cca      384
Ser Gly His Met His His His His His His Ser Ser Gly Leu Val Pro
            115                 120                 125 cgc ggt tct ggt atg aaa gaa acc gct gct gct aaa ttc gaa cgc cag      432
Arg Gly Ser Gly Met Lys Glu Thr Ala Ala Ala Lys Phe Glu Arg Gln
130                 135                 140 cac atg gac agc cca gat ctg ggt acc gat gac gac gac aag acc ggg      480
His Met Asp Ser Pro Asp Leu Gly Thr Asp Asp Asp Asp Lys Thr Gly
145                 150                 155                 160 ctt ctc ctc aac cat ggc gat atc gga tcc gaa ttc ccc aca aca gtc      528
Leu Leu Leu Asn His Gly Asp Ile Gly Ser Glu Phe Pro Thr Thr Val
                165                 170                 175 aag act aaa aac aca aca aca acc caa aca caa ccc agc aag ccc act      576
Lys Thr Lys Asn Thr Thr Thr Thr Gln Thr Gln Pro Ser Lys Pro Thr
            180                 185                 190 aca aaa caa cgc caa aac aaa cca cca aac aaa ccc aat aat gat ttt      624
Thr Lys Gln Arg Gln Asn Lys Pro Pro Asn Lys Pro Asn Asn Asp Phe
        195                 200                 205 cac ttc gaa gtg ttt aac ttt gta ccc tgc agc atc tgc agc aac aat      672
His Phe Glu Val Phe Asn Phe Val Pro Cys Ser Ile Cys Ser Asn Asn
210                 215                 220 cca acc tgc tgg gct atc tgc aaa aga ata cca gct aaa aaa cca gga      720
Pro Thr Cys Trp Ala Ile Cys Lys Arg Ile Pro Ala Lys Lys Pro Gly
225                 230                 235                 240 aag aaa acc acc acc aag cct aca aaa aaa cca acc ttc aag aca acc      768
Lys Lys Thr Thr Thr Lys Pro Thr Lys Lys Pro Thr Phe Lys Thr Thr
                245                 250                 255 aaa aaa gat ctc aaa cct caa acc act aaa cca aag gaa gta ccc acc      816
Lys Lys Asp Leu Lys Pro Gln Thr Thr Lys Pro Lys Glu Val Pro Thr
            260                 265                 270 acc aag tga                                                          825
Thr Lys  *

<210> SEQ ID NO 26
<211> LENGTH: 274
<212> TYPE: PRT
<213> ORGANISM: Artificial Sequence
<220> FEATURE:
<223> OTHER INFORMATION: :

<400> SEQUENCE: 26

Met Ser Asp Lys Ile Ile His Leu Thr Asp Asp Ser Phe Asp Thr Asp
 1               5                  10                  15

Val Leu Lys Ala Asp Gly Ala Ile Leu Val Asp Phe Trp Ala Glu Trp
```

```
                    20                  25                  30
Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His His Ser Ser Gly Leu Val Pro
        115                 120                 125

Arg Gly Ser Gly Met Lys Glu Thr Ala Ala Ala Lys Phe Glu Arg Gln
    130                 135                 140

His Met Asp Ser Pro Asp Leu Gly Thr Asp Asp Asp Lys Thr Gly
145                 150                 155                 160

Leu Leu Leu Asn His Gly Asp Ile Gly Ser Glu Phe Pro Thr Thr Val
                165                 170                 175

Lys Thr Lys Asn Thr Thr Thr Thr Gln Thr Gln Pro Ser Lys Pro Thr
            180                 185                 190

Thr Lys Gln Arg Gln Asn Lys Pro Pro Asn Lys Pro Asn Asn Asp Phe
        195                 200                 205

His Phe Glu Val Phe Asn Phe Val Pro Cys Ser Ile Cys Ser Asn Asn
    210                 215                 220

Pro Thr Cys Trp Ala Ile Cys Lys Arg Ile Pro Ala Lys Lys Pro Gly
225                 230                 235                 240

Lys Lys Thr Thr Thr Lys Pro Thr Lys Lys Pro Thr Phe Lys Thr Thr
                245                 250                 255

Lys Lys Asp Leu Lys Pro Gln Thr Thr Lys Pro Lys Glu Val Pro Thr
            260                 265                 270

Thr Lys

<210> SEQ ID NO 27
<211> LENGTH: 852
<212> TYPE: DNA
<213> ORGANISM: Artificial Sequence
<220> FEATURE:
<223> OTHER INFORMATION: RSV mutant fragment
<220> FEATURE:
<221> NAME/KEY: CDS
<222> LOCATION: (1)...(852)

<400> SEQUENCE: 27 atg ttc ctg ctg gct gtt ttc tac ggt ggt tcc gac aaa atc atc cac      48
Met Phe Leu Leu Ala Val Phe

```
                                                -continued

Val Ala Lys Leu Asn Ile Asp Gln Asn Pro Gly Thr Ala Pro Lys Tyr
 65                  70                  75                  80 ggc atc cgt ggt atc ccg act ctg ctg ttc aaa aac ggt gaa gtg       288
Gly Ile Arg Gly Ile Pro Thr Leu Leu Phe Lys Asn Gly Glu Val
                 85                  90                  95 gcg gca acc aaa gtg ggt gca ctg tct aaa ggt cag ttg aaa gag ttc   336
Ala Ala Thr Lys Val Gly Ala Leu Ser Lys Gly Gln Leu Lys Glu Phe
            100                 105                 110 ctc gac gct aac ctg gcc ggt tct ggt tct ggc cac atg cac cat cat   384
Leu Asp Ala Asn Leu Ala Gly Ser Gly Ser Gly His Met His His His
        115                 120                 125 cat cat cat tct tct ggt ctg gtg cca cgc ggt tct ggt atg aaa gaa   432
His His His Ser Ser Gly Leu Val Pro Arg Gly Ser Gly Met Lys Glu
130                 135                 140 acc gct gct gct aaa ttc gaa cgc cag cac atg gac agc cca gat ctg   480
Thr Ala Ala Ala Lys Phe Glu Arg Gln His Met Asp Ser Pro Asp Leu
145                 150                 155                 160 ggt acc gat gac gac gac aag acc ggg ctt ctc ctc aac cat ggc gat   528
Gly Thr Asp Asp Asp Asp Lys Thr Gly Leu Leu Leu Asn His Gly Asp
                165                 170                 175 atc gga tcc gaa ttc ccc aca aca gtc aag act aaa aac aca aca aca   576
Ile Gly Ser Glu Phe Pro Thr Thr Val Lys Thr Lys Asn Thr Thr Thr
            180                 185                 190 acc caa aca caa ccc agc aag ccc act aca aaa caa cgc caa aac aaa   624
Thr Gln Thr Gln Pro Ser Lys Pro Thr Thr Lys Gln Arg Gln Asn Lys
        195                 200                 205 cca cca aac aaa ccc aat aat gat ttt cac ttc gaa gtg ttt aac ttt   672
Pro Pro Asn Lys Pro Asn Asn Asp Phe His Phe Glu Val Phe Asn Phe
210                 215                 220 gta ccc tgc agc atc tgc agc aac aat cca acc tgc tgg gct atc tgc   720
Val Pro Cys Ser Ile Cys Ser Asn Asn Pro Thr Cys Trp Ala Ile Cys
225                 230                 235                 240 aaa aga ata cca aac aaa aaa cca gga aag aaa acc acc acc aag cct   768
Lys Arg Ile Pro Asn Lys Lys Pro Gly Lys Lys Thr Thr Thr Lys Pro
                245                 250                 255 aca aaa aaa cca acc ttc aag aca acc aaa aaa gat ctc aaa cct caa   816
Thr Lys Lys Pro Thr Phe Lys Thr Thr Lys Lys Asp Leu Lys Pro Gln
            260                 265                 270 acc act aaa cca aag gaa gta ccc acc acc aag tga                   852
Thr Thr Lys Pro Lys Glu Val Pro Thr Thr Lys *
        275                 280

<210> SEQ ID NO 28
<211> LENGTH: 283
<212> TYPE: PRT
<213> ORGANISM: Artificial Sequence
<220> FEATURE:
<223> OTHER INFORMATION: :

<400> SEQUENCE: 28

Met Phe Leu Leu Ala Val Phe Tyr Gly Gly Ser Asp Lys Ile Ile His
  1               5                  10                  15

Leu Thr Asp Asp Ser Phe Asp Thr Asp Val Leu Lys Ala Asp Gly Ala
             20                  25                  30

Ile Leu Val Asp Phe Trp Ala Glu Trp Cys Gly Pro Cys Lys Met Ile
         35                  40                  45

Ala Pro Ile Leu Asp Glu Ile Ala Asp Glu Tyr Gln Gly Lys Leu Thr
     50                  55                  60

Val Ala Lys Leu Asn Ile Asp Gln Asn Pro Gly Thr Ala Pro Lys Tyr
 65                  70                  75                  80
```

```
Gly Ile Arg Gly Ile Pro Thr Leu Leu Leu Phe Lys Asn Gly Glu Val
                85                  90                  95

Ala Ala Thr Lys Val Gly Ala Leu Ser Lys Gly Gln Leu Lys Glu Phe
            100                 105                 110

Leu Asp Ala Asn Leu Ala Gly Ser Gly Ser Gly His Met His His His
        115                 120                 125

His His Ser Ser Gly Leu Val Pro Arg Gly Ser Gly Met Lys Glu
    130                 135                 140

Thr Ala Ala Ala Lys Phe Glu Arg Gln His Met Asp Ser Pro Asp Leu
145                 150                 155                 160

Gly Thr Asp Asp Asp Asp Lys Thr Gly Leu Leu Leu Asn His Gly Asp
                165                 170                 175

Ile Gly Ser Glu Phe Pro Thr Thr Val Lys Thr Lys Asn Thr Thr Thr
            180                 185                 190

Thr Gln Thr Gln Pro Ser Lys Pro Thr Thr Lys Gln Arg Gln Asn Lys
        195                 200                 205

Pro Pro Asn Lys Pro Asn Asn Asp Phe His Phe Glu Val Phe Asn Phe
    210                 215                 220

Val Pro Cys Ser Ile Cys Ser Asn Asn Pro Thr Cys Trp Ala Ile Cys
225                 230                 235                 240

Lys Arg Ile Pro Asn Lys Lys Pro Gly Lys Lys Thr Thr Thr Lys Pro
                245                 250                 255

Thr Lys Lys Pro Thr Phe Lys Thr Thr Lys Lys Asp Leu Lys Pro Gln
            260                 265                 270

Thr Thr Lys Pro Lys Glu Val Pro Thr Thr Lys
        275                 280

<210> SEQ ID NO 29
<211> LENGTH: 852
<212> TYPE: DNA
<213> ORGANISM: Artificial Sequence
<220> FEATURE:
<223> OTHER INFORMATION: RSV mutant fragment
<220> FEATURE:
<221> NAME/KEY: CDS
<222> LOCATION: (1)...(852)

<400> SEQUENCE: 29 atg ttc ctg ctg gct gtt ttc tac ggt ggt tcc gac aaa atc atc cac      48
Met Phe Leu Leu Ala Val Phe Tyr Gly Gly Ser Asp Lys Ile Ile His
 1               5                  10                  15 ctg act gac gac agt ttt gac acg gat gta ctc aaa gcg gac ggg gcg      96
Leu Thr Asp Asp Ser Phe Asp Thr Asp Val Leu Lys Ala Asp Gly Ala
                20                  25                  30 atc ctc gtc gat ttc tgg gca gag tgg tgc ggt ccg tgc aaa atg atc     144
Ile Leu Val Asp Phe Trp Ala Glu Trp Cys Gly Pro Cys Lys Met Ile
            35                  40                  45 gcc ccg att ctg gat gaa atc gct gac gaa tat cag ggc aaa ctg acc     192
Ala Pro Ile Leu Asp Glu Ile Ala Asp Glu Tyr Gln Gly Lys Leu Thr
        50                  55                  60 gtt gca aaa ctg aac atc gat caa aac cct ggc act gcg ccg aaa tat     240
Val Ala Lys Leu Asn Ile Asp Gln Asn Pro Gly Thr Ala Pro Lys Tyr
 65                 70                  75                  80 ggc atc cgt ggt atc ccg act ctg ctg ctg ttc aaa aac ggt gaa gtg     288
Gly Ile Arg Gly Ile Pro Thr Leu Leu Leu Phe Lys Asn Gly Glu Val
                85                  90                  95 gcg gca acc aaa gtg ggt gca ctg tct aaa ggt cag ttg aaa gag ttc     336
Ala Ala Thr Lys Val Gly Ala Leu Ser Lys Gly Gln Leu Lys Glu Phe
            100                 105                 110
```

```
                  100                 105                 110
ctc gac gct aac ctg gcc ggt tct ggt tct ggc cac atg cac cat cat      384
Leu Asp Ala Asn Leu Ala Gly Ser Gly Ser Gly His Met His His His
            115                 120                 125 cat cat cat tct tct ggt ctg gtg cca cgc ggt tct ggt atg aaa gaa      432
His His His Ser Ser Gly Leu Val Pro Arg Gly Ser Gly Met Lys Glu
        130                 135                 140 acc gct gct gct aaa ttc gaa cgc cag cac atg gac agc cca gat ctg      480
Thr Ala Ala Ala Lys Phe Glu Arg Gln His Met Asp Ser Pro Asp Leu
145                 150                 155                 160 ggt acc gat gac gac gac aag acc ggg ctt ctc ctc aac cat ggc gat      528
Gly Thr Asp Asp Asp Asp Lys Thr Gly Leu Leu Leu Asn His Gly Asp
                165                 170                 175 atc gga tcc gaa ttc ccc aca aca gtc aag act aaa aac aca aca aca      576
Ile Gly Ser Glu Phe Pro Thr Thr Val Lys Thr Lys Asn Thr Thr Thr
            180                 185                 190 acc caa aca caa ccc agc aag ccc act aca aaa caa cgc caa aac aaa      624
Thr Gln Thr Gln Pro Ser Lys Pro Thr Thr Lys Gln Arg Gln Asn Lys
        195                 200                 205 cca cca aac aaa ccc aat aat gat ttt cac ttc gaa gtg ttt aac ttt      672
Pro Pro Asn Lys Pro Asn Asn Asp Phe His Phe Glu Val Phe Asn Phe
    210                 215                 220 gta ccc tgc agc atc tgc agc aac aat cca acc tgc tgg gct atc tgc      720
Val Pro Cys Ser Ile Cys Ser Asn Asn Pro Thr Cys Trp Ala Ile Cys
225                 230                 235                 240 aaa aga ata cca gct aaa aaa cca gga aag aaa acc acc acc aag cct      768
Lys Arg Ile Pro Ala Lys Lys Pro Gly Lys Lys Thr Thr Thr Lys Pro
                245                 250                 255 aca aaa aaa cca acc ttc aag aca acc aaa aaa gat ctc aaa cct caa      816
Thr Lys Lys Pro Thr Phe Lys Thr Thr Lys Lys Asp Leu Lys Pro Gln
            260                 265                 270 acc act aaa cca aag gaa gta ccc acc acc aag tga                      852
Thr Thr Lys Pro Lys Glu Val Pro Thr Thr Lys *
        275                 280

<210> SEQ ID NO 30
<211> LENGTH: 283
<212> TYPE: PRT
<213> ORGANISM: Artificial Sequence
<220> FEATURE:
<223> OTHER INFORMATION: :

<400> SEQUENCE: 30

Met Phe Leu Leu Ala Val Phe Tyr Gly Gly Ser Asp Lys Ile Ile His
 1               5                  10                  15

Leu Thr Asp Asp Ser Phe Asp Thr Asp Val Leu Lys Ala Asp Gly Ala
            20                  25                  30

Ile Leu Val Asp Phe Trp Ala Glu Trp Cys Gly Pro Cys Lys Met Ile
        35                  40                  45

Ala Pro Ile Leu Asp Glu Ile Ala Asp Glu Tyr Gln Gly Lys Leu Thr
    50                  55                  60

Val Ala Lys Leu Asn Ile Asp Gln Asn Pro Gly Thr Ala Pro Lys Tyr
65                  70                  75                  80

Gly Ile Arg Gly Ile Pro Thr Leu Leu Leu Phe Lys Asn Gly Glu Val
                85                  90                  95

Ala Ala Thr Lys Val Gly Ala Leu Ser Lys Gly Gln Leu Lys Glu Phe
            100                 105                 110

Leu Asp Ala Asn Leu Ala Gly Ser Gly Ser Gly His Met His His His
        115                 120                 125
```

```
His His His Ser Ser Gly Leu Val Pro Arg Gly Ser Gly Met Lys Glu
        130                 135                 140

Thr Ala Ala Lys Phe Glu Arg Gln His Met Asp Ser Pro Asp Leu
145                 150                 155                 160

Gly Thr Asp Asp Asp Lys Thr Gly Leu Leu Asn His Gly Asp
            165                 170                 175

Ile Gly Ser Glu Phe Pro Thr Thr Val Lys Thr Lys Asn Thr Thr Thr
                180                 185                 190

Thr Gln Thr Gln Pro Ser Lys Pro Thr Thr Lys Gln Arg Gln Asn Lys
            195                 200                 205

Pro Pro Asn Lys Pro Asn Asn Asp Phe His Phe Glu Val Phe Asn Phe
        210                 215                 220

Val Pro Cys Ser Ile Cys Ser Asn Asn Pro Thr Cys Trp Ala Ile Cys
225                 230                 235                 240

Lys Arg Ile Pro Ala Lys Lys Pro Gly Lys Lys Thr Thr Thr Lys Pro
                245                 250                 255

Thr Lys Lys Pro Thr Phe Lys Thr Thr Lys Lys Asp Leu Lys Pro Gln
            260                 265                 270

Thr Thr Lys Pro Lys Glu Val Pro Thr Thr Lys
        275                 280

<210> SEQ ID NO 31
<211> LENGTH: 852
<212> TYPE: DNA
<213> ORGANISM: Artificial Sequence
<220> FEATURE:
<223> OTHER INFORMATION: RSV mutant fragment
<220> FEATURE:
<221> NAME/KEY: CDS
<222> LOCATION: (1)...(852)

<400> SEQUENCE: 31 atg tcc gac aaa atc atc cac ctg act gac gac agt ttt gac acg gat      48
Met Ser Asp Lys Ile Ile His Leu Thr Asp Asp Ser Phe Asp Thr Asp
1               5                   10                  15 gta ctc aaa gcg gac ggg gcg atc ctc gtc gat ttc tgg gca gag tgg      96
Val Leu Lys Ala Asp Gly Ala Ile Leu Val Asp Phe Trp Ala Glu Trp
            20                  25                  30 tgc ggt ccg tgc aaa atg atc gcc ccg att ctg gat gaa atc gct gac     144
Cys Gly Pro Cys Lys Met Ile Ala Pro Ile Leu Asp Glu Ile Ala Asp
        35                  40                  45 gaa tat cag ggc aaa ctg acc gtt gca aaa ctg aac atc gat caa aac     192
Glu Tyr Gln Gly Lys Leu Thr Val Ala Lys Leu Asn Ile Asp Gln Asn
    50                  55                  60 cct ggc act gcg ccg aaa tat ggc atc cgt ggt atc ccg act ctg ctg     240
Pro Gly Thr Ala Pro Lys Tyr Gly Ile Arg Gly Ile Pro Thr Leu Leu
65                  70                  75                  80 ctg ttc aaa aac ggt gaa gtg gcg gca acc aaa gtg ggt gca ctg tct     288
Leu Phe Lys Asn Gly Glu Val Ala Ala Thr Lys Val Gly Ala Leu Ser
                85                  90                  95 aaa ggt cag ttg aaa gag ttc ctc gac gct aac ctg gcc ggt tct ggt     336
Lys Gly Gln Leu Lys Glu Phe Leu Asp Ala Asn Leu Ala Gly Ser Gly
            100                 105                 110 tct ggc cac atg cac cat cat cat cat cat tct tct ggt ctg gtg cca     384
Ser Gly His Met His His His His His His Ser Ser Gly Leu Val Pro
        115                 120                 125 cgc ggt tct ggt atg aaa gaa acc gct gct gct aaa ttc gaa cgc cag     432
Arg Gly Ser Gly Met Lys Glu Thr Ala Ala Ala Lys Phe Glu Arg Gln
130                 135                 140
```

```
cac atg gac agc cca gat ctg ggt acc gat gac gac aag acc ggg         480
His Met Asp Ser Pro Asp Leu Gly Thr Asp Asp Asp Lys Thr Gly
145                 150                 155                 160 ctt ctc ctc aac cat ggc gat atc gga tcc gaa ttc ccc aca aca gtc     528
Leu Leu Leu Asn His Gly Asp Ile Gly Ser Glu Phe Pro Thr Thr Val
                165                 170                 175 aag act aaa aac aca aca aca acc caa aca caa ccc agc aag ccc act     576
Lys Thr Lys Asn Thr Thr Thr Thr Gln Thr Gln Pro Ser Lys Pro Thr
            180                 185                 190 aca aaa caa cgc caa aac aaa cca cca aac aaa ccc aat aat gat ttt     624
Thr Lys Gln Arg Gln Asn Lys Pro Pro Asn Lys Pro Asn Asn Asp Phe
        195                 200                 205 cac ttc gaa gtg ttt aac ttt gta ccc tgc agc atc tgc agc aac aat     672
His Phe Glu Val Phe Asn Phe Val Pro Cys Ser Ile Cys Ser Asn Asn
    210                 215                 220 cca acc tgc tgg gct atc tgc aaa aga ata cca aac aaa aaa cca gga     720
Pro Thr Cys Trp Ala Ile Cys Lys Arg Ile Pro Asn Lys Lys Pro Gly
225                 230                 235                 240 aag aaa acc acc acc aag cct aca aaa aaa cca acc ttc aag aca acc     768
Lys Lys Thr Thr Thr Lys Pro Thr Lys Lys Pro Thr Phe Lys Thr Thr
                245                 250                 255 aaa aaa gat ctc aaa cct caa acc act aaa cca aag gaa gta ccc acc     816
Lys Lys Asp Leu Lys Pro Gln Thr Thr Lys Pro Lys Glu Val Pro Thr
            260                 265                 270 acc aag ggt ggt tac ttc gtt gct ctg ctg ttc taa                     852
Thr Lys Gly Gly Tyr Phe Val Ala Leu Leu Phe  *
        275                 280
```

<210> SEQ ID NO 32
<211> LENGTH: 283
<212> TYPE: PRT
<213> ORGANISM: Artificial Sequence
<220> FEATURE:
<223> OTHER INFORMATION: :

<400> SEQUENCE: 32

```
Met Ser Asp Lys Ile Ile His Leu Thr Asp Ser Phe Asp Thr Asp
 1               5                  10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His Ser Ser Gly Leu Val Pro
        115                 120                 125

Arg Gly Ser Gly Met Lys Glu Thr Ala Ala Ala Lys Phe Glu Arg Gln
130                 135                 140

His Met Asp Ser Pro Asp Leu Gly Thr Asp Asp Asp Lys Thr Gly
145                 150                 155                 160

Leu Leu Leu Asn His Gly Asp Ile Gly Ser Glu Phe Pro Thr Thr Val
                165                 170                 175
```

```
Lys Thr Lys Asn Thr Thr Thr Thr Gln Thr Gln Pro Ser Lys Pro Thr
            180                 185                 190

Thr Lys Gln Arg Gln Asn Lys Pro Pro Asn Lys Pro Asn Asn Asp Phe
        195                 200                 205

His Phe Glu Val Phe Asn Phe Val Pro Cys Ser Ile Cys Ser Asn Asn
    210                 215                 220

Pro Thr Cys Trp Ala Ile Cys Lys Arg Ile Pro Asn Lys Lys Pro Gly
225                 230                 235                 240

Lys Lys Thr Thr Thr Lys Pro Thr Lys Pro Thr Phe Lys Thr Thr
                245                 250                 255

Lys Lys Asp Leu Lys Pro Gln Thr Thr Lys Pro Lys Glu Val Pro Thr
            260                 265                 270

Thr Lys Gly Gly Tyr Phe Val Ala Leu Leu Phe
        275                 280

<210> SEQ ID NO 33
<211> LENGTH: 852
<212> TYPE: DNA
<213> ORGANISM: Artificial Sequence
<220> FEATURE:
<223> OTHER INFORMATION: RSV mutant fragment
<220> FEATURE:
<221> NAME/KEY: CDS
<222> LOCATION: (1)...(852)

<400> SEQUENCE: 33 atg tcc gac aaa atc atc cac ctg act gac gac agt ttt gac acg gat     48
Met Ser Asp Lys Ile Ile His Leu Thr Asp Asp Ser Phe Asp Thr Asp
  1               5                  10                  15 gta ctc aaa gcg gac ggg gcg atc ctc gtc gat ttc tgg gca gag tgg    96
Val Leu Lys Ala Asp Gly Ala Ile Leu Val Asp Phe Trp Ala Glu Trp
                 20                  25                  30 tgc ggt ccg tgc aaa atg atc gcc ccg att ctg gat gaa atc gct gac   144
Cys Gly Pro Cys Lys Met Ile Ala Pro Ile Leu Asp Glu Ile Ala Asp
             35                  40                  45 gaa tat cag ggc aaa ctg acc gtt gca aaa ctg aac atc gat caa aac   192
Glu Tyr Gln Gly Lys Leu Thr Val Ala Lys Leu Asn Ile Asp Gln Asn
         50                  55                  60 cct ggc act gcg ccg aaa tat ggc atc cgt ggt atc ccg act ctg ctg   240
Pro Gly Thr Ala Pro Lys Tyr Gly Ile Arg Gly Ile Pro Thr Leu Leu
 65                  70                  75                  80 ctg ttc aaa aac ggt gaa gtg gcg gca acc aaa gtg ggt gca ctg tct   288
Leu Phe Lys Asn Gly Glu Val Ala Ala Thr Lys Val Gly Ala Leu Ser
                 85                  90                  95 aaa ggt cag ttg aaa gag ttc ctc gac gct aac ctg gcc ggt tct ggt   336
Lys Gly Gln Leu Lys Glu Phe Leu Asp Ala Asn Leu Ala Gly Ser Gly
                100                 105                 110 tct ggc cac atg cac cat cat cat cat cat tct tct ggt ctg gtg cca   384
Ser Gly His Met His His His His His His Ser Ser Gly Leu Val Pro
            115                 120                 125 cgc ggt tct ggt atg aaa gaa acc gct gct gct aaa ttc gaa cgc cag   432
Arg Gly Ser Gly Met Lys Glu Thr Ala Ala Ala Lys Phe Glu Arg Gln
        130                 135                 140 cac atg gac agc cca gat ctg ggt acc gat gac gac gac aag acc ggg   480
His Met Asp Ser Pro Asp Leu Gly Thr Asp Asp Asp Asp Lys Thr Gly
145                 150                 155                 160 ctt ctc ctc aac cat ggc gat atc gga tcc gaa ttc ccc aca aca gtc   528
Leu Leu Leu Asn His Gly Asp Ile Gly Ser Glu Phe Pro Thr Thr Val
                165                 170                 175
```

```
aag act aaa aac aca aca aca acc caa aca caa ccc agc aag ccc act    576
Lys Thr Lys Asn Thr Thr Thr Thr Gln Thr Gln Pro Ser Lys Pro Thr
            180                 185                 190 aca aaa caa cgc caa aac aaa cca cca aac aaa ccc aat aat gat ttt    624
Thr Lys Gln Arg Gln Asn Lys Pro Pro Asn Lys Pro Asn Asn Asp Phe
            195                 200                 205 cac ttc gaa gtg ttt aac ttt gta ccc tgc agc atc tgc agc aac aat    672
His Phe Glu Val Phe Asn Phe Val Pro Cys Ser Ile Cys Ser Asn Asn
    210                 215                 220 cca acc tgc tgg gct atc tgc aaa aga ata cca gct aaa aaa cca gga    720
Pro Thr Cys Trp Ala Ile Cys Lys Arg Ile Pro Ala Lys Lys Pro Gly
225                 230                 235                 240 aag aaa acc acc acc aag cct aca aaa aaa cca acc ttc aag aca acc    768
Lys Lys Thr Thr Thr Lys Pro Thr Lys Lys Pro Thr Phe Lys Thr Thr
                245                 250                 255 aaa aaa gat ctc aaa cct caa acc act aaa cca aag gaa gta ccc acc    816
Lys Lys Asp Leu Lys Pro Gln Thr Thr Lys Pro Lys Glu Val Pro Thr
            260                 265                 270 acc aag ggt ggt tac ttc gtt gct ctg ctg ttc taa                    852
Thr Lys Gly Gly Tyr Phe Val Ala Leu Leu Phe *
            275                 280
```

<210> SEQ ID NO 34
<211> LENGTH: 283
<212> TYPE: PRT
<213> ORGANISM: Artificial Sequence
<220> FEATURE:
<223> OTHER INFORMATION: :

<400> SEQUENCE: 34

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His Ser Ser Gly Leu Val Pro
        115                 120                 125

Arg Gly Ser Gly Met Lys Glu Thr Ala Ala Ala Lys Phe Glu Arg Gln
    130                 135                 140

His Met Asp Ser Pro Asp Leu Gly Thr Asp Asp Asp Lys Thr Gly
145                 150                 155                 160

Leu Leu Leu Asn His Gly Asp Ile Gly Ser Glu Phe Pro Thr Thr Val
                165                 170                 175

Lys Thr Lys Asn Thr Thr Thr Gln Thr Gln Pro Ser Lys Pro Thr
            180                 185                 190

Thr Lys Gln Arg Gln Asn Lys Pro Pro Asn Lys Pro Asn Asn Asp Phe
        195                 200                 205

His Phe Glu Val Phe Asn Phe Val Pro Cys Ser Ile Cys Ser Asn Asn
    210                 215                 220
```

-continued

```
Pro Thr Cys Trp Ala Ile Cys Lys Arg Ile Pro Ala Lys Lys Pro Gly
225                 230                 235                 240

Lys Lys Thr Thr Thr Lys Pro Thr Lys Pro Thr Phe Lys Thr Thr
            245                 250                 255

Lys Lys Asp Leu Lys Pro Gln Thr Thr Lys Pro Lys Glu Val Pro Thr
        260                 265                 270

Thr Lys Gly Gly Tyr Phe Val Ala Leu Leu Phe
        275                 280

<210> SEQ ID NO 35
<211> LENGTH: 10
<212> TYPE: PRT
<213> ORGANISM: Artificial Sequence
<220> FEATURE:
<223> OTHER INFORMATION: Hydrophobic anchor

<400> SEQUENCE: 35

Met Phe Leu Leu Ala Val Phe Tyr Gly Gly
 1               5                  10

<210> SEQ ID NO 36
<211> LENGTH: 9
<212> TYPE: PRT
<213> ORGANISM: Artificial Sequence
<220> FEATURE:
<223> OTHER INFORMATION: Hydrophobic anchor

<400> SEQUENCE: 36

Gly Gly Tyr Phe Val Ala Leu Leu Phe
 1               5

<210> SEQ ID NO 37
<211> LENGTH: 43
<212> TYPE: DNA
<213> ORGANISM: Artificial Sequence
<220> FEATURE:
<223> OTHER INFORMATION: Primer for the G128-229, I185A mutant

<400> SEQUENCE: 37
cctgctgggc tgcctgcaaa agaataccaa acaaaaaacc agg                          43

<210> SEQ ID NO 38
<211> LENGTH: 43
<212> TYPE: DNA
<213> ORGANISM: Artificial Sequence
<220> FEATURE:
<223> OTHER INFORMATION: Primer for the G128-229, I185A mutant

<400> SEQUENCE: 38
cctggttttt tgtttggtat tcttttgcag gcagcccagc agg                          43

<210> SEQ ID NO 39
<211> LENGTH: 42
<212> TYPE: DNA
<213> ORGANISM: Artificial Sequence
<220> FEATURE:
<223> OTHER INFORMATION: Primer for the G128-229, C186A mutant

<400> SEQUENCE: 39
ctgctgggct atcgccaaaa gaataccaaa caaaaaacca gg                           42

<210> SEQ ID NO 40
<211> LENGTH: 42
<212> TYPE: DNA
```

-continued

<210> SEQ ID NO 41
<211> LENGTH: 42
<212> TYPE: DNA
<213> ORGANISM: Artificial Sequence
<220> FEATURE:
<223> OTHER INFORMATION: Primer for the G128-229, C186A mutant

<400> SEQUENCE: 40
cctggttttt tgtttggtat tcttttggcg atagcccagc ag                42

<210> SEQ ID NO 41
<211> LENGTH: 42
<212> TYPE: DNA
<213> ORGANISM: Artificial Sequence
<220> FEATURE:
<223> OTHER INFORMATION: Primer for the G128-229, K187A mutant

<400> SEQUENCE: 41
ctgctgggct atctgcgcaa gataccaaa caaaaaacca gg                 42

<210> SEQ ID NO 42
<211> LENGTH: 42
<212> TYPE: DNA
<213> ORGANISM: Artificial Sequence
<220> FEATURE:
<223> OTHER INFORMATION: Primer for the G128-229, K187A mutant

<400> SEQUENCE: 42
cctggttttt tgtttggtat tcttgcgcag atagcccagc ag                42

<210> SEQ ID NO 43
<211> LENGTH: 42
<212> TYPE: DNA
<213> ORGANISM: Artificial Sequence
<220> FEATURE:
<223> OTHER INFORMATION: Primer for the G128-229, R188A mutant

<400> SEQUENCE: 43
ctgctgggct atctgcaaag caataccaaa caaaaaacca gg                42

<210> SEQ ID NO 44
<211> LENGTH: 42
<212> TYPE: DNA
<213> ORGANISM: Artificial Sequence
<220> FEATURE:
<223> OTHER INFORMATION: Primer for the G128-229, R188A mutant

<400> SEQUENCE: 44
cctggttttt tgtttggtat tgctttgcag atagcccagc ag                42

<210> SEQ ID NO 45
<211> LENGTH: 42
<212> TYPE: DNA
<213> ORGANISM: Artificial Sequence
<220> FEATURE:
<223> OTHER INFORMATION: Primer for the G128-229, I189A mutant

<400> SEQUENCE: 45
ctgctgggct atctgcaaaa gagcaccaaa caaaaaacca gg                42

<210> SEQ ID NO 46
<211> LENGTH: 42
<212> TYPE: DNA
<213> ORGANISM: Artificial Sequence
<220> FEATURE:
<223> OTHER INFORMATION: Primer for the G128-229, I189A mutant

<400> SEQUENCE: 46
cctggttttt tgtttggtgc tcttttgcag atagcccagc ag                42

<210> SEQ ID NO 47
<211> LENGTH: 42
<212> TYPE: DNA
<213> ORGANISM: Artificial Sequence
<220> FEATURE:
<223> OTHER INFORMATION: Primer for the G128-229, P190A mutant

<400> SEQUENCE: 47
ctgctgggct atctgcaaaa gaatagcaaa caaaaaacca gg                42

<210> SEQ ID NO 48
<211> LENGTH: 42
<212> TYPE: DNA
<213> ORGANISM: Artificial Sequence
<220> FEATURE:
<223> OTHER INFORMATION: Primer for the G128-229, P190A mutant

<400> SEQUENCE: 48
cctggttttt tgtttgctat tcttttgcag atagcccagc ag                42

<210> SEQ ID NO 49
<211> LENGTH: 43
<212> TYPE: DNA
<213> ORGANISM: Artificial Sequence
<220> FEATURE:
<223> OTHER INFORMATION: Primer for the G128-229, N191A mutant

<400> SEQUENCE: 49
ctgcaaaaga ataccagcca aaaaccagg aaagaaaacc acc                43

<210> SEQ ID NO 50
<211> LENGTH: 43
<212> TYPE: DNA
<213> ORGANISM: Artificial Sequence
<220> FEATURE:
<223> OTHER INFORMATION: Primer for the G128-229, N191A mutant

<400> SEQUENCE: 50
ggtggttttc ttcctggtt ttttggctgg tattcttttg cag                43

<210> SEQ ID NO 51
<211> LENGTH: 43
<212> TYPE: DNA
<213> ORGANISM: Artificial Sequence
<220> FEATURE:
<223> OTHER INFORMATION: Primer for the G128-229, K192A mutant

<400> SEQUENCE: 51
ctgggctatc tgcaaaagaa taccaaacgc aaaaccagga aag                43

<210> SEQ ID NO 52
<211> LENGTH: 43
<212> TYPE: DNA
<213> ORGANISM: Artificial Sequence
<220> FEATURE:
<223> OTHER INFORMATION: Primer for the G128-229, K192A mutant

<400> SEQUENCE: 52
ctttcctggt tttgcgtttg gtattctttt gcagatagcc cag                43

<210> SEQ ID NO 53
<211> LENGTH: 43
<212> TYPE: DNA
<213> ORGANISM: Artificial Sequence
<220> FEATURE:

<223> OTHER INFORMATION: Primer for the G128-229, K193A mutant

<400> SEQUENCE: 53

```
gcaaagaat accaaacaaa gcaccaggaa agaaaaccac cac                    43
```

<210> SEQ ID NO 54
<211> LENGTH: 43
<212> TYPE: DNA
<213> ORGANISM: Artificial Sequence
<220> FEATURE:
<223> OTHER INFORMATION: Primer for the G128-229, K193A mutant

<400> SEQUENCE: 54

```
gtggtggttt tctttcctgg tgctttgttt ggtattcttt tgc                   43
```

<210> SEQ ID NO 55
<211> LENGTH: 306
<212> TYPE: DNA
<213> ORGANISM: Artificial Sequence
<220> FEATURE:
<223> OTHER INFORMATION: RSV mutant fragment

<400> SEQUENCE: 55

```
cccacaacag tcaagactaa aaacacaaca acaacccaaa cacaacccag caagcccact    60
acaaaacaac gccaaaacaa accaccaaac aaacccaata atgattttca cttcgaagtg   120
tttaactttg taccctgcag catatgcagc aacaatccaa cctgctgggc tatctgcaaa   180
agaatagcag ccaaaaaacc aggaaagaaa accaccacca gcctacaaa aaaaccaacc   240 ttcaagacaa ccaaaaaaga tcacaaacct caaaccacta aaccaaagga agtacccacc   300
accaag                                                              306
```

<210> SEQ ID NO 56
<211> LENGTH: 102
<212> TYPE: PRT
<213> ORGANISM: Artificial Sequence
<220> FEATURE:
<223> OTHER INFORMATION: RSV mutant fragment

<400> SEQUENCE: 56

```
Pro Thr Thr Val Lys Thr Lys Asn Thr Thr Thr Gln Thr Gln Pro
 1               5                  10                  15

Ser Lys Pro Thr Thr Lys Gln Arg Gln Asn Lys Pro Asn Lys Pro
            20                  25                  30

Asn Asn Asp Phe His Phe Glu Val Phe Asn Phe Val Pro Cys Ser Ile
        35                  40                  45

Cys Ser Asn Asn Pro Thr Cys Trp Ala Ile Cys Lys Arg Ile Ala Ala
    50                  55                  60

Lys Lys Pro Gly Lys Lys Thr Thr Thr Lys Pro Thr Lys Lys Pro Thr
65                  70                  75                  80

Phe Lys Thr Thr Lys Lys Asp His Lys Pro Gln Thr Thr Lys Pro Lys
                85                  90                  95

Glu Val Pro Thr Thr Lys
            100
```

<210> SEQ ID NO 57
<211> LENGTH: 306
<212> TYPE: DNA
<213> ORGANISM: Artificial Sequence
<220> FEATURE:
<223> OTHER INFORMATION: RSV mutant fragment

```
<400> SEQUENCE: 57
cccacaacag tcaagactaa aaacacaaca acaacccaaa cacaacccag caagcccact    60
acaaaacaac gccaaaacaa accaccaaac aaacccaata atgattttca cttcgaagtg   120
tttaactttg taccctgcag catatgcagc aacaatccaa cctgctgggc tatctgcaaa   180
gcaataccag ccaaaaaacc aggaaagaaa accaccacca agcctacaaa aaaaccaacc   240
ttcaagacaa ccaaaaaaga tcacaaacct caaaccacta aaccaaagga agtacccacc   300
accaag                                                             306

<210> SEQ ID NO 58
<211> LENGTH: 102
<212> TYPE: PRT
<213> ORGANISM: Artificial Sequence
<220> FEATURE:
<223> OTHER INFORMATION: RSV mutant fragment

<400> SEQUENCE: 58

Pro Thr Thr Val Lys Thr Lys Asn Thr Thr Thr Thr Gln Thr Gln Pro
 1               5                   10                  15

Ser Lys Pro Thr Thr Lys Gln Arg Gln Asn Lys Pro Pro Asn Lys Pro
            20                   25                  30

Asn Asn Asp Phe His Phe Glu Val Phe Asn Phe Val Pro Cys Ser Ile
        35                   40                  45

Cys Ser Asn Asn Pro Thr Cys Trp Ala Ile Cys Lys Ala Ile Pro Ala
    50                   55                  60

Lys Lys Pro Gly Lys Lys Thr Thr Thr Lys Pro Thr Lys Lys Pro Thr
65                  70                  75                  80

Phe Lys Thr Thr Lys Lys Asp His Lys Pro Gln Thr Thr Lys Pro Lys
                85                  90                  95

Glu Val Pro Thr Thr Lys
            100

<210> SEQ ID NO 59
<211> LENGTH: 306
<212> TYPE: DNA
<213> ORGANISM: Artificial Sequence
<220> FEATURE:
<223> OTHER INFORMATION: RSV mutant f

```
Ser Lys Pro Thr Thr Lys Gln Arg Gln Asn Lys Pro Asn Lys Pro
            20                  25                  30

Asn Asn Asp Phe His Phe Glu Val Phe Asn Phe Val Pro Cys Ser Ile
        35                  40                  45

Cys Ser Ala Asn Pro Thr Cys Trp Ala Ile Cys Lys Arg Ile Pro Asn
 50                  55                  60

Lys Lys Pro Gly Lys Lys Thr Thr Thr Lys Pro Thr Lys Lys Pro Thr
 65                  70                  75                  80

Phe Lys Thr Thr Lys Lys Asp His Lys Pro Gln Thr Thr Lys Pro Lys
                85                  90                  95

Glu Val Pro Thr Thr Lys
            100
```

```
<210> SEQ ID NO 61
<211> LENGTH: 306
<212> TYPE: DNA
<213> ORGANISM: Artificial Sequence
<220> FEATURE:
<223> OTHER INFORMATION: RSV mutant fragment

<400> SEQUENCE: 61
cccacaacag tcaagactaa aaacacaaca acaacccaaa cacaacccag caagcccact      60
acaaaacaac gccaaaacaa accaccaaac aaacccaata atgattttca cttcgaagtg     120
tttaactttg taccctgcag catatgcagc aacgctccaa cctgctgggc tatctgcaaa     180
agaataccaa caaaaaaacc aggaaagaaa accaccacca agcctacaaa aaaaccaacc     240
ttcaagacaa ccaaaaaaga tcacaaacct caaaccacta aaccaaagga agtacccacc     300
accaag                                                                306
```

```
<210> SEQ ID NO 62
<211> LENGTH: 102
<212> TYPE: PRT
<213> ORGANISM: Artificial Sequence
<220> FEATURE:
<223> OTHER INFORMATION: RSV mutant fragment

<400> SEQUENCE: 62

Pro Thr Thr Val Lys Thr Lys Asn Thr Thr Thr Thr Gln Thr Gln Pro
 1               5                  10                  15

Ser Lys Pro Thr Thr Lys Gln Arg Gln Asn Lys Pro Asn Lys Pro
            20                  25                  30

Asn Asn Asp Phe His Phe Glu Val Phe Asn Phe Val Pro Cys Ser Ile
        35                  40                  45

Cys Ser Ala Asn Pro Thr Cys Trp Ala Ile Cys Lys Arg Ile Pro Asn
 50                  55                  60

Lys Lys Pro Gly Lys Lys Thr Thr Thr Lys Pro Thr Lys Lys Pro Thr
 65                  70                  75                  80

Phe Lys Thr Thr Lys Lys Asp His Lys Pro Gln Thr Thr Lys Pro Lys
                85                  90                  95

Glu Val Pro Thr Thr Lys
            100
```

```
<210> SEQ ID NO 63
<211> LENGTH: 306
<212> TYPE: DNA
<213> ORGANISM: Artificial Sequence
<220> FEATURE:
<223> OTHER INFORMATION: RSV mutant fragment
```

<400> SEQUENCE: 63

```
cccacaacag tcaagactaa aaacacaaca acaacccaaa cacaacccag caagcccact    60
acaaaacaac gccaaaacaa accaccaaac aaacccaata atgattttca cttcgaagtg   120
tttaactttg taccctgcag catatgcagc aacaatccaa cctgctgggc tatctgcaaa   180
agaataccaa acaaaaaacc aggagcgaaa accaccacca agcctacaaa aaaaccaacc   240
ttcaagacaa ccaaaaaaga tcacaaacct caaaccacta aaccaaagga agtacccacc   300
accaag                                                             306
```

<210> SEQ ID NO 64
<211> LENGTH: 102
<212> TYPE: PRT
<213> ORGANISM: Artificial Sequence
<220> FEATURE:
<223> OTHER INFORMATION: RSV mutant fragment

<400> SEQUENCE: 64

Pro Thr Thr Val Lys Thr Lys Asn Thr Thr Thr Thr Gln Thr Gln Pro
1               5                   10                  15

Ser Lys Pro Thr Thr Lys Gln Arg Gln Asn Lys Pro Pro Asn Lys Pro
                20                  25                  30

Asn Asn Asp Phe His Phe Glu Val Phe Asn Phe Val Pro Cys Ser Ile
            35                  40                  45

Cys Ser Asn Asn Pro Thr Cys Trp Ala Ile Cys Lys Arg Ile Pro Asn
        50                  55                  60

Lys Lys Pro Gly Ala Lys Thr Thr Thr Lys Pro Thr Lys Lys Pro Thr
65                  70                  75                  80

Phe Lys Thr Thr Lys Lys Asp His Lys Pro Gln Thr Thr Lys Pro Lys
                85                  90                  95

Glu Val Pro Thr Thr Lys
            100

<210> SEQ ID NO 65
<211> LENGTH: 306
<212> TYPE: DNA
<213> ORGANISM: Artificial Sequence
<220> FEATURE:
<223> OTHER INFORMATION: RSV mutant fragment

<400> SEQUENCE: 65

```
cccacaacag tcaagactaa aaacacaaca acaacccaaa cacaacccag caagcccact    60
acaaaacaac gccaaaacaa accaccaaac aaacccaata atgattttca cttcgaagtg   120
tttaactttg taccctgcag catatgcagc aacaatccaa cctgctgggc tatctgcaaa   180
agaataccaa acaaaaaacc aggaaaggca accaccacca agcctacaaa aaaaccaacc   240
ttcaagacaa ccaaaaaaga tcacaaacct caaaccacta aaccaaagga agtacccacc   300
accaag                                                             306
```

<210> SEQ ID NO 66
<211> LENGTH: 102
<212> TYPE: PRT
<213> ORGANISM: Artificial Sequence
<220> FEATURE:
<223> OTHER INFORMATION: RSV mutant fragment

<400> SEQUENCE: 66

Pro Thr Thr Val Lys Thr Lys Asn Thr Thr Thr Thr Gln Thr Gln Pro

```
            1               5               10              15
Ser Lys Pro Thr Thr Lys Gln Arg Gln Asn Lys Pro Pro Asn Lys Pro
                20                  25                  30

Asn Asn Asp Phe His Phe Glu Val Phe Asn Phe Val Pro Cys Ser Ile
                35                  40                  45

Cys Ser Asn Asn Pro Thr Cys Trp Ala Ile Cys Lys Arg Ile Pro Asn
            50                  55                  60

Lys Lys Pro Gly Lys Ala Thr Thr Thr Lys Pro Thr Lys Lys Pro Thr
65                  70                  75                  80

Phe Lys Thr Thr Lys Lys Asp His Lys Pro Gln Thr Thr Lys Pro Lys
                    85                  90                  95

Glu Val Pro Thr Thr Lys
                100
```

<210> SEQ ID NO 67
<211> LENGTH: 306
<212> TYPE: DNA
<213> ORGANISM: Artificial Sequence
<220> FEATURE:
<223> OTHER INFORMATION: RSV mutant fragment

<400> SEQUENCE: 67

```
cccacaacag tcaagactaa aaacacaaca acaacccaaa cacaacccag caagcccact     60
acaaaacaac gccaaaacaa accaccaaac aaacccaata atgattttca cttcgaagtg    120
tttaactttg taccctgcag catatgcagc aacaatccaa cctgctgggc tatctgcaaa    180
agaataccaa acaaaaaacc aggaaagaaa accaccacca agcctacagc aaaaccaacc    240
ttcaagacaa ccaaaaaaga tcacaaacct caaaccacta accaaggaa agtacccacc    300
accaag                                                              306
```

<210> SEQ ID NO 68
<211> LENGTH: 102
<212> TYPE: PRT
<213> ORGANISM: Artificial Sequence
<220> FEATURE:
<223> OTHER INFORMATION: RSV mutant fragment

<400> SEQUENCE: 68

```
Pro Thr Thr Val Lys Thr Lys Asn Thr Thr Thr Thr Gln Thr Gln Pro
1               5                   10                  15

Ser Lys Pro Thr Thr Lys Gln Arg Gln Asn Lys Pro Pro Asn Lys Pro
                20                  25                  30

Asn Asn Asp Phe His Phe Glu Val Phe Asn Phe Val Pro Cys Ser Ile
                35                  40                  45

Cys Ser Asn Asn Pro Thr Cys Trp Ala Ile Cys Lys Arg Ile Pro Asn
            50                  55                  60

Lys Lys P

```
<223> OTHER INFORMATION: RSV mutant fragment

<400> SEQUENCE: 69
cccacaacag tcaagactaa aaacacaaca acaacccaaa cacaacccag caagcccact      60
acaaaacaac gccaaaacaa accaccaaac aaacccaata atgattttca cttcgaagtg     120
tttaactttg taccctgcag catatgcagc aacaatccaa cctgctgggc tatctgcaaa    180
agaataccaa acaaaaaacc aggaaagaaa accaccacca agcctacaaa agcaccaacc    240
ttcaagacaa ccaaaaaaga tcacaaacct caaaccacta aaccaaagga agtacccacc    300
accaag                                                               306

<210> SEQ ID NO 70
<211> LENGTH: 102
<212> TYPE: PRT
<213> ORGANISM: Artificial Sequence
<220> FEATURE:
<223> OTHER INFORMATION: RSV Mutant Fragment

<400> SEQUENCE: 70

Pro Thr Thr Val Lys Thr Lys Asn Thr Thr Thr Thr Gln Thr Gln Pro
 1               5                  10                  15

Ser Lys Pro Thr Thr Lys Gln Arg Gln Asn Lys Pro Asn Asn Lys Pro
                20                  25                  30

Asn Asn Asp Phe His Phe Glu Val Phe Asn Phe Val Pro Cys Ser Ile
            35                  40                  45

Cys Ser Asn Asn Pro Thr Cys Trp Ala Ile Cys Lys Arg Ile Pro Asn
        50                  55                  60

Lys Lys Pro Gly Lys Lys Thr Thr Thr Lys Pro Thr Lys Ala Pro Thr
65                  70                  75                  80

Phe Lys Thr Thr Lys Lys Asp His Lys Pro Gln Thr Thr Lys Pro Lys
                85                  90                  95

Glu Val Pro Thr Thr Lys
            100

<210> SEQ ID NO 71
<211> LENGTH: 8
<212> TYPE: PRT
<213> ORGANISM: Artificial Sequence
<220> FEATURE:
<223> OTHER INFORMATION: Epitope Tag

<400> SEQUENCE: 71

Asp Tyr Lys Asp Asp Asp Asp Lys
 1               5

<210> SEQ ID NO 72
<211> LENGTH: 8
<212> TYPE: PRT
<213> ORGANISM: Artificial Sequence
<220> FEATURE:
<223> OTHER INFORMATION: Epitope Tag

<400> SEQUENCE: 72

Asp Leu Tyr Asp Asp Asp Asp Lys
 1               5
```